United States Patent
Sekine et al.

(10) Patent No.: US 6,623,810 B2
(45) Date of Patent: Sep. 23, 2003

(54) PHENYLACETYLENE COMPOUND, LIQUID CRYSTAL COMPOSITION, AND LIQUID CRYSTAL ELEMENT PRODUCED WITH THE SAME

(75) Inventors: Chizu Sekine, Tsukuba (JP); Koichi Fujisawa, Tsukuba (JP); Kazunori Iwakura, Ibaraki (JP); Masayoshi Minai, Moriyama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/840,983

(22) Filed: Apr. 25, 2001

(65) Prior Publication Data

US 2001/0050353 A1 Dec. 13, 2001

(30) Foreign Application Priority Data

Apr. 25, 2000 (JP) ........................... 2000-124957
Apr. 25, 2000 (JP) ........................... 2000-124958
May 24, 2000 (JP) ........................... 2000-152867

(51) Int. Cl.[7] .................. C09K 19/42; C09K 19/30; C09K 19/18; C07C 25/24

(52) U.S. Cl. .................. 428/1.1; 570/128; 252/299.01; 252/299.63

(58) Field of Search ............... 252/299.01, 299.63; 428/1.1; 570/128, 153, 175, 189

(56) References Cited

FOREIGN PATENT DOCUMENTS

JP         09216841         8/1997

OTHER PUBLICATIONS

Chemical Abstracts, Abst. No. 135:226742 & Tetrahedron, 2001, vol. 57(24), pp. 5109–5121.
Chemical Abstracts, Abst. No. 134:367564 & Huaxue Xuebao, 2001, vol. 59(3), pp. 433–437.
Chemical Abstracts, Abst. No. 133:65426 & J. Mater. Sci.: Mater. Electron., 2000, vol. 11(2), pp. 117–122.
Chemical Abstracts, Abst. No. 128:75758 & Macromolecules, 1998, vol. 31(1), pp. 52–58.
Chemical Abstracts, Abst. No. 126:299542 & EPO763965A2.
Chemical Abstracts, Abst. No. 124:342744 & Synthesis, 1996, vol. (2), pp. 230–236.
Chemical Abstracts, Abst. No. 124:134330 & J. Am. Chem. Soc., 1995, vol. 117 (50), pp. 12593–12602.
Chemical Abstracts, Abst. No. 124:100966 & J. Am. Chem. Soc., 1996, vol. 118(5), pp. 1213–1214.
Chemical Abstracts, Abst. No. 124–30531 & Macromolecules, 1996, vol. 29(1), pp. 446–455.
Chemical Abstracts, Abst. No. 123:245685 & J. Am. Chem. Soc., 1995, vol. 117(26), pp. 7017–7018.
Chemical Abstracts, Abst. No. 122:189062 & J. Phys. Chem., 1995, vol. 99(14), pp. 4886–4893.
Chemical Abstracts, Abst. No. 120:135281 & Macromol. Chem. Phys., 1994, vol. 195(1), pp. 303–314.
Chemical Abstracts, Abst. No. 95:114953 & Izv. Akad. Nauk SSSR, Ser. Khim., 1981, vol. (4), pp. 827–830.

Primary Examiner—Shean C. Wu
(74) Attorney, Agent, or Firm—Birch, Stewart, Kolasch & Birch, LLP

(57) ABSTRACT

The present invention provides novel phenylacetylene compounds, liquid crystal compositions having a large refractive index anisotropy ($\Delta n$), and liquid crystal elements produced with the same. The liquid crystal composition contains at least one compound of formula (3A), and at least one compound selected from the group consisting of compounds of any one of formulae (3B) to (3C), wherein $A^1$ to $A^{12}$: alkyl group optionally substituted with F; $R^1$, $R^2$: H, F; $A^{13}$ to $A^{24}$: H, F; m: 0 or 1; Rings A to D: 1,4-phnylene, 1,4-cyclohexylene; $R^5$, $R^6$: H, F; $Z^1$ to $Z^3$: —COO—, —OCO—; b to d: 0 or 1 with b+c+d≦1; $B^1$ to $B^{12}$: alkyl or alkoxy group; $R^7$, $R^8$: H, F:

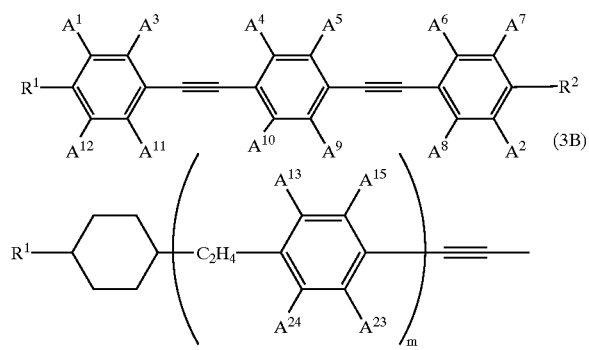

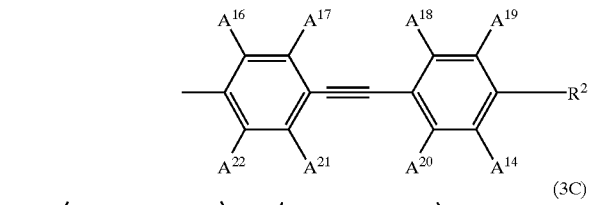

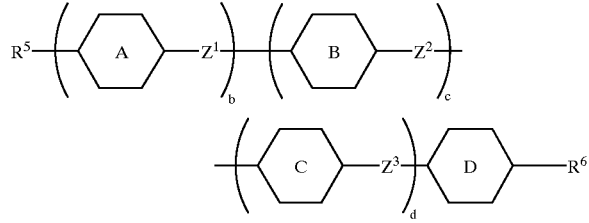

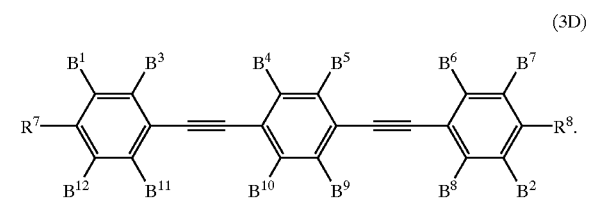

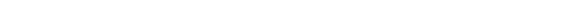

8 Claims, No Drawings

PHENYLACETYLENE COMPOUND, LIQUID CRYSTAL COMPOSITION, AND LIQUID CRYSTAL ELEMENT PRODUCED WITH THE SAME

FIELD OF ART

The present invention relates to novel phenylacetylene compounds having at least one alkoxy group bound to its skeleton and novel phenylacetylene compounds having a cyclopropane or alkenyl group bound to its skeleton, which compounds are useful as a material for fabricating liquid crystal display devices or as a constituent of liquid crystal compositions. The present invention also relates to liquid crystal compositions having a large refractive index anisotropy ($\Delta n$), and liquid crystal elements produced with such compositions such as optical shutters or display devices including STN (supertwisted nematic) liquid crystal elements, or polymer dispersed liquid crystal (PDLC) elements.

BACKGROUND ART

Improvement in performance of liquid crystal display elements has become essential with the recent development in information-oriented society. For higher processing speed and performance, liquid crystal compositions need to contain a material having a large refractive index anisotropy.

A tolan compound is known as liquid crystal having a relatively large refractive index anisotropy (Mol. Cryst. Liq. Cryst., Vol.23, p233 (1973)). However, the refractive index anisotropy of this compound is about 0.2, which is not yet large enough.

There is also developed a compound represented by the formula:

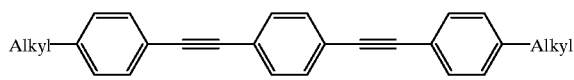

wherein "Alkyl" stands for an alkyl group (JP-A-2-83340). Though this compound has a refractive index anisotropy of 0.3 or larger, it has poor compatibility with other liquid crystals, and is thus not practical.

There is further developed, aiming at improvement in the compatibility with other liquid crystals, a compound represented by the formula:

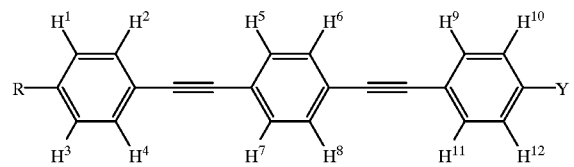

wherein R stands for an alkyl group, Y stands for R, a fluorine atom, a chlorine atom, a bromine atom, an iodine atom, or a cyano group; $H^1$ to $H^{12}$ each stands for a hydrogen, fluorine, or chlorine atom, and at least one of $H^1$ to $H^{12}$ is a fluorine or chlorine atom (JP-A-9-216841). This compound is improved in compatibility with other liquid crystals, but is not yet sufficient in refractive index anisotropy.

On the other hand, with the recent development in information-oriented society, display devices has been assuming importance as one type of man-machine interfaces. Among the display devices, flat displays, in particular liquid crystal displays (LCDs) have been rapidly spreading for their thinness, light weight, low driving voltage, and low power consumption. Among liquid crystal elements including such liquid crystal displays, matrix type liquid crystal elements that can provide a large amount of information employ two types of addressing systems, active and simple matrices.

In the active matrix elements, each pixel is provided with a thin film transistor made of polysilicon or amorphous silicon or a diode, as a nonlinear element. However, simple matrix elements currently prevails for its costs and productivity, since active matrix elements have problems in increasing areal size, reducing of costs, and increasing density, due to its complex manufacture process and low process yield.

Simple matrix liquid crystal elements currently in practical use are mainly TN (twisted nematic) or STN liquid crystal elements. TN elements are widely used as display devices for watches and calculators. In this system, the electro-optical property curve is not steep, and the contrast remarkably decreases as the duty increases, which properties cause difficulties in creating large displays. STN elements, which have been developed for overcoming such disadvantages of the TN elements, can be used for fabricating large displays owing to its steep electro-optical property curve, and are now used for manufacturing displays of laptop personal computers.

Though STN elements have superior properties compared to TN elements, these elements yet have problems to be solved for realizing still larger displays, lower costs, and higher density. For example, STN liquid crystal elements are still insufficient in viewing angle and response speed compared to TFT liquid crystal elements, which are typically used in active matrix displays. High response speed is particularly essential for large displays, higher density, and movie pictures display.

One of the effective means for increasing the response speed of STN liquid crystal elements is to reduce the cell thickness. However, STN elements utilize birefringence effect for displaying, which requires suppression of change in optical properties and color tone of the panel, i.e. requires maintenance of retardation R represented by R=($\Delta n \times d$) at a particular optimum value, so that the reduction in cell thickness d will require increase in refractive index anisotropy $\Delta n$.

Liquid crystal compositions with larger $\Delta n$ have, however, larger viscosity in general, and thus are not suitable for achieving high response speed. Liquid crystal compositions having larger $\Delta n$ and lower viscosity are demanded.

In addition, response parameter $\eta/\Delta n^2$ is known to be well correlated with response speed, and the smaller the value of the response parameter, the shorter the response speed tends to be. Thus, liquid crystal having a smaller response parameter is desired.

However, compounds having larger $\Delta n$ are generally poor in compatibility with other liquid crystals, and have difficulty in exhibiting a nematic phase over a wide temperature range in lower temperature region. JP-A-9-216841 discloses, for example, a composition containing a liquid crystal compound that has a large Δn and improved compatibility with other liquid crystals. Though this compound is said to have stability at lower temperatures, Δn of the composition per se is not very large.

DISCLOSURE OF THE INVENTION

It is therefore an object of the present invention to provide a novel phenylacetylene compound that has a large refractive index anisotropy, is easy to mix with other liquid crystals, and has advantageous stability against light.

It is another object of the present invention to provide a liquid crystal composition having a large refractive index anisotropy (Δn), and a liquid crystal element produced with such a liquid crystal composition that may be used for manufacturing optical shutters and display devices.

It is yet another object of the present invention to provide a liquid crystal composition that has a large refractive index anisotropy and exhibits a nematic phase over a wide temperature range including room temperature, a liquid crystal composition that has a small response parameter ($\eta/\Delta n^2$) and provides excellent response time, and a liquid crystal element produced with such a composition.

According to the present invention, there is provided a phenylacetylene compound represented by the formula (1A):

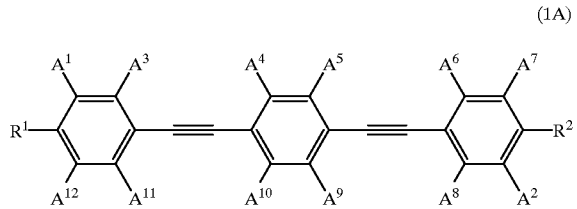

(1A)

wherein $A^1$ to $A^{12}$ each independently stands for a hydrogen atom, a fluorine atom, an alkoxy group having 1 to 10 carbon atoms, or an alkyl group having 1 to 10 carbon atoms optionally substituted with at least one fluorine atom, with at least one of $A^1$ to $A^{12}$ being an alkoxy group having 1 to 10 carbon atoms; $R^1$ and $R^2$ each independently stands for a hydrogen atom, a fluorine atom, a cyano group, —$SF_5$, —NCS, a 4-$R^3$-(cycloalkyl) group, a 4-$R^3$-(cycloalkenyl) group, or a $R^4$—(O)q group, wherein $R^3$ stands for a hydrogen atom or a straight or branched alkyl group having 1 to 12 carbon atoms optionally substituted with at least one fluorine atom, $R^4$ stands for a straight or branched alkyl group having 1 to 12 carbon atoms optionally substituted with at least one fluorine atom, and q is 0 or 1.

According to the present invention, there is also provided a phenylacetylene compound represented by the formula (2A):

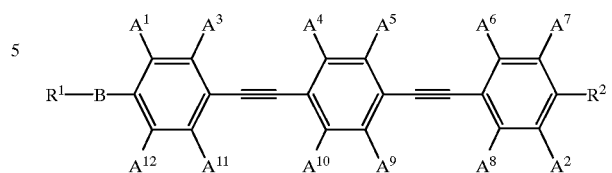

(2A)

wherein $A^1$ to $A^{12}$ each independently stands for a hydrogen atom, a fluorine atom, or an alkyl or alkoxy group having 1 to 10 carbon atoms optionally substituted with at least one fluorine atom, with at least one of $A^1$ to $A^{12}$ being an alkyl or alkoxy group having 1 to 10 carbon atoms optionally substituted with at least one fluorine atom; B stands for:

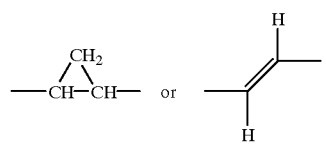

$R^1$ stands for a straight or branched alkyl group having 1 to 12 carbon atoms optionally substituted with at least one fluorine atom; and $R^2$ means the same as $R^2$ in the formula (1A).

According to the present invention, there is also provided a liquid crystal composition comprising at least one phenylacetylene compound represented by the formula (2A).

According to the present invention, there is further provided a liquid crystal composition comprising at least one benzylidynyl tolan compound represented by the formula (3A), and at least one compound selected from the group consisting of compounds represented by any one of the formulae (3B) (3C), and (3D):

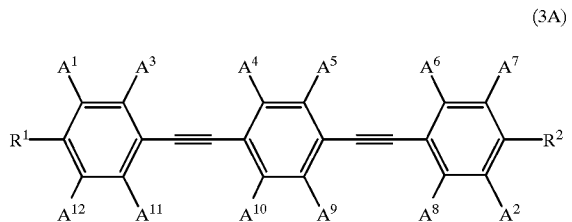

(3A)

wherein $A^1$ to $A^{12}$ each independently stands for a hydrogen atom, a fluorine atom, or an alkyl or alkoxy group having 1 to 10 carbon atoms optionally substituted with at least one fluorine atom, with at least one of $A^1$ to $A^{12}$ being an alkyl or alkoxy group having 1 to 10 carbon atoms substituted with at least one fluorine atom; $R^1$ and $R^2$ mean the same as $R^1$ and $R^2$ in the formula (1A), respectively;

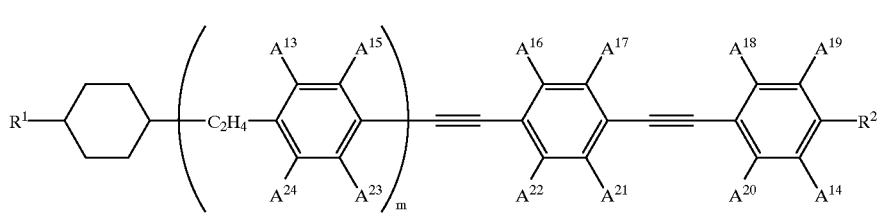

(3B)

wherein $A^{13}$ to $A^{24}$ each independently stands for a hydrogen atom, a fluorine atom, or an alkyl group having 1 to 10 carbon atoms; m is 0 or 1; $R^1$ stands for a hydrogen atom or a straight or branched alkyl group having 1 to 12 carbon atoms optionally substituted with at least one fluorine atom; $R^2$ stands for $R^1$, a fluorine atom, a cyano group, a 4-$R^{31}$-(cycloalkyl) group, a 4-$R^{31}$-(cycloalkenyl) group, or a $R^{41}$—(O)q group, wherein $R^{31}$, $R^{41}$, and q mean the same as $R^3$, $R^4$, and q in the formula (1A), respectively;

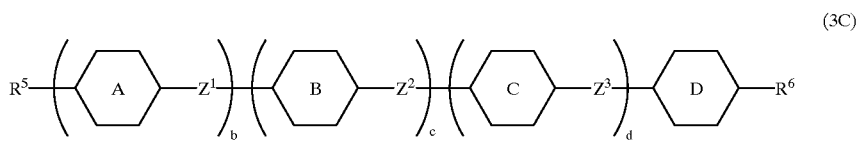

(3C)

wherein Rings A, B, C, and D each independently stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl, with at least one of hydrogen atoms on Rings A, B, C, and D being optionally substituted with a fluorine atom; $R^5$ and $R^6$ each independently stands for a hydrogen atom, a fluorine atom, a fluoromethyl group, a difluoromethyl group, a trifluoromethyl group, a fluoromethoxy group, a difluoromethoxy group, a trifluoromethoxy group, a cyano group, an alkyl group having 1 to 12 carbon atoms, an alkenyl group having 2 to 12 carbon atoms, an alkoxy group having 1 to 12 carbon atoms, an alkenyloxy group having 2 to 12 carbon atoms, an alkynyloxy group having 3 to 12 carbon atoms, an alkoxyalkyl group having 2 to 16 carbon atoms, or an alkoxyalkenyl group having 3 to 16 carbon atoms, with at least one of methylene groups in these groups being optionally substituted with an oxygen, sulfur, or silicon atom, wherein these groups may be straight or branched; $Z^1$, $Z^2$ and $Z^3$ each independently stands for —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond; b, c, and d each independently denotes 0 or 1 with b+c+d≧1;

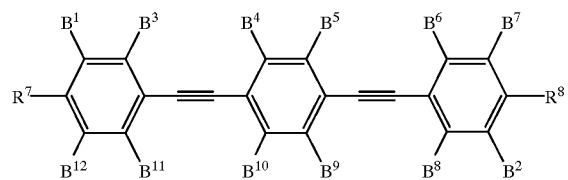

(3D)

wherein $B^1$ to $B^{12}$ each independently stands for a hydrogen atom, a fluorine atom, or an alkyl or alkoxy group having 1 to 10 carbon atoms, with at least one of $B^1$ to $B^{12}$ being an alkyl or alkoxy group having 1 to 10 carbon atoms; $R^7$ and $R^8$ each independently stands for a hydrogen atom, a fluorine atom, a cyano group, a 4-$R^9$-(cycloalkyl) group, 4-$R^9$-(cycloalkenyl) group, or a $R^{10}$—(O)q group, wherein $R^9$, $R^{10}$, and q mean the same as $R^3$, $R^4$, and q in the formula (1A), respectively.

According to the present invention, there is also provided a liquid crystal element comprising any of the liquid crystal composition mentioned above held between a pair of electrode substrates.

PREFERRED EMBODIMENTS OF THE INVENTION

The present invention will now be explained in detail.

One phenylacetylene compound of the present invention is represented by the formula (1A) above. In the formula (1A), $A^1$ to $A^{12}$ each independently stands for a hydrogen atom, a fluorine atom, an alkoxy group having 1 to 10 carbon atoms, or an alkyl group having 1 to 10 carbon atoms optionally substituted with at least one fluorine atom. At least one of $A^1$ to $A^{12}$ is an alkoxy group having 1 to 10 carbon atoms, and preferably at least one of $A^4$, $A^5$, $A^9$, and $A^{10}$ is an alkoxy group having 1 to 10 carbon atoms.

In the formula (1A), $R^1$ and $R^2$ each independently stands for a hydrogen atom, a fluorine atom, a cyano group, —$SF_5$, —NCS, a 4-$R^3$-(cycloalkyl) group, a 4-$R^3$-(cycloalkenyl) group, or a $R^4$—(O)q group, wherein $R^3$ stands for a hydrogen atom or a straight or branched alkyl group having 1 to 12 carbon atoms optionally substituted with at least one fluorine atom, $R^4$ stands for a straight or branched alkyl group having 1 to 12 carbon atoms optionally substituted with at least one fluorine atom, and q is 0 or 1.

Examples of $R^1$ and $R^2$ include a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group; a 4-alkyl-cycloalkyl group such as a 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkyl-cycloalkyl group substituted with at least one fluorine atom, i.e., a 4-fluoroalkyl-cycloalkyl group; a 4-alkyl-cycloalkenyl group such as a 4-propylcyclohexenyl or 4-pentylcyclohexenyl group, or a 4-alkyl-cycloalkenyl group substituted with at least one fluorine atom, i.e., a 4-fluoroalkyl-cycloalkenyl group; a cyano group; —$SF_5$; or —NCS.

Examples of the phenylacetylene compound represented by the formula (1A) include compounds represented by the following formulae, wherein $R^1$ and $R^2$ each preferably stands for any of those mentioned above, but is not limited thereto.

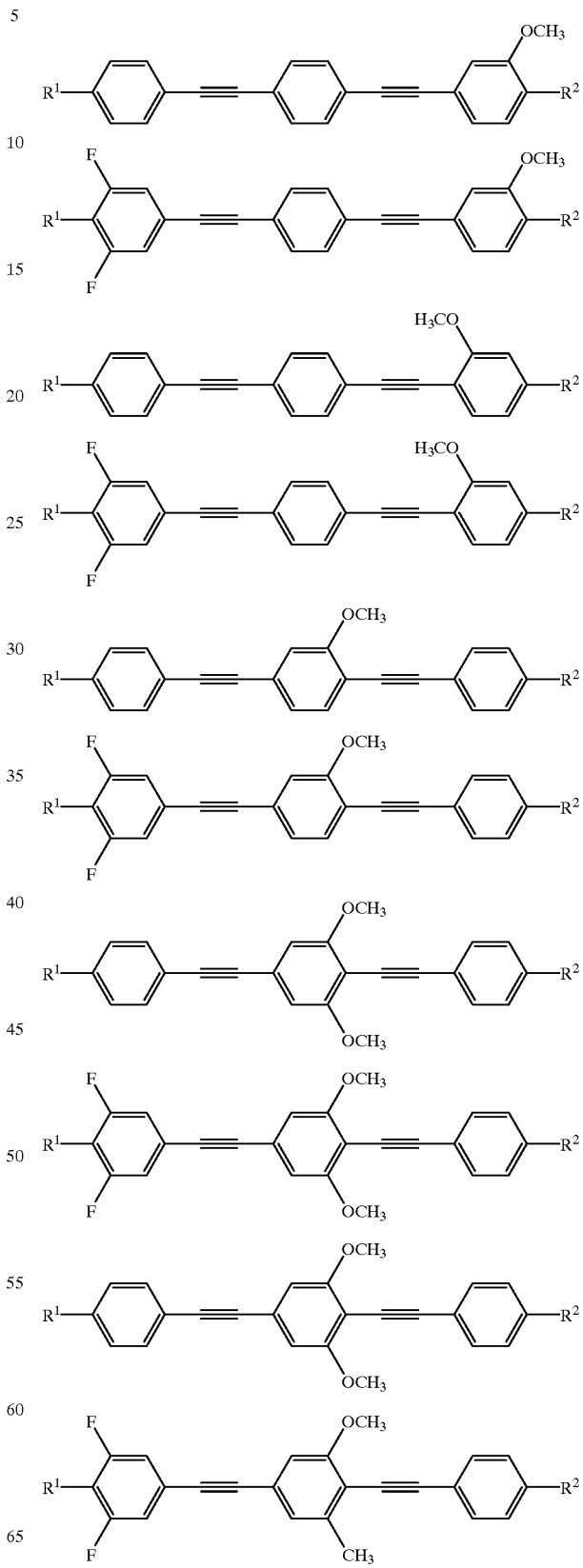

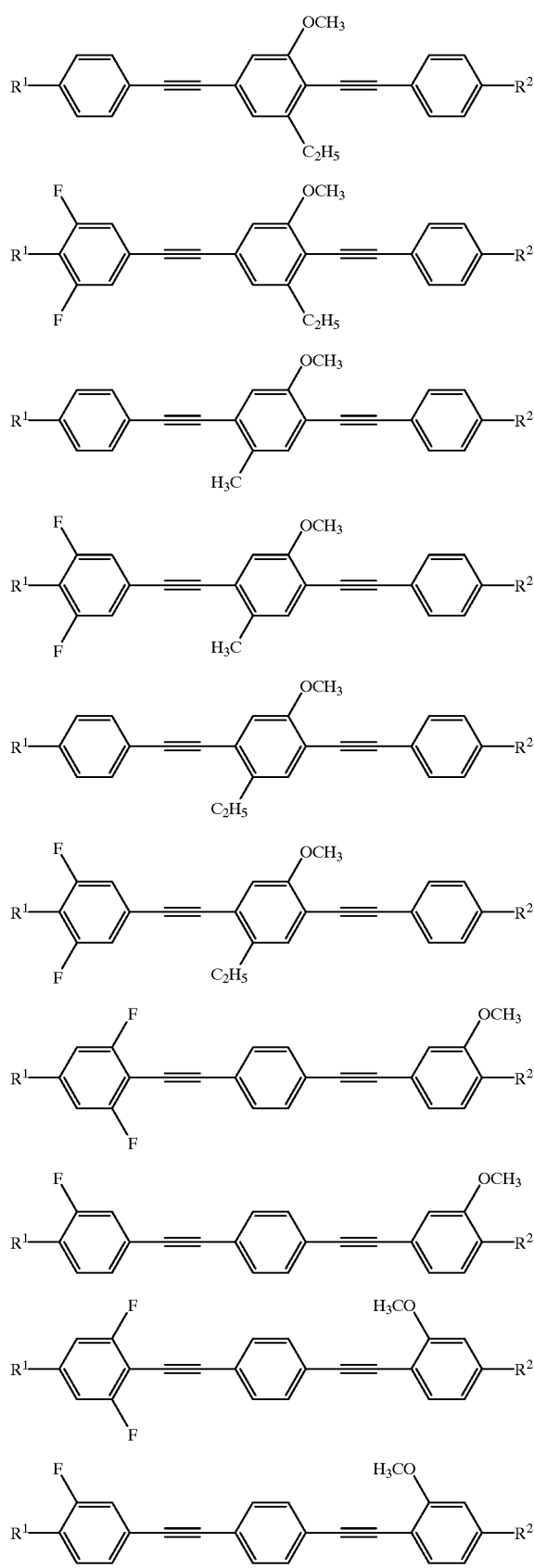
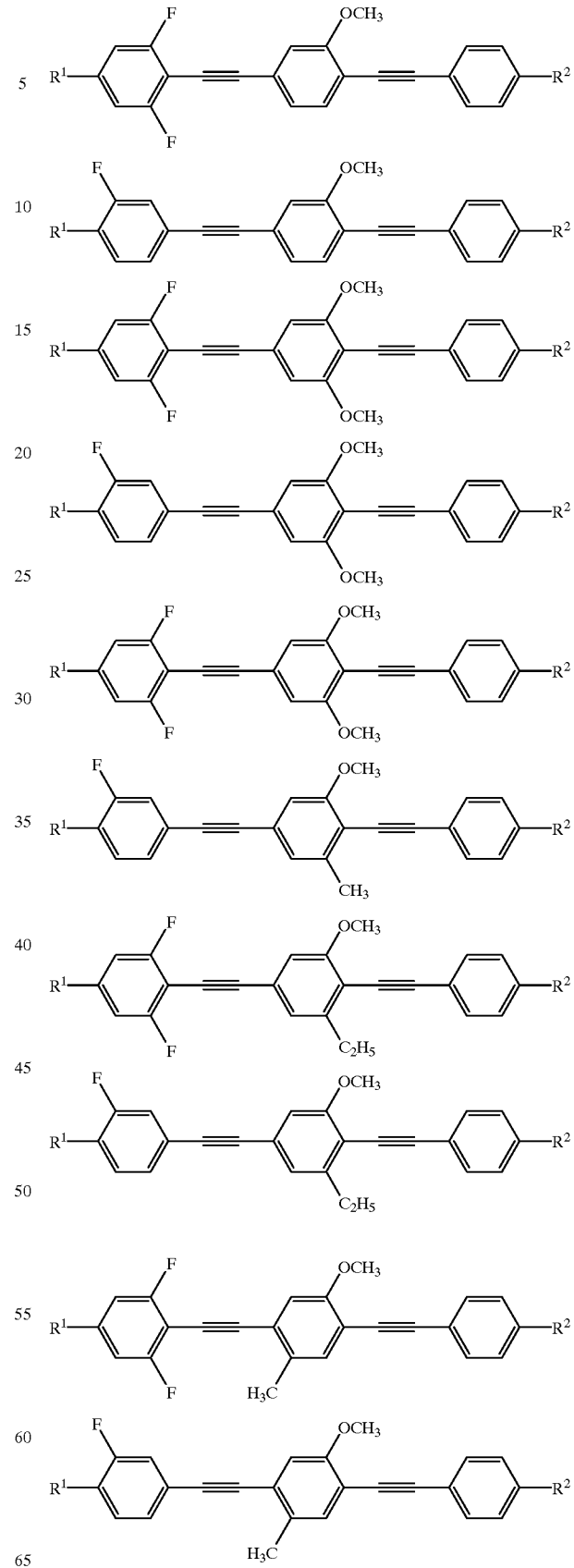

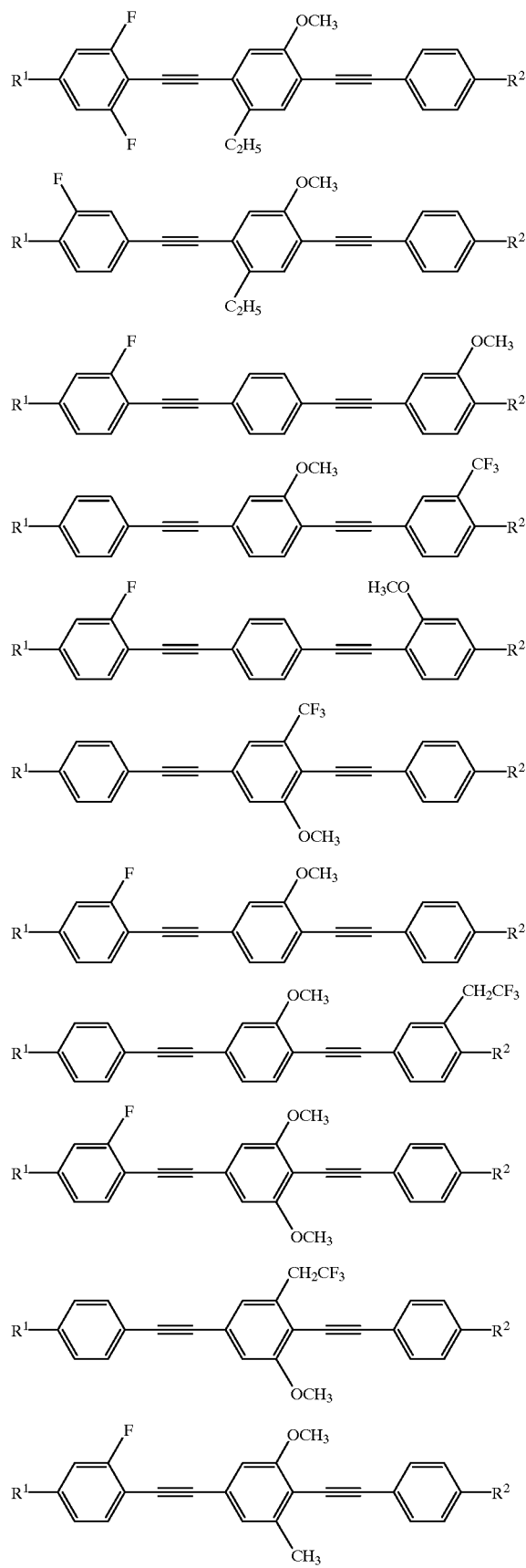
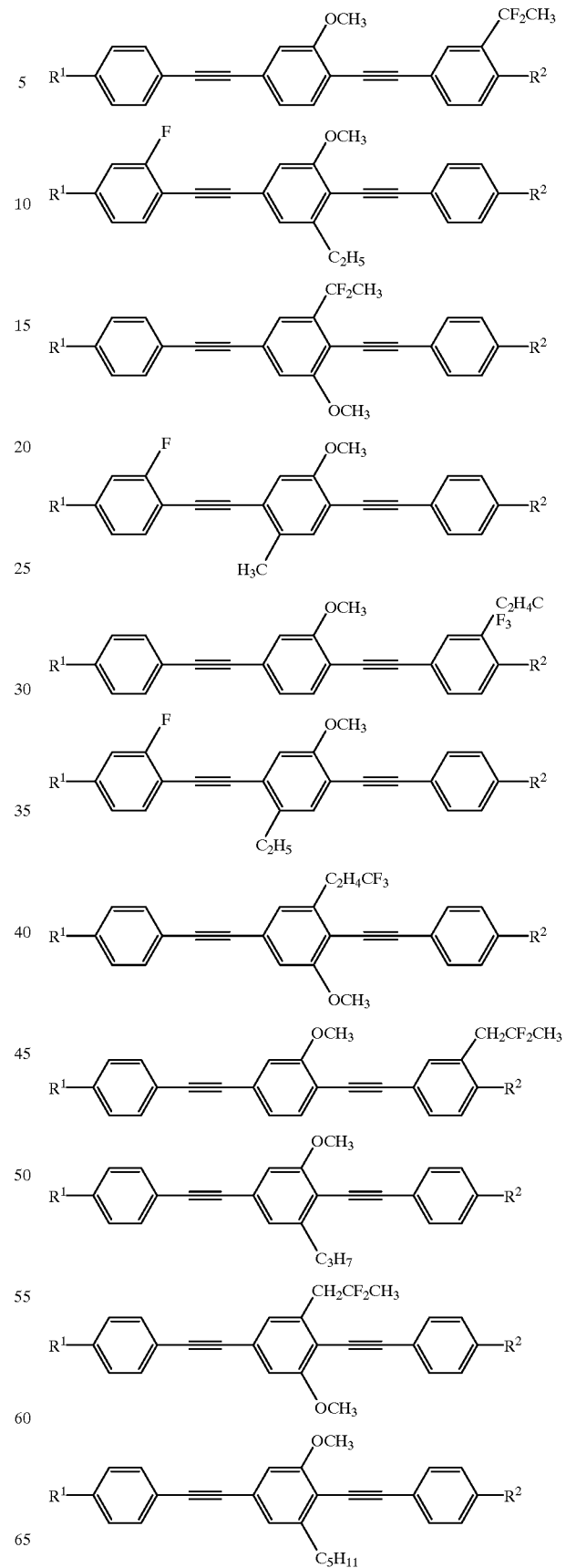

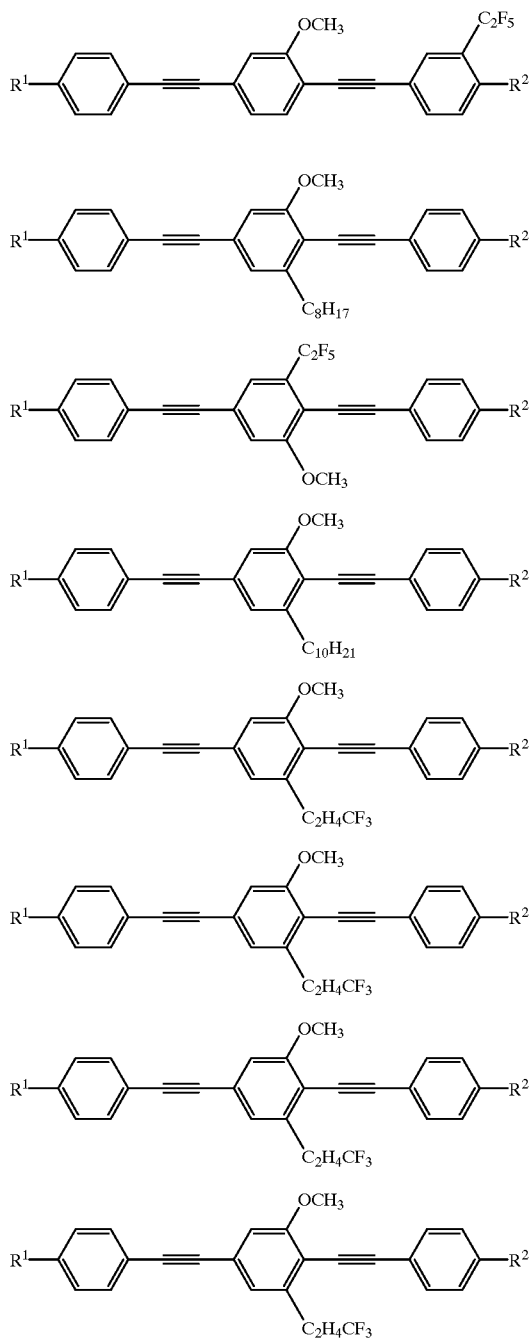

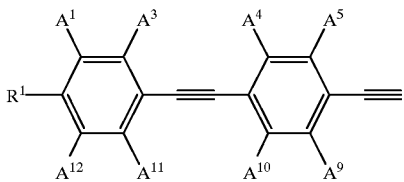

(IM-1)

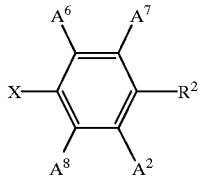

(IM-2)

wherein $A^1$ to $A^{12}$, $R^1$, and $R^2$ are the same as those in the formula (1A); X stands for I, Br, Cl, —$OSO_2CH_3$, —$OSO_2CF_3$, or —$OSO_2$—$C_6H_4$—$CH_3$.

The compound represented by the formula (IM-1) may be prepared, for example, by coupling compounds represented by the formulae (M-1) and (M-2), followed by reaction with 3-methyl-1-butyne-3-ol in the presence of a palladium catalyst and a base such as triethyl amine and in the presence or absence of copper iodide, and then reaction in the presence of a base such as potassium hydroxide:

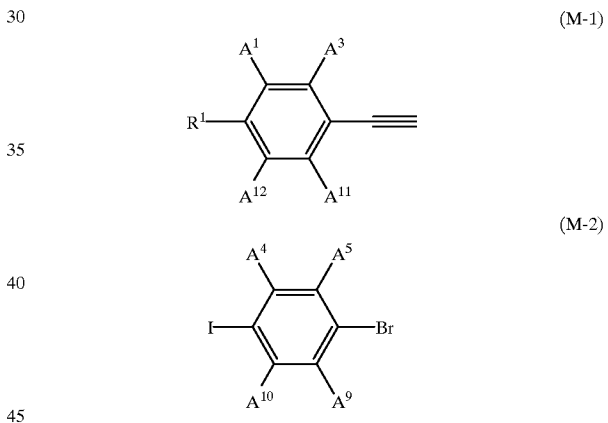

wherein $A^1$, $A^3$ to $A^5$, $A^9$ to $A^{12}$, and $R^1$ mean the same as those in the formula (1A), respectively.

In the reaction of the compounds represented by the formulae (IM-1) and (IM-2) for preparing the phenylacetylene compound represented by the formula (1A), the amount of the compound (IM-2) used is usually an equivalent of 0.3 to 10 times, preferably 0.5 to 2 times the amount of the compound (IM-1).

The palladium catalyst used in the above reaction may be, for example, palladium chloride, palladium acetate, palladium/carbon, or triphenylphosphine palladium complex such as tetrakis(triphenylphosphine)palladium or dichlorobis(triphenylphosphine)palladium.

The amount of the palladium catalyst is usually an equivalent of 0.0001 to 1 time, preferably 0.001 to 0.1 times the amount of the compound (IM-2). The amount of the copper iodide (I) used as an additive is usually an equivalent of 0 to 1 time, preferably 0 to 0.1 times the amount of the starting material compound (IM-2).

The base used for this reaction may be a carbonate, carboxylate, alkoxide, or hydroxide of alkali metals, or an The phenylacetylene compound represented by the formula (1A) of the present invention may be synthesized through ordinary organic synthesizing processes, for example, through combination of the reactions described in "Organic Synthesis Developed by Transition Metals" Jiro Tsuji, published by Kagaku Dojin Co. A specific example of the preparation process involves reacting compounds represented by the formulae (IM-1) and (IM-2) in the presence of a palladium catalyst and a base such as triethyl amine and in the presence or absence of copper iodide:

organic base such as triethyl amine, diisopropylethyl amine, tri-n-butyl amine, tetramethylethylene diamine, 1,8-diazabicyclo[5.4.0]undecene-7, 1,5-diazabicyclo[4.3.0]nonene-5, pyridine, N,N-dimethylaminopyridine, dimethylaniline, N-methylmorpholine, or N-methylpiperidine. The base is preferably a tertiary amine such as triethyl amine.

The amount of the base is usually an equivalent of 1 to 100 times, preferably 1 to 20 times the amount of the compound (IM-2).

The temperature of the above reaction is usually −20 to 200° C., preferably 30 to 150° C. A solvent may optionally be used as desired, such as acetonitrile, tetrahydrofuran, ethylacetate, N,N-dimethylformamide, hexamethylphosphorylamide, N-methylpyrrolidone, N,N-dimethylimidazolidinone, benzene, or toluene. The amount of the solvent is not particularly limited, and may be selected suitably.

The compound represented by the formula (1A) may alternatively be prepared by reacting compounds represented by the formulae (IM-3) and (IM-4) in the presence of a palladium catalyst and a base such as triethyl amine and in the presence or absence of copper iodide:

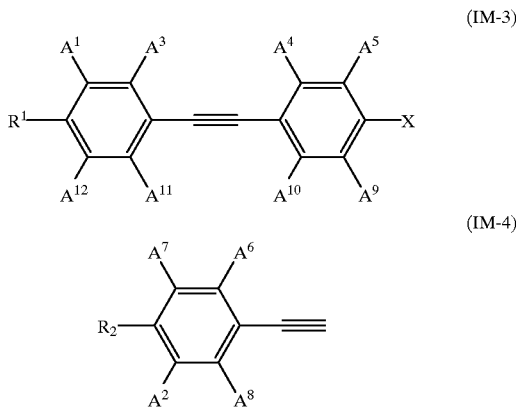

wherein $A^1$ to $A^{12}$, $R^1$, and $R^2$ mean the same as those in the formula (1A); X stands for I, Br, Cl, —OSO$_2$CH$_3$, —OSO$_2$CF$_3$, or —OSO$_2$—C$_6$H$_4$—CH$_3$.

The compound represented by the formula (IM-3) may be prepared, for example, by coupling compounds represented by the formulae (M-3) and (M-4):

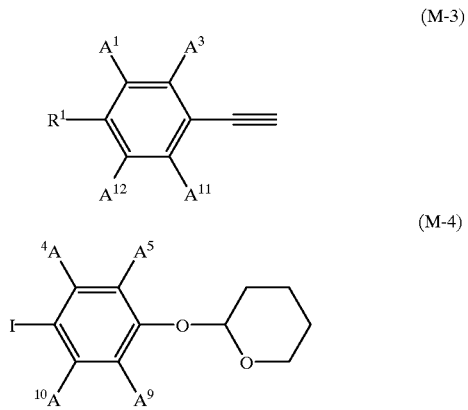

In the reaction of the compounds represented by the formulae (IM-3) and (IM-4) for preparing the phenylacetylene compound represented by the formula (1A), the amount of the compound (IM-3) used is usually an equivalent of 0.3 to 10 times, preferably 0.5 to 2 times the amount of the compound (IM-4).

The palladium catalyst used in the above reaction may be selected from those listed for the reaction of the compounds (IM-1) and (IM-2). The amount of the palladium catalyst is usually an equivalent of 0.0001 to 1 time, preferably 0.001 to 0.1 times the amount of the compound (IM-4).

The amount of the copper iodide (I) used as an additive is usually an equivalent of 0 to 1 time, preferably 0 to 0.1 times the amount of the starting material compound (IM-4).

The base used for this reaction may be selected from those listed for the reaction of the compounds (IM-1) and (IM-2). The amount of the base is usually an equivalent of 1 to 100 times, preferably 1 to 20 times the amount of the compound (IM-4).

The temperature of the reaction is usually −20 to 200° C., preferably 30 to 150° C. An ordinary solvent may optionally be used for the reaction, such as acetonitrile, tetrahydrofuran, ethylacetate, N,N-dimethylformamide, hexamethylphosphorylamide, N-methylpyrrolidone, N,N-dimethylimidazolidinone, benzene, or toluene, which is inert in the reaction. The amount of the solvent is not particularly limited, and may be selected suitably.

The other phenylacetylene compound according to the present invention is represented by the formula (2A). In the formula (2A), $A^1$ to $A^{12}$ each independently stands for a hydrogen atom, a fluorine atom, or an alkyl or alkoxy group having 1 to 10 carbon atoms optionally substituted with at least one fluorine atom. At least one of $A^1$ to $A^{12}$ is an alkyl or alkoxy group having 1 to 10 carbon atoms optionally substituted with at least one fluorine atom, and preferably at least one of $A^4$, $A^5$, $A^9$, and $A^{10}$ is an alkyl or alkoxy group having 1 to 10 carbon atoms optionally substituted with at least one fluorine atom. When any of $A^1$ to $A^{12}$ is a fluorine atom, preferably not more than four, more preferably one or two of them are fluorine atoms.

In the formula (2A), $R^1$ stands for a straight or branched alkyl group having 1 to 12 carbon atoms optionally substituted with at least one fluorine atom. $R^2$ means the same as $R^2$ in the formula (1A).

Examples of $R^1$ in the formula (2A) may include, an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group.

Examples of $R^2$ in the formula (2A) may include, a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group; a 4-alkyl-cycloalkyl group such as a 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkyl-cycloalkyl group substituted with at least one fluorine atom, i.e., a 4-fluoroalkyl-cycloalkyl group; a 4-alkyl-cycloalkenyl group such as a 4-propylcyclohexenyl or 4-pentylcyclohexenyl group, or a 4-alkyl-cycloalkenyl group substituted with at least one fluorine atom, i.e., a 4-fluoroalkyl-cycloalkenyl group; a cyano group; —SF$_5$; or —NCS.

Examples of the phenylacetylene compound represented by the formula (2A) include compounds represented by the following formulae, wherein $R^1$ and $R^2$ each preferably stands for any of those mentioned above, but is not limited thereto, and B stands for:

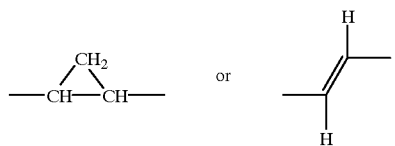

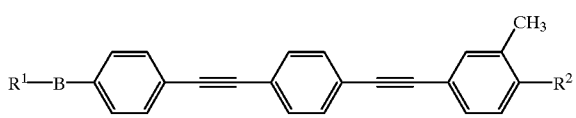

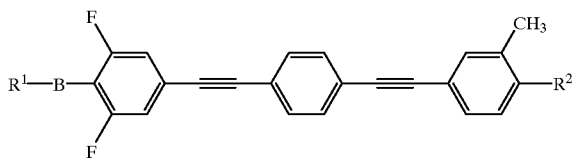

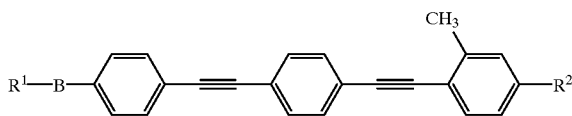

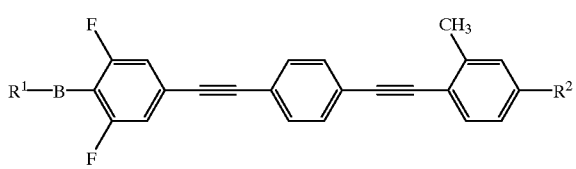

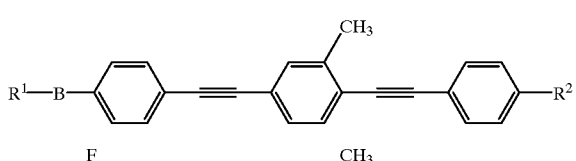

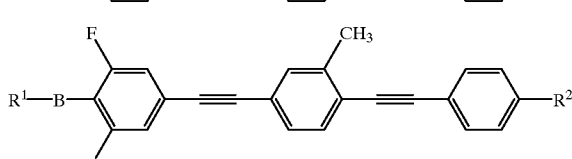

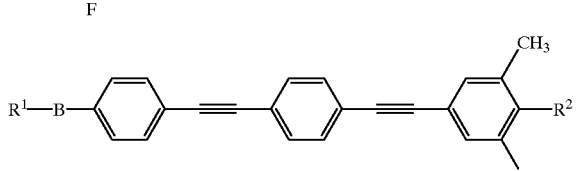

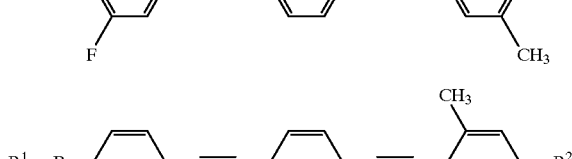

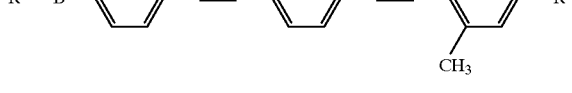

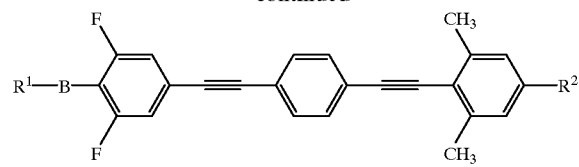
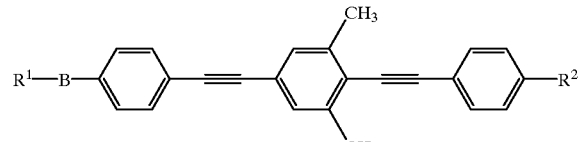
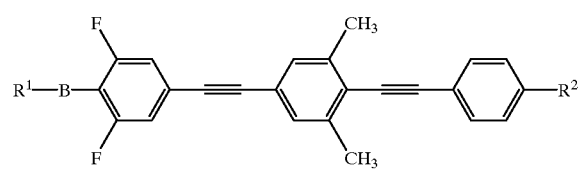
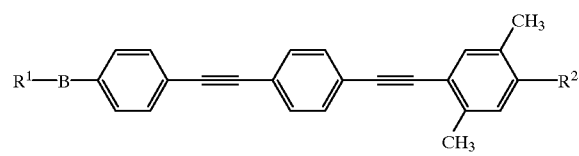
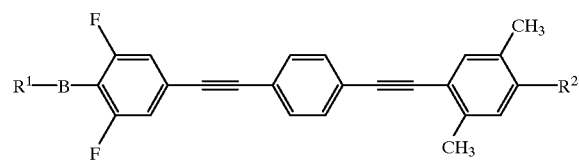
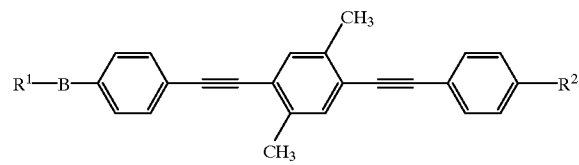
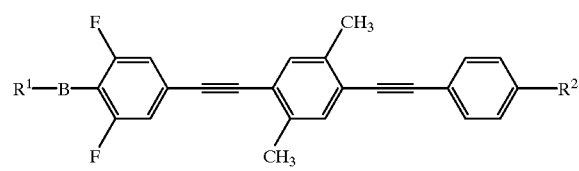
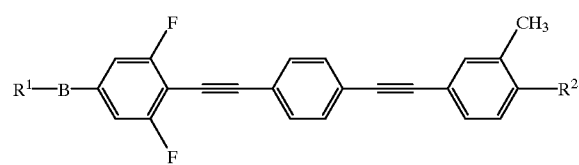
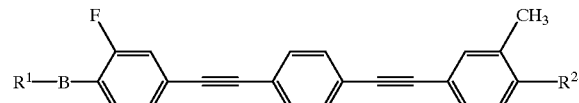
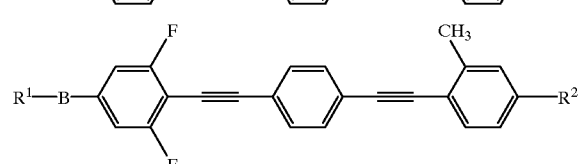
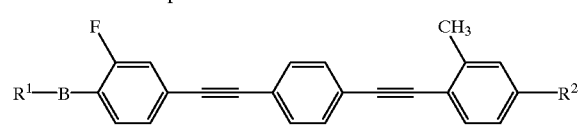
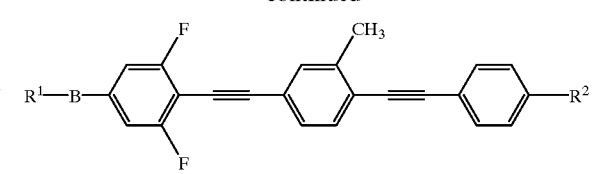
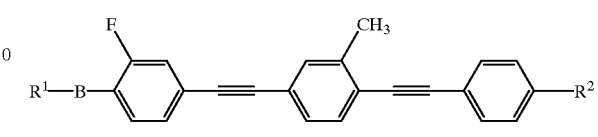
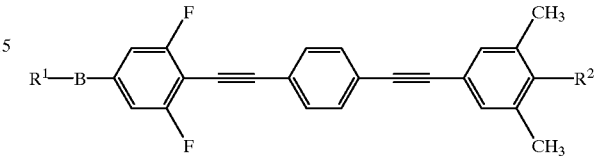
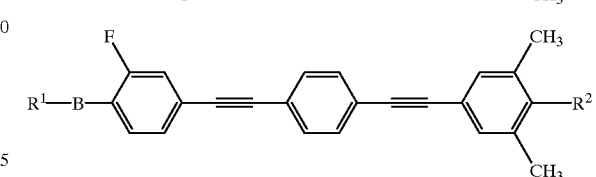
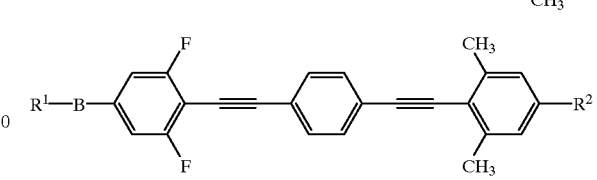
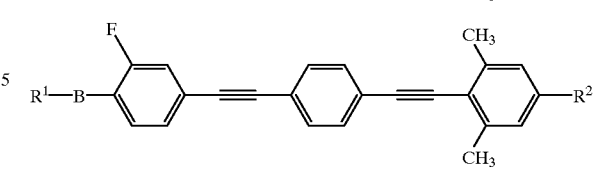
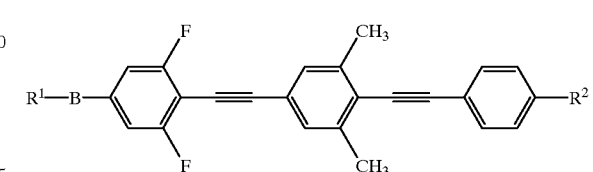
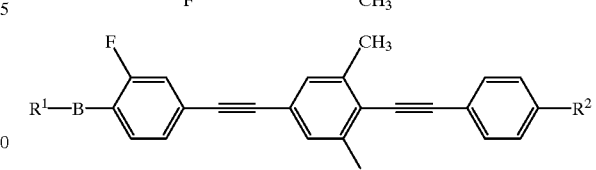
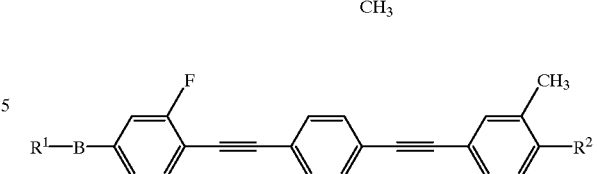
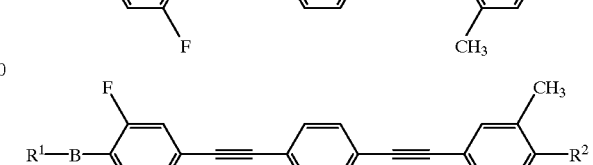
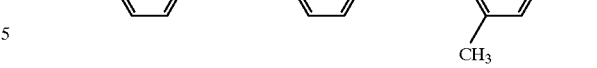

-continued
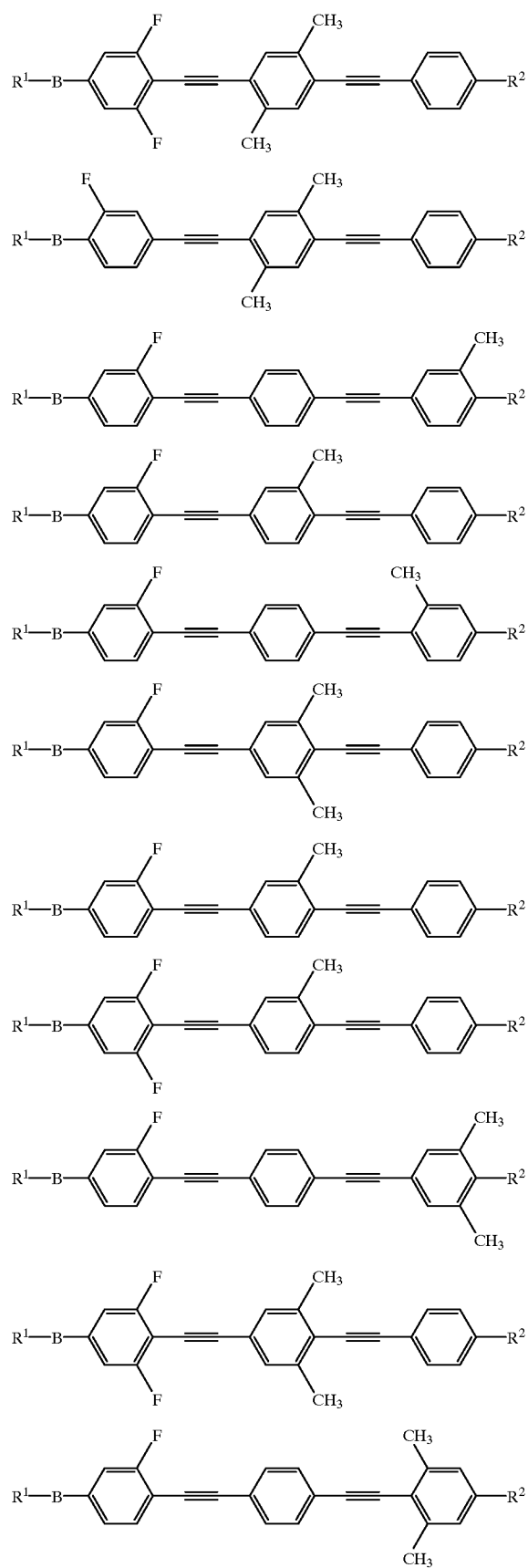
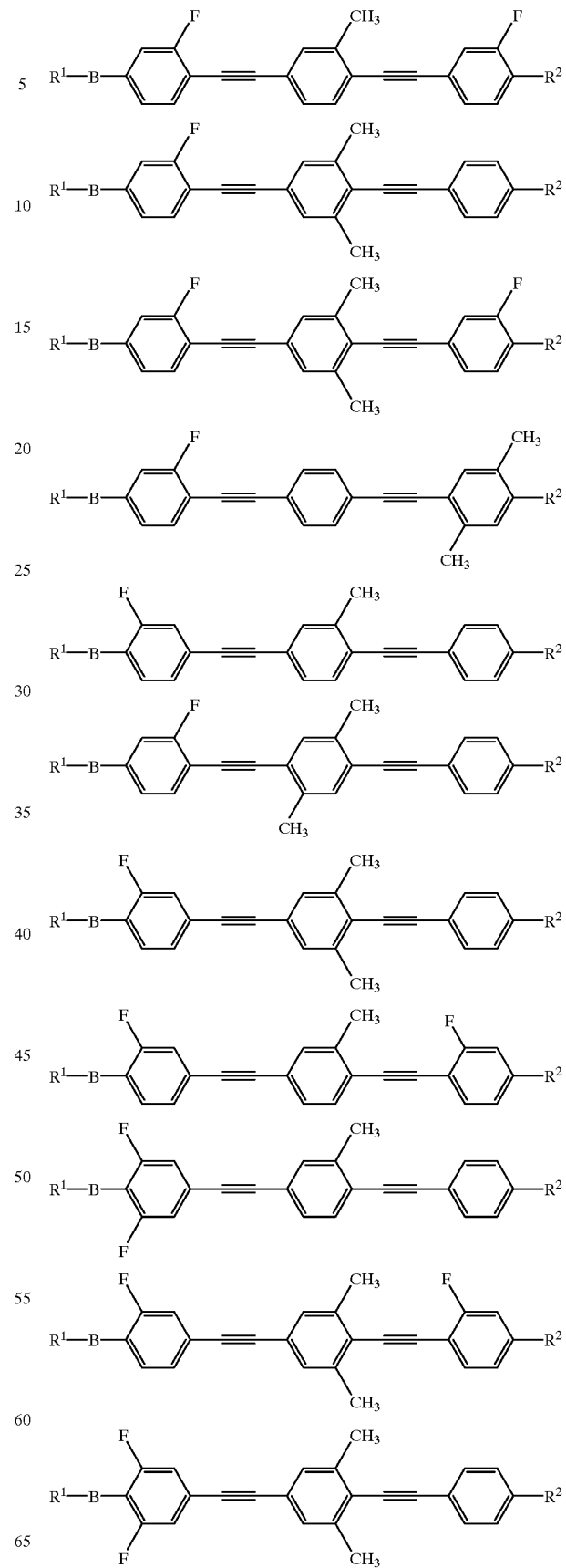

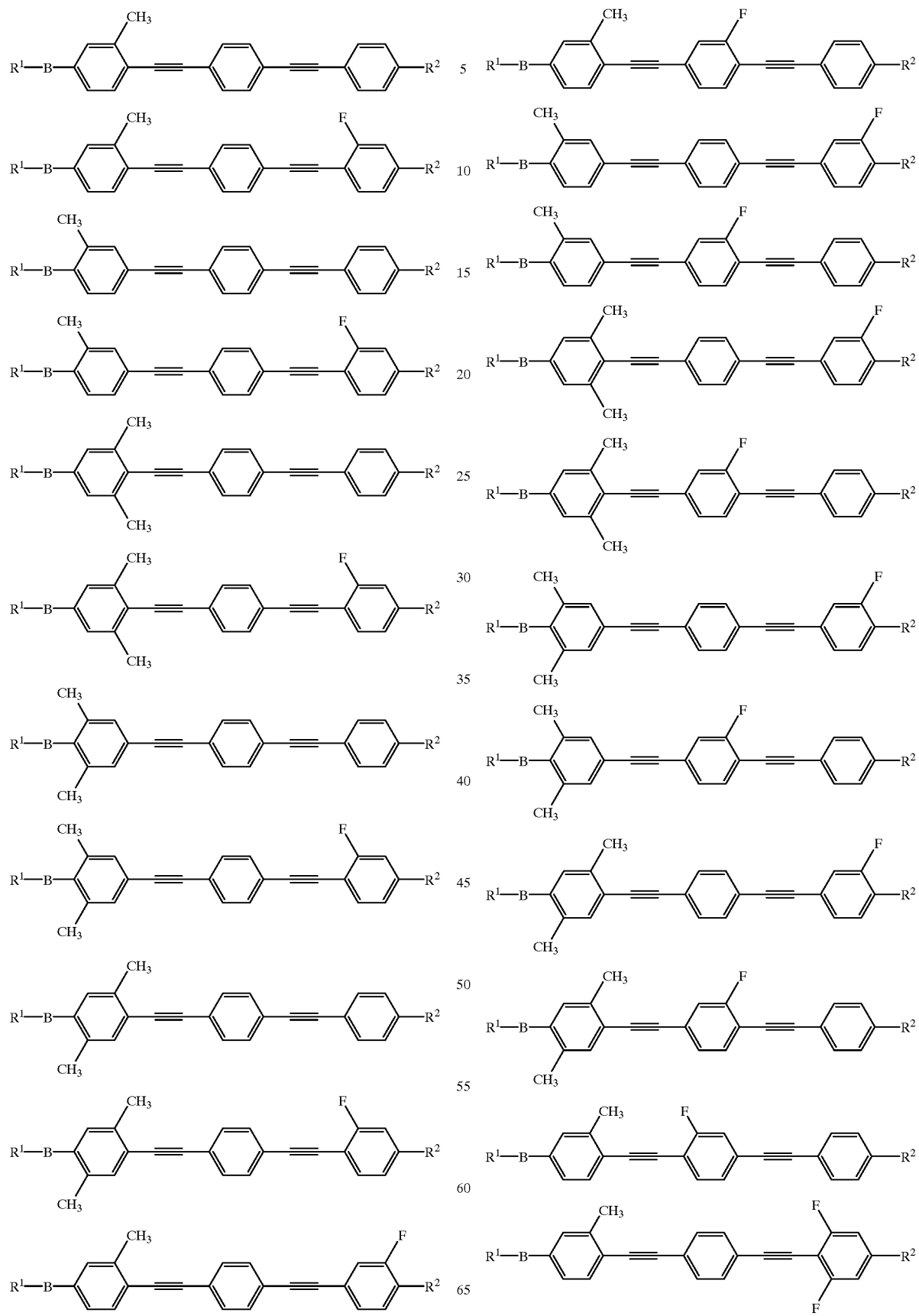

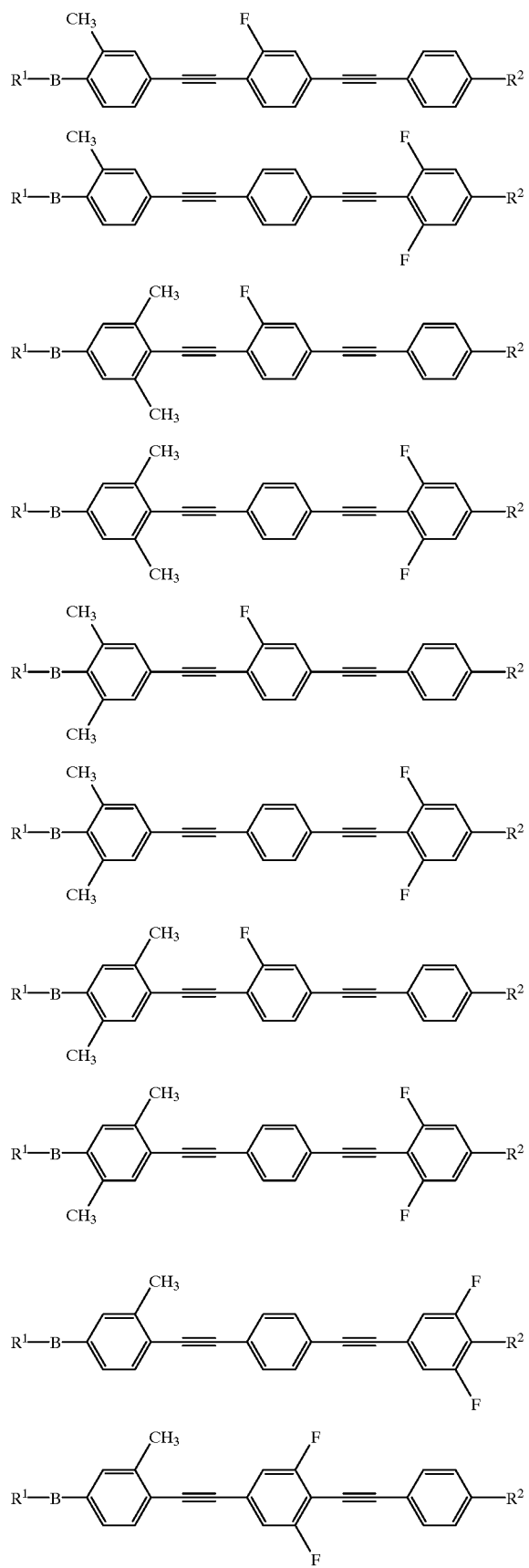
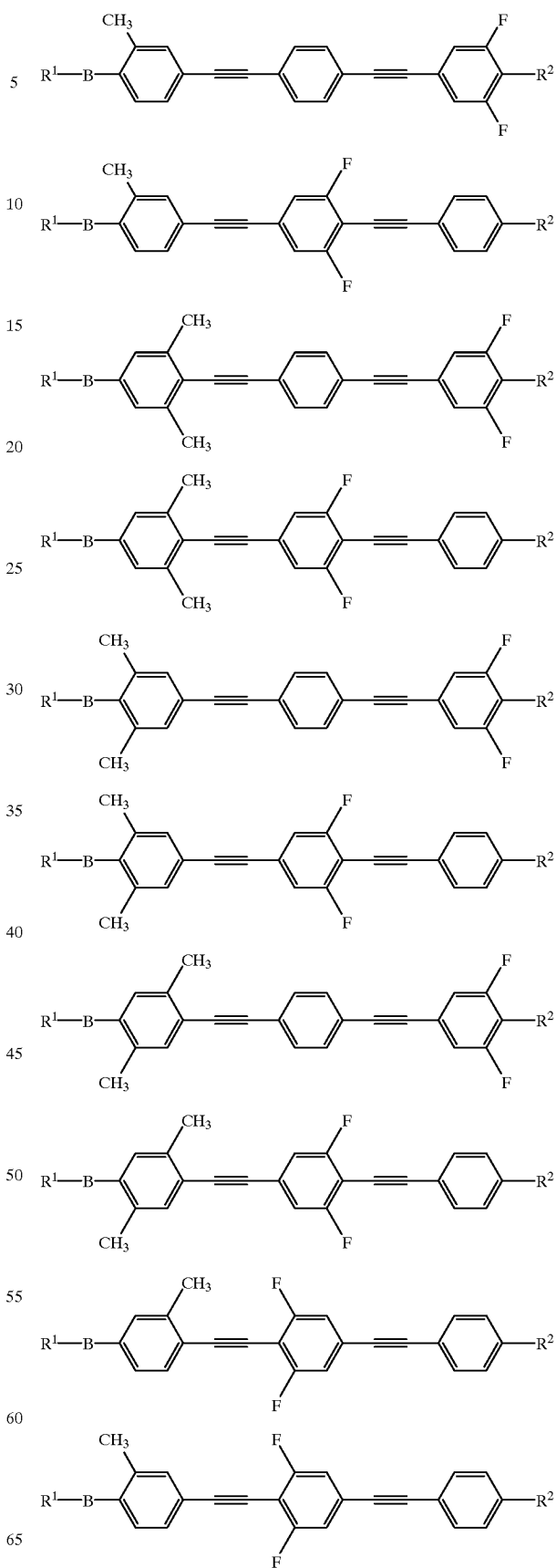

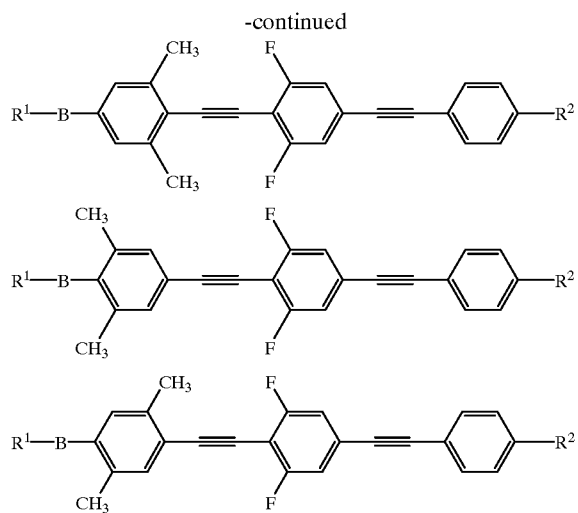

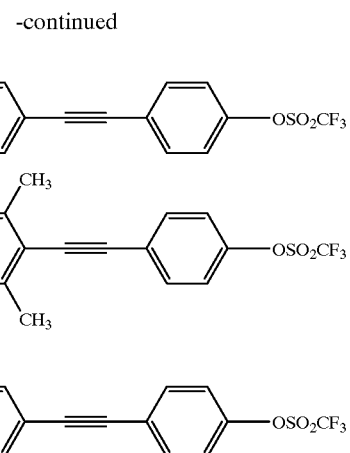

The phenylacetylene compound represented by the formula (2A) of the present invention may be synthesized through ordinary organic synthesizing processes, for example, through combination of the reactions described in "Organic Synthesis Developed by Transition Metals" Jiro Tsuji, published by Kagaku Dojin Co. A specific example of the preparation process involves reacting compounds represented by the formulae (IM-5) and (IM-6) in the presence of a palladium catalyst and a base such as triethyl amine:

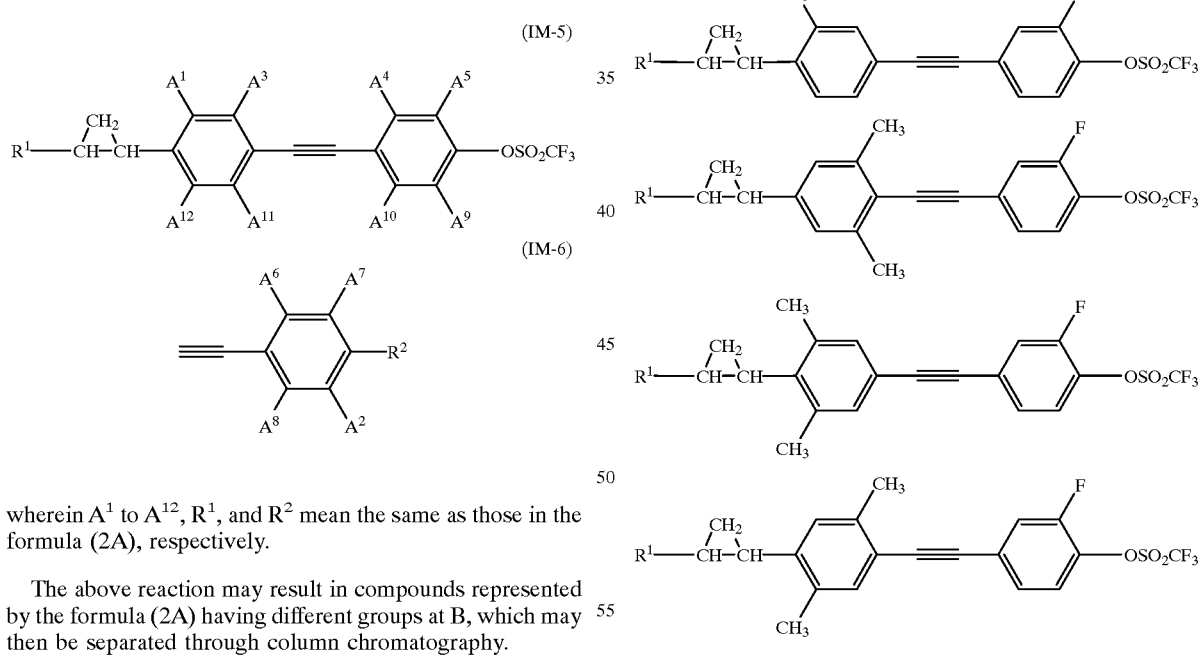

wherein $A^1$ to $A^{12}$, $R^1$, and $R^2$ mean the same as those in the formula (2A), respectively.

The above reaction may result in compounds represented by the formula (2A) having different groups at B, which may then be separated through column chromatography.

Examples of the compound represented by the formula (IM-5) include compounds represented by the following formulae:

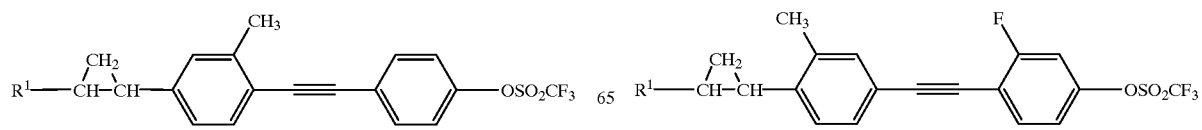

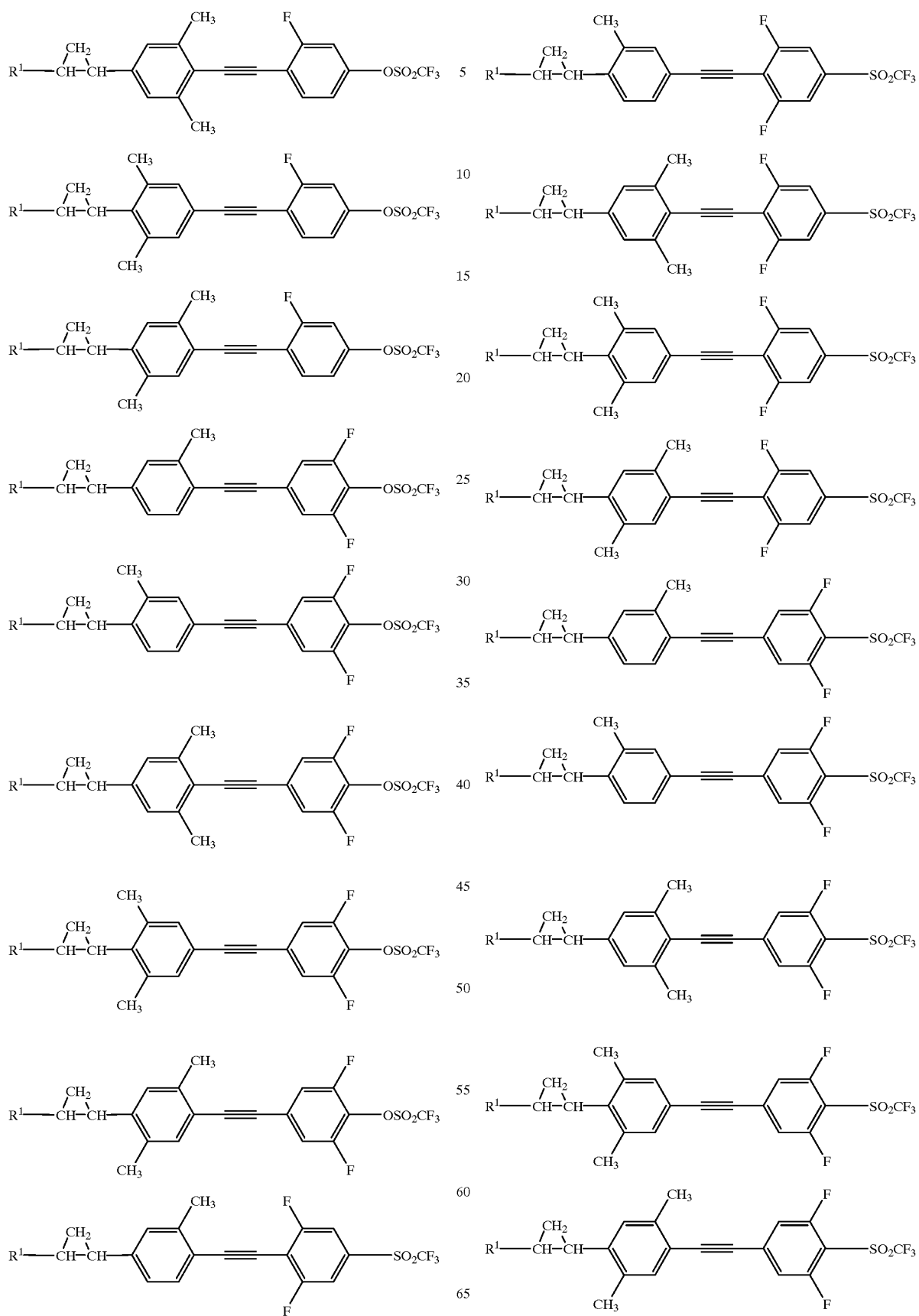

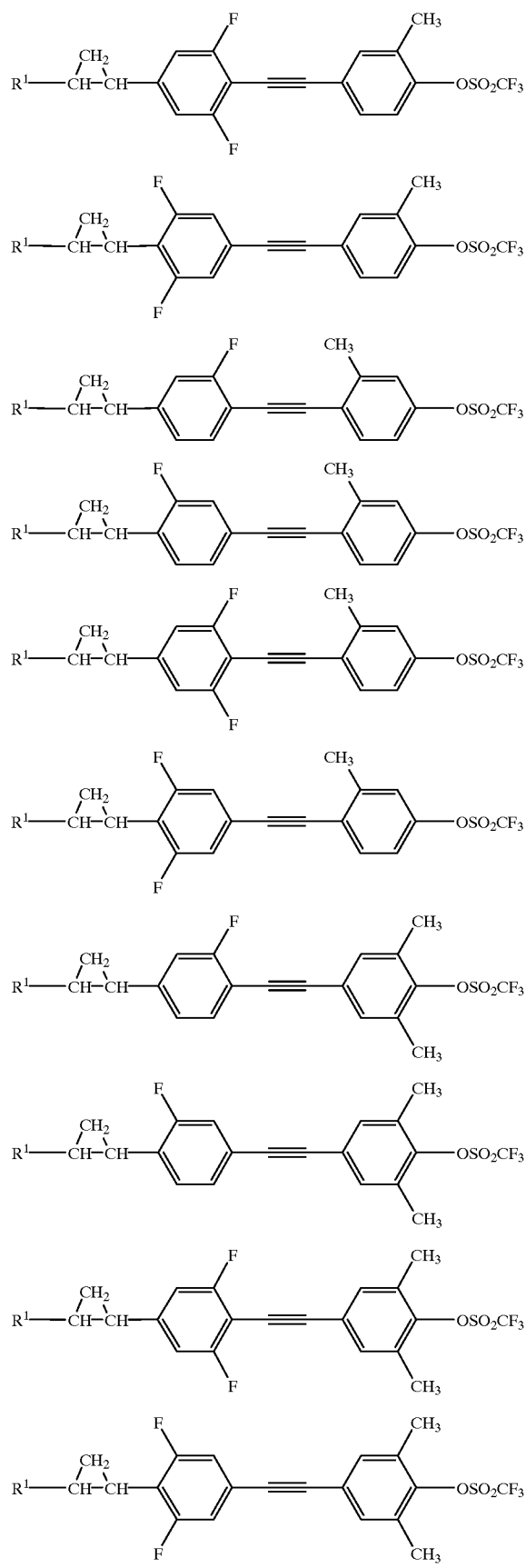
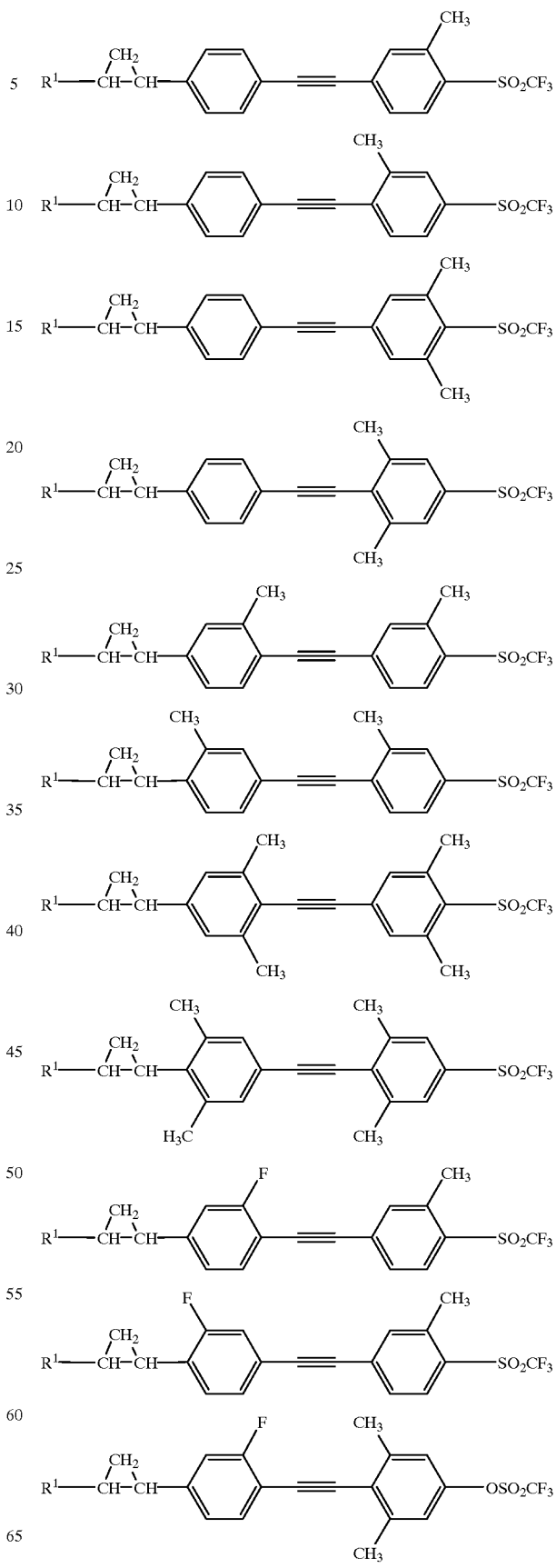

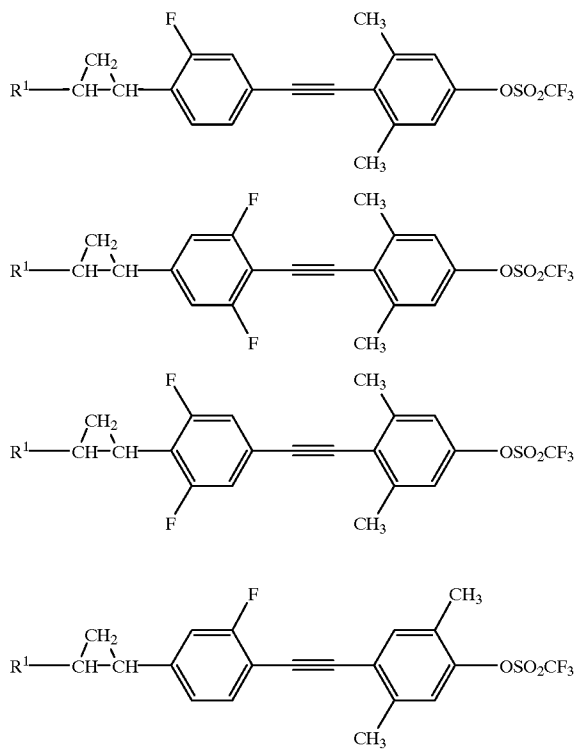
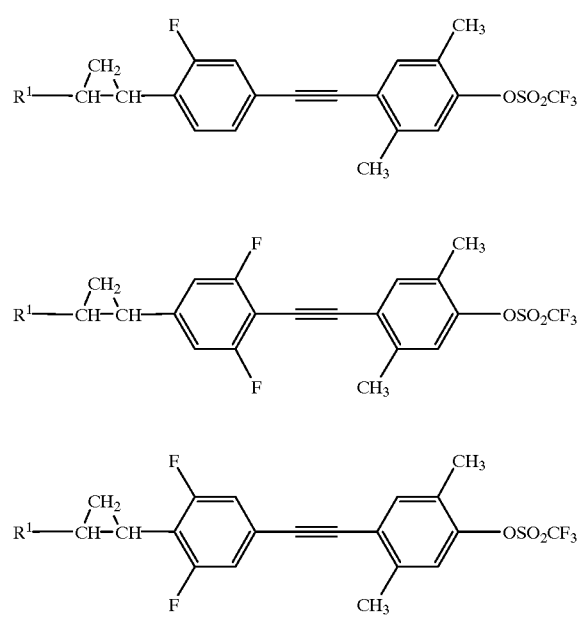
The compound represented by the formula (IM-5) may be prepared through the following route:
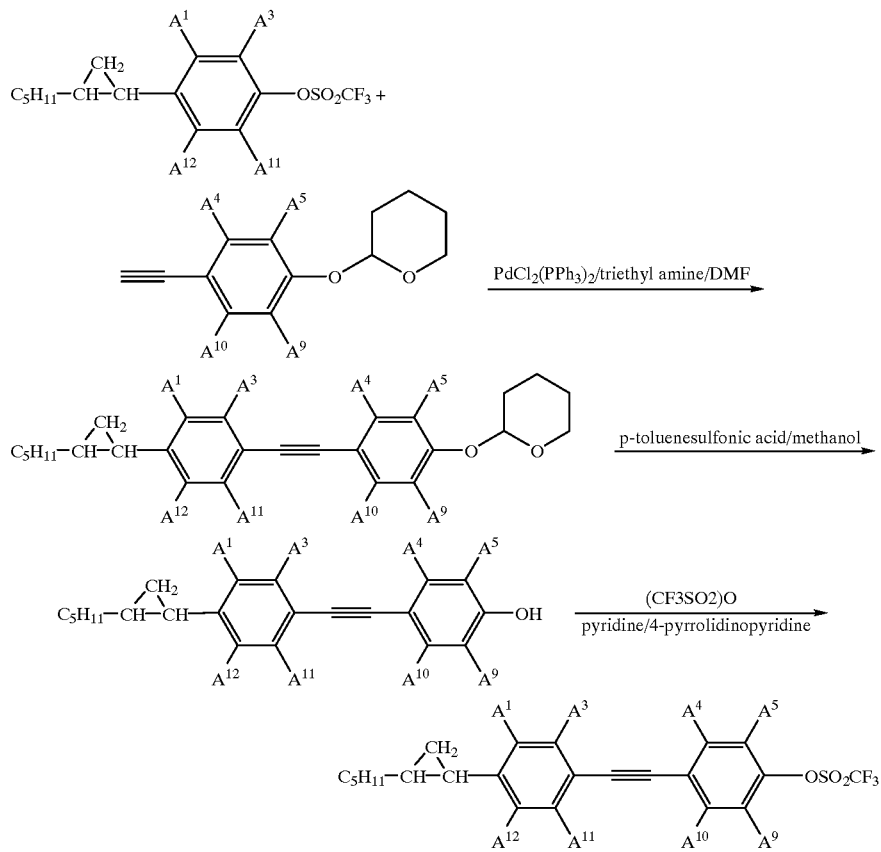

In the above compounds, $A^1$, $A^3$ to $A^5$, $A^9$ to $A^{12}$, and $R^1$ mean the same as those in the formula (2A).

In the reaction of the compounds represented by the formulae (IM-5) and (IM-6) for preparing the phenylacetylene compound represented by the formula (2A), the amount of the compound (IM-6) used is usually an equivalent of 0.3 to 10 times, preferably 0.5 to 2 times the amount of the compound (IM-5).

The palladium catalyst used in the above reaction may be selected from those listed for the reaction of the compounds (IM-1) and (IM-2). The amount of the palladium catalyst is usually an equivalent of 0.0001 to 1 time, preferably 0.001 to 0.1 times the amount of the compound (IM-6).

The base used for this reaction may be selected from those listed for the reaction of the compounds (IM-1) and (IM-2). The amount of the base is usually an equivalent of 1 to 100 times, preferably 1 to 20 times the amount of the compound (IM-6).

The temperature of the reaction is usually −20 to 200° C., preferably 30 to 150° C. A solvent may optionally be used as desired, such as acetonitrile, tetrahydrofuran, dimethylformamide, hexamethylphosphorylamide, N-methylpyrrolidone, N,N-dimethylimidazolidinone, benzene, or toluene. The amount of the solvent is not particularly limited, and may be selected suitably.

One liquid crystal composition of the present invention contains at least one phenylacetylene compound represented by the formula (1A) or (2A) as a component. Other components of the composition are not particularly limited, but compounds that exhibit a liquid crystal phase or compositions thereof may preferably be used.

In the liquid crystal composition of the present invention, the content of the phenylacetylene compound represented by the formula (1A) or (2A) is preferably 0.1 to 99.9 wt %, more preferably 1 to 99 wt % of the liquid crystal composition.

The liquid crystal composition of the present invention may contain one or more chiral compounds as a twisting agent. The chiral compounds are not particularly limited, and those to be listed later for another liquid crystal composition of the present invention may be used. The content of the chiral compound is not particularly limited, and may suitably be selected depending on the composition or the like conditions.

The other liquid crystal composition according to the present invention contains at least one benzylidynyl tolan compound represented by the formula (3A), and at least one compound selected from the group consisting of compounds represented by any one of the formulae (3B), (3C), and (3D).

In the formula (3A), $A^1$ to $A^{12}$ each independently stands for a hydrogen atom, a fluorine atom, or an alkyl or alkoxy group having 1 to 10 carbon atoms optionally substituted with at least one fluorine atom. At least one of $A^1$ to $A^{12}$ is an alkyl or alkoxy group having 1 to 10 carbon atoms substituted with at least one fluorine atom. When any of $A^1$ to $A^{12}$ is a fluorine atom, preferably one or two of them are fluorine atoms. $R^1$ and $R^2$ in the formula (3A) mean the same as $R^1$ and $R^2$ in the formula (1A), respectively, and examples of $R^1$ and $R^2$ in the formula (3A) may include those listed as examples of $R^1$ and $R^2$ in the formula (1A).

Examples of the compound represented by the formula (3A) may include compounds represented by the following formulae, wherein $R^1$ and $R^2$ each preferably stands for any of those listed in the above examples, but is not limited thereto:

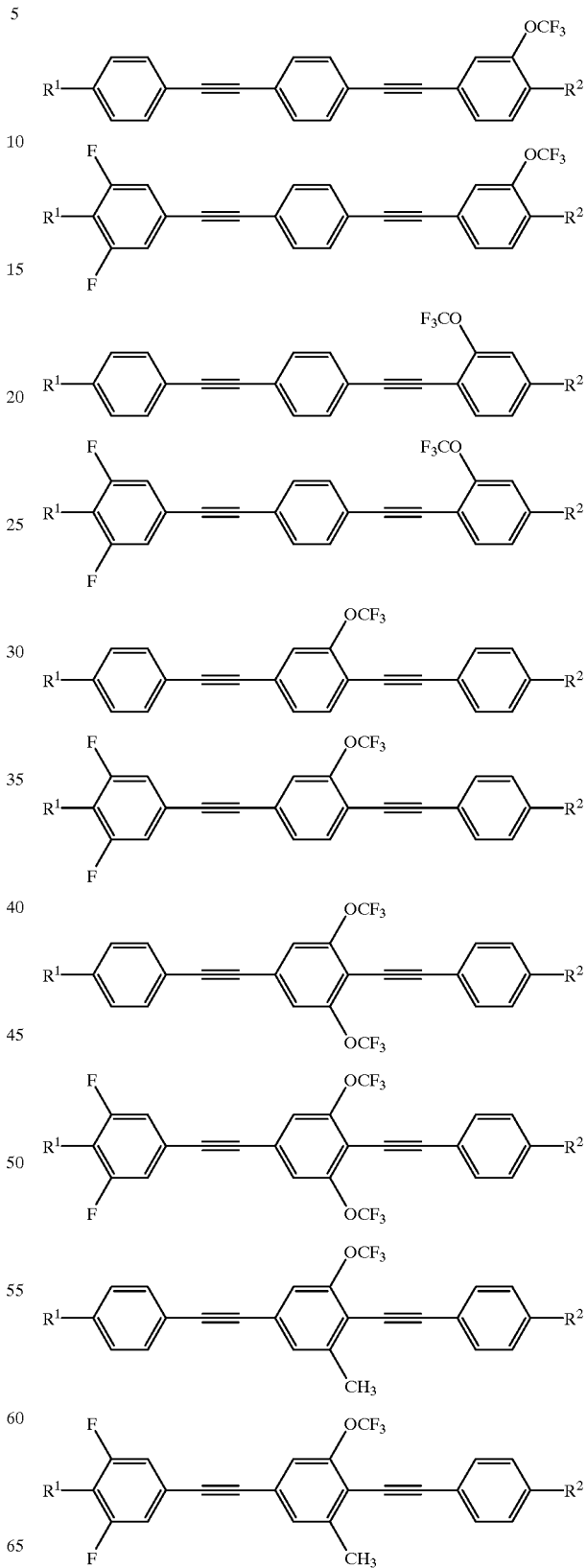

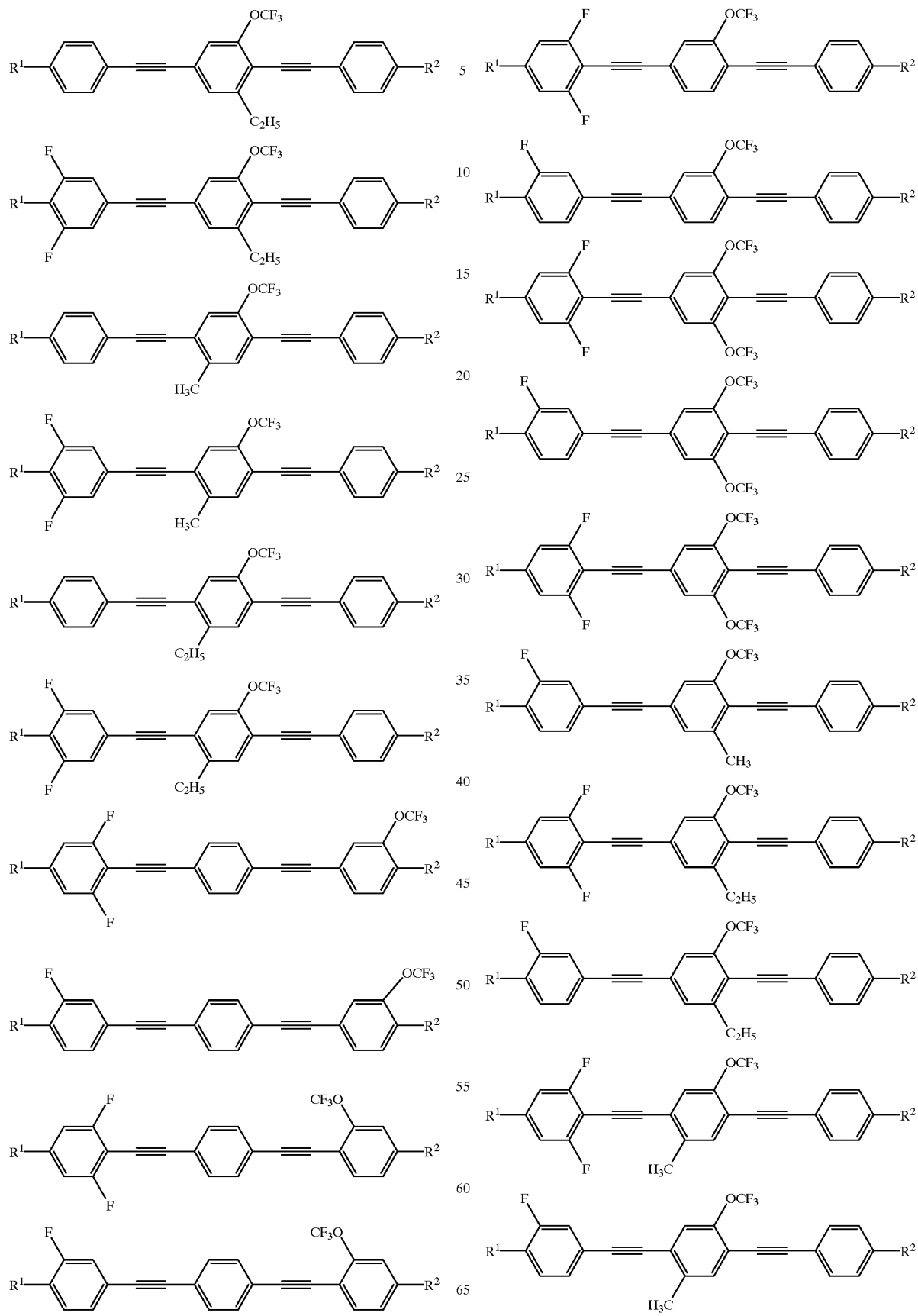

-continued
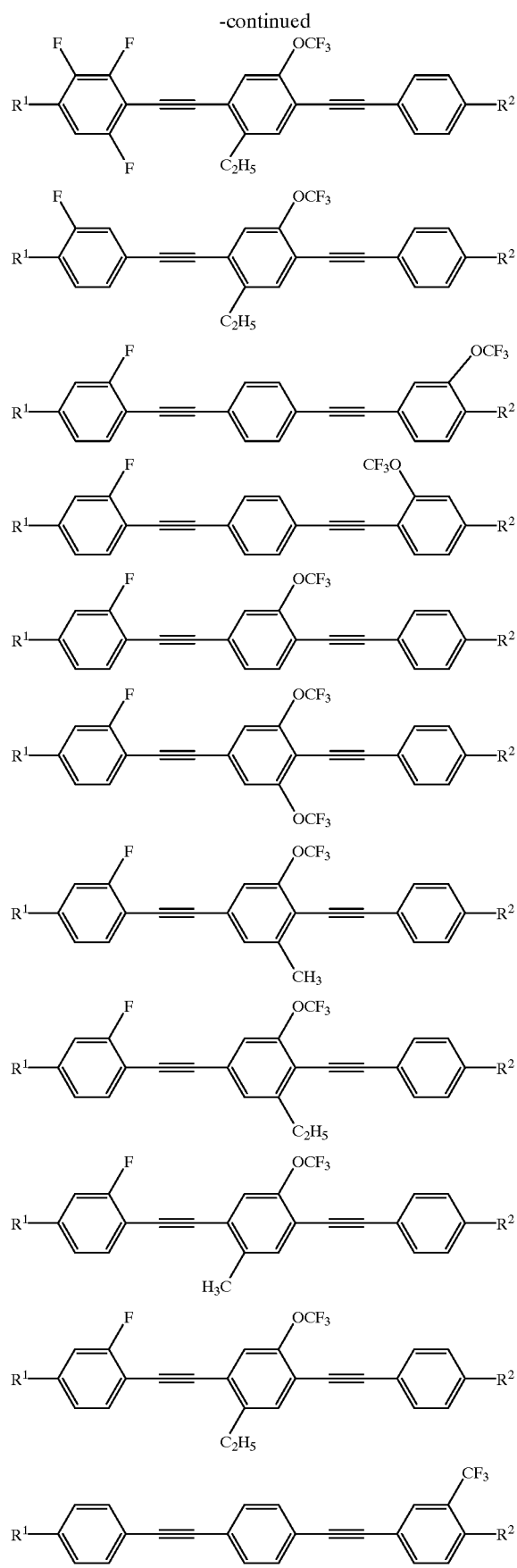
-continued
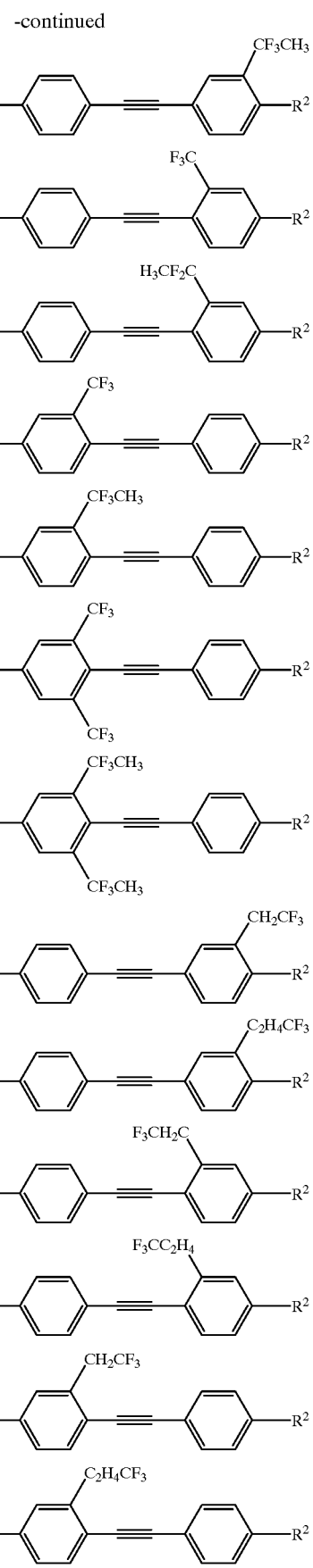

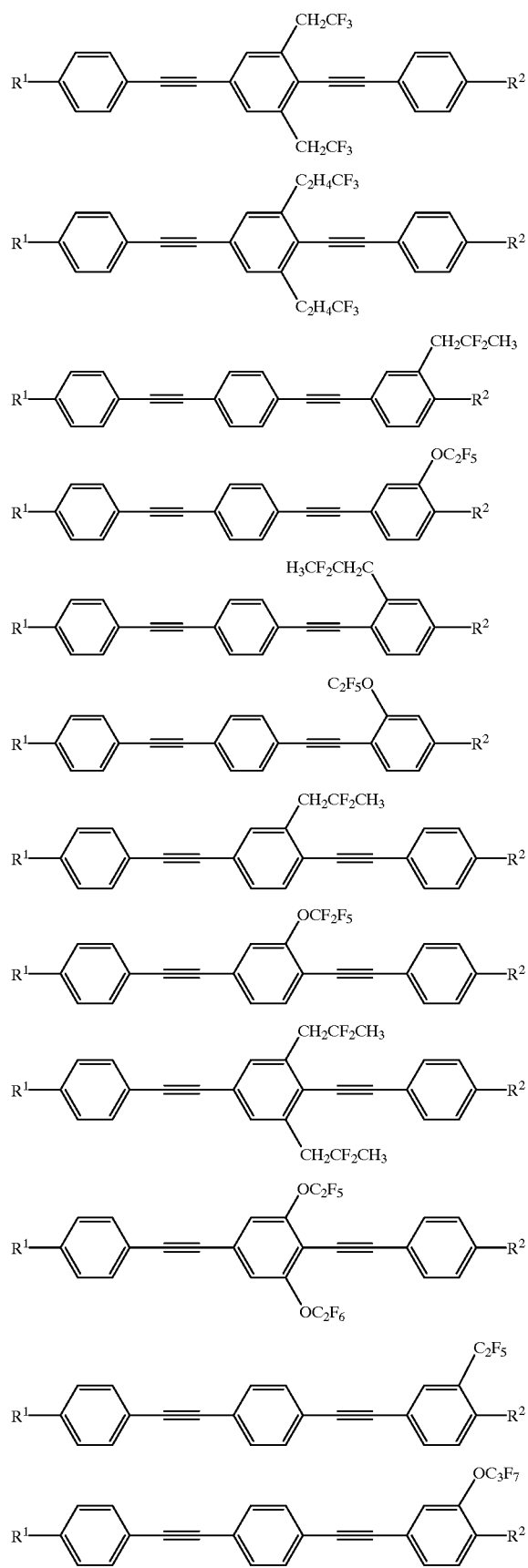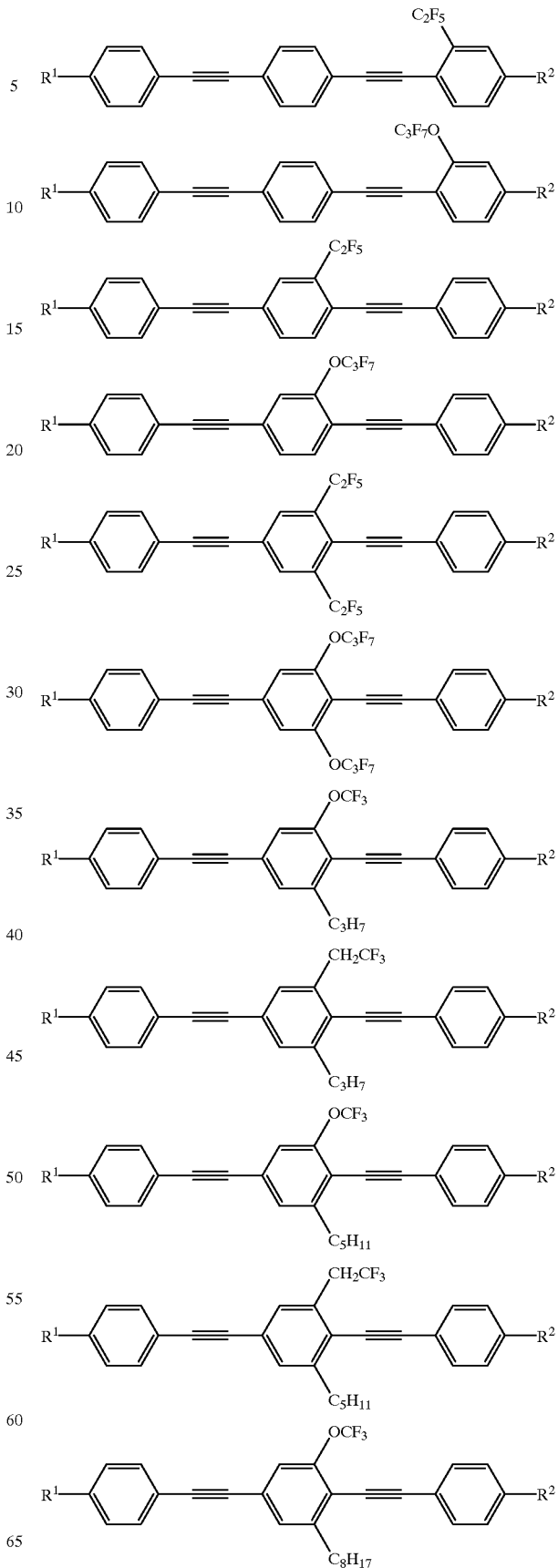

-continued

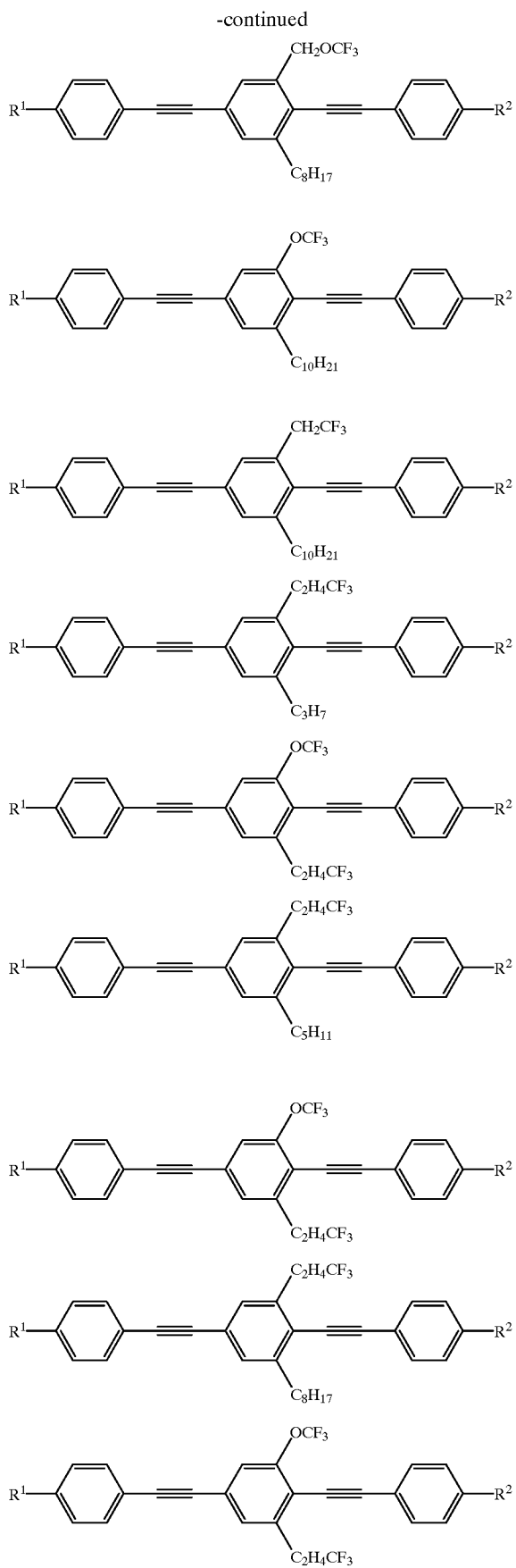

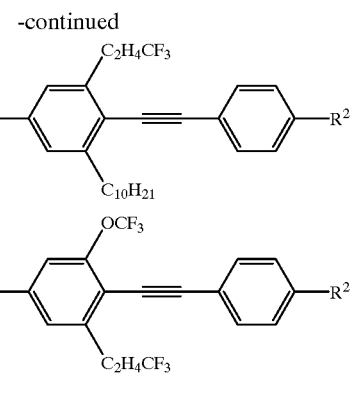

The compound represented by the formula (3A) may be synthesized through ordinary organic synthesizing processes, for example, through combination of the reactions described in "Organic Synthesis Developed by Transition Metals" Jiro Tsuji, published by Kagaku Dojin Co. A specific example of the preparation process involves reacting compounds represented by the formulae (11) and (12) in the presence of copper iodide, a palladium catalyst, and a base such as triethyl amine:

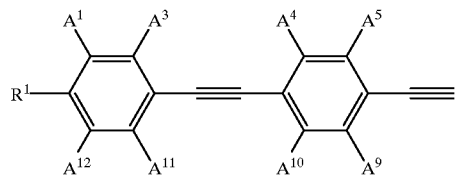

wherein $A^1$ to $A^{12}$, $R^1$, and $R^2$ mean the same as those in the formula (3A), respectively.

The compound represented by the formula (11) may be prepared, for example, by coupling compounds represented by the formulae (13) and (14), followed by reaction with butyl-2-ol in the presence of copper iodide, a palladium catalyst, and a base such as triethyl amine, and then in the presence of a base such as potassium hydroxide:

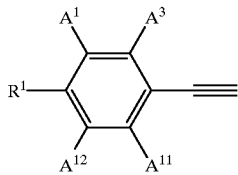

-continued (14)

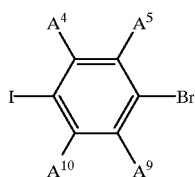

wherein $A^1$, $A^3$ to $A^5$, $A^9$ to $A^{12}$, and $R^1$ mean the same as those in the formula (3A), respectively.

The compound represented by the formula (3A) may alternatively be prepared, for example, by reacting a compound represented by the formula (15) with trifluoromethanesulfonic acid anhydride to substitute the terminal OH group with —$OSO_2CF_3$, followed by reaction with a compound represented by the formula (16) in the presence of copper iodide, a palladium catalyst, and a base such as triethyl amine. In the formulae (15) and (16), $A^1$ to $A^{12}$, $R^1$, and $R^2$ mean the same as those in the formula (3A).

(15)

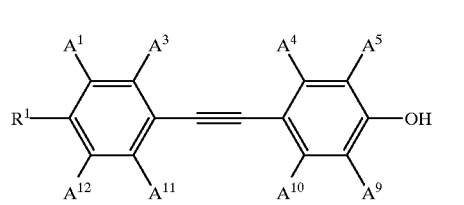

(16)

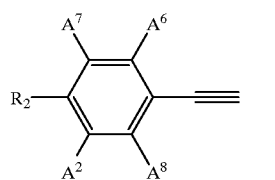

In the formula (3B), $A^{13}$ to $A^{24}$ each independently stands for a hydrogen atom, a fluorine atom, or an alkyl group having 1 to 10 carbon atoms. m is 0 or 1. $R^1$ stands for a hydrogen atom or a straight or branched alkyl group having 1 to 12 carbon atoms optionally substituted with at least one fluorine atom. $R^2$ stands for $R^1$, a fluorine atom, a cyano group, a 4-$R^{31}$-(cycloalkyl) group, a 4-$R^{31}$-(cycloalkenyl) group, or a $R^{41}$—(O)q group, wherein $R^{31}$ stands for a hydrogen atom or a straight or branched alkyl group having 1 to 12 carbon atoms optionally substituted with at least one fluorine atom, $R^{41}$ stands for a straight or branched alkyl group having 1 to 12 carbon atoms optionally substituted with at least one fluorine atom. q is 0 or 1.

Examples of $R^1$ in the formula (3B) may include a hydrogen atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group.

Examples of $R^2$ in the formula (3B) may include those as listed above as examples of $R^1$; an alkenyl group such as an ethenyl, propenyl, butenyl, pentenyl, hexenyl, heptenyl, octenyl, nonenyl, decenyl, undecenyl, or dodecenyl group, or an alkenyl group substituted with at least one fluorine atom, i.e. a fluoroalkenyl group; an alkynyl group such as a propynyl, butynyl, pentynyl, hexynyl, heptynyl, octynyl, nonynyl, decynyl, or dodecynyl group, or an alkynyl group substituted with at least one fluorine atom, i.e. a fluoroalkynyl group; an alkoxy group such as a methoxy, ethoxy, propoxy, butoxy, pentyloxy, hexyloxy, heptyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms or an ethoxy group having 1 to 5 substituted fluorine atoms; a branched alkyl group such as a 2-methylpropyl, 2-methylbutyl, 3-methylbutyl, or 3-methylpentyl group, or a branched alkyl group substituted with at least one fluorine atom, i.e. a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e. a branched fluoroalkyloxy group; a 4-alkyl-cycloalkyl group such as a 4-methylcyclohexyl, 4-ethylcyclohexyl, 4-propyl-cyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkyl-cycloalkyl group substituted with at least one fluorine atom, i.e. a 4-fluoroalkyl-cycloalkyl group; a 4-alkyl-cycloalkenyl group such as a 4-propylcyclohexenyl or 4-pentylcyclohexenyl group, or a 4-alkyl-cycloalkenyl group substituted with at least one fluorine atom, i.e. a 4-fluoroalkyl-cycloalkenyl group; or a cyano group.

Examples of the compound represented by the formula (3B) may include compounds represented by the following formulae, wherein $R^1$ and $R^2$ each preferably stands for any of those listed above, but not limited thereto:

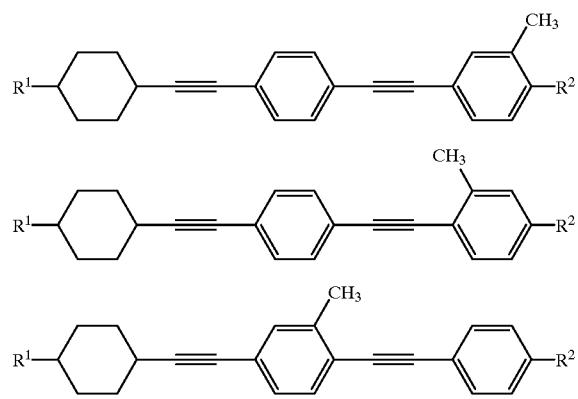

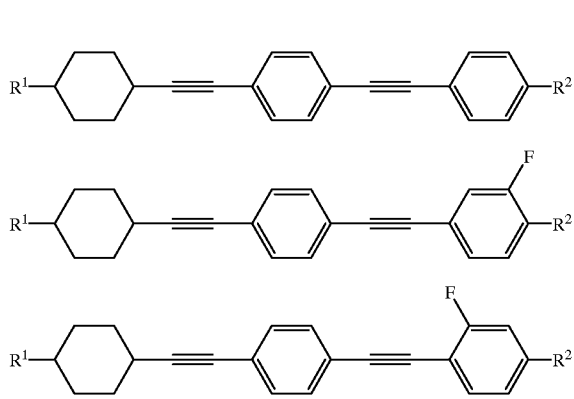

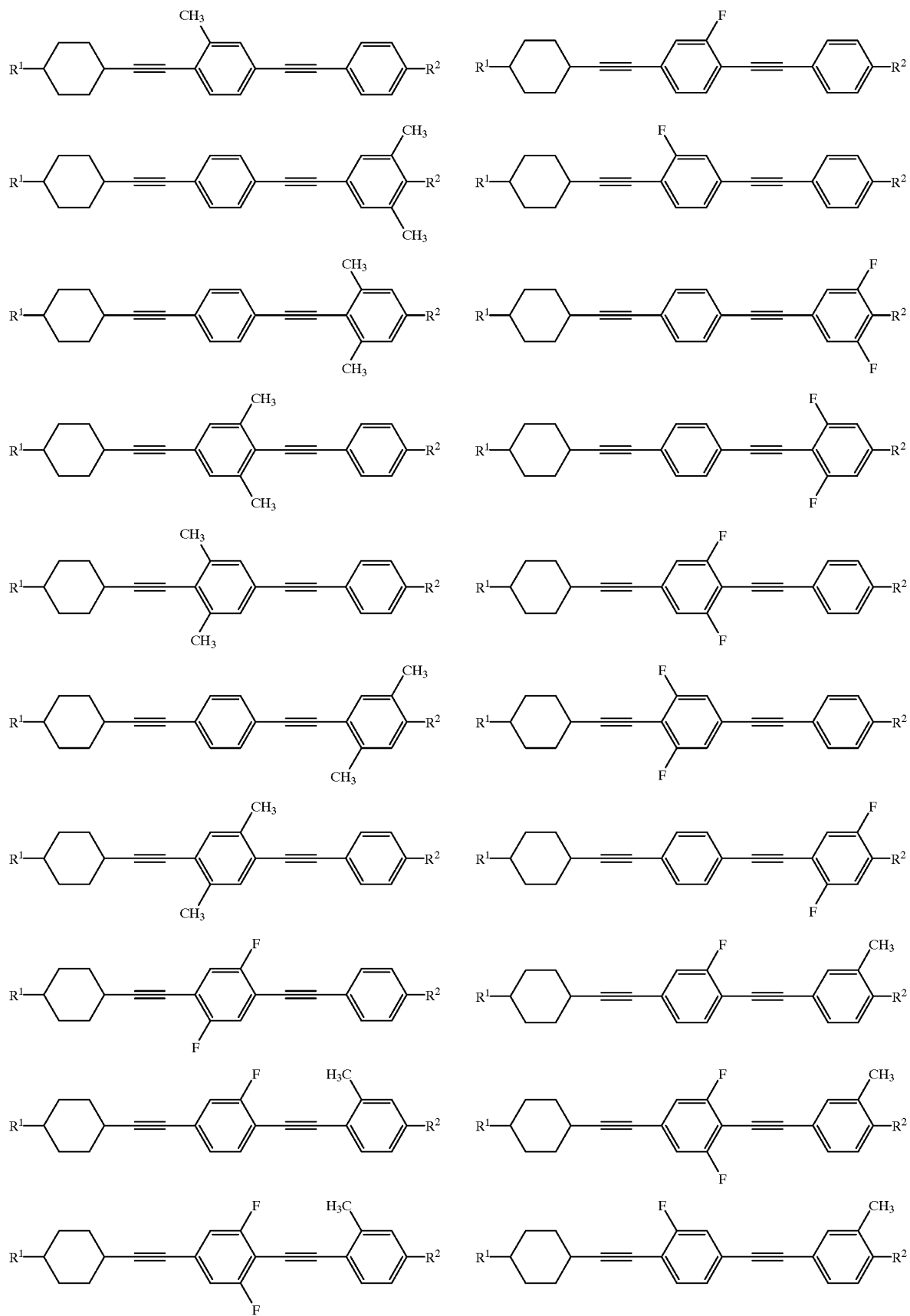

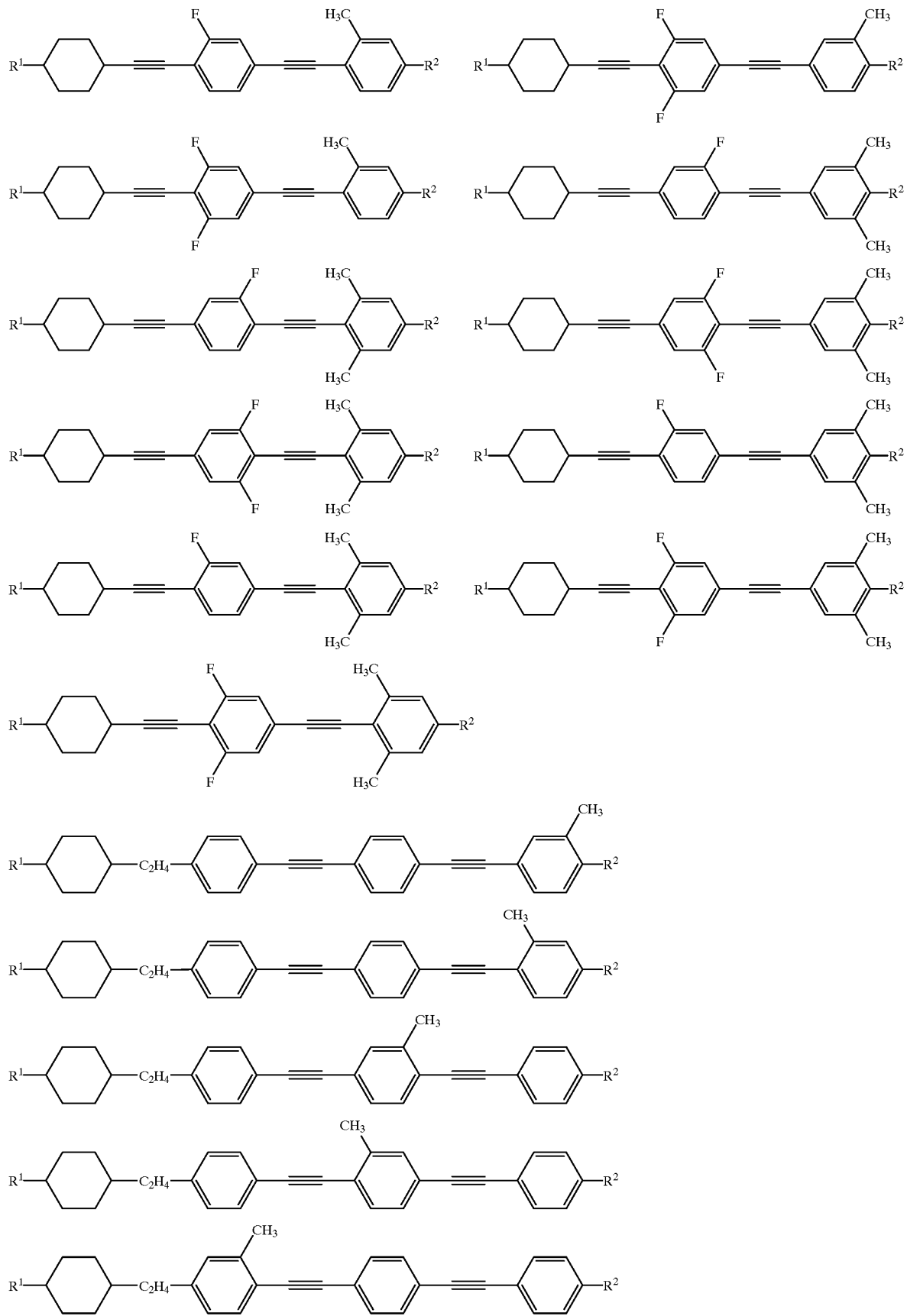

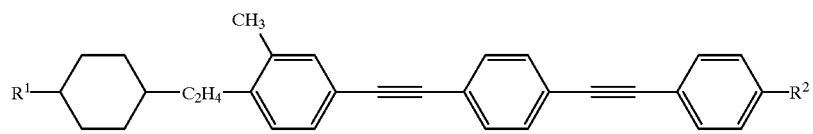
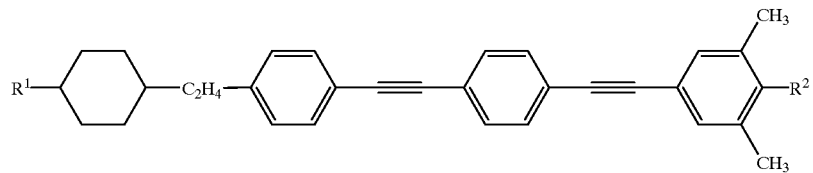
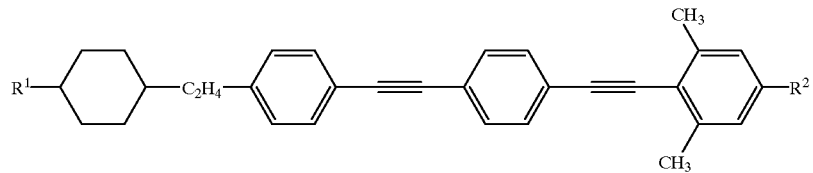
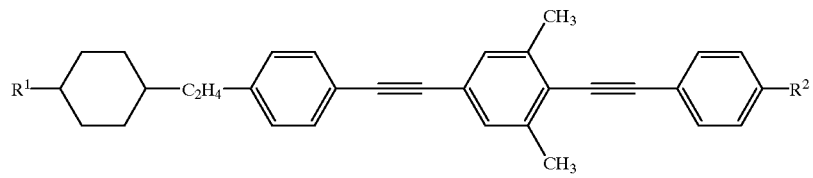
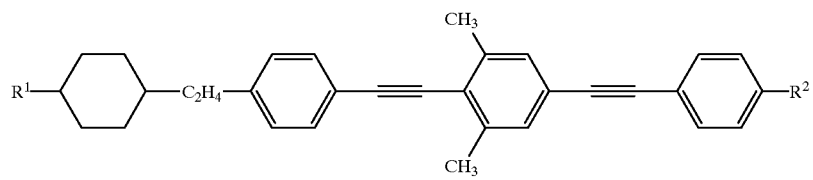
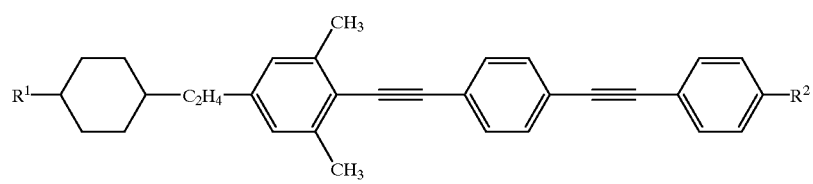
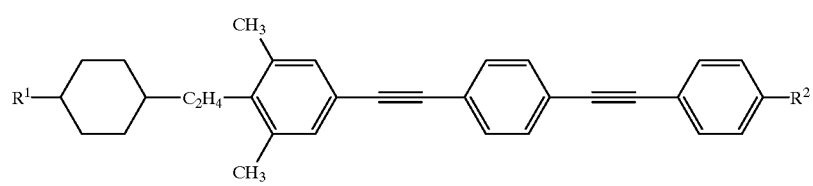
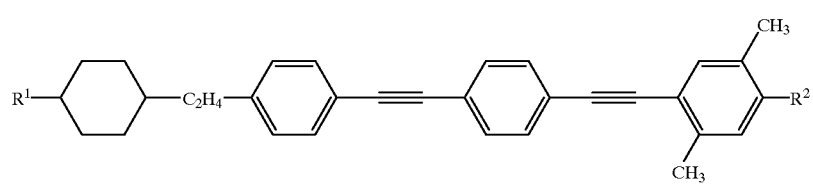
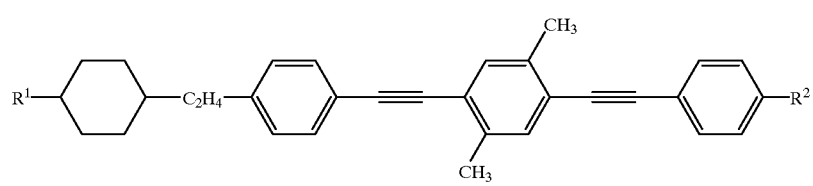

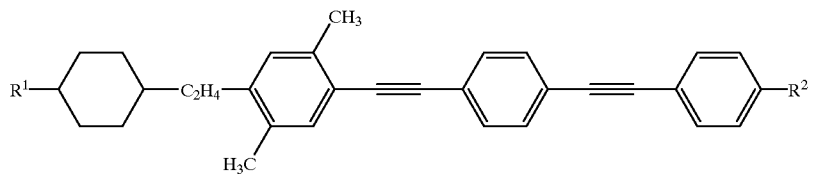
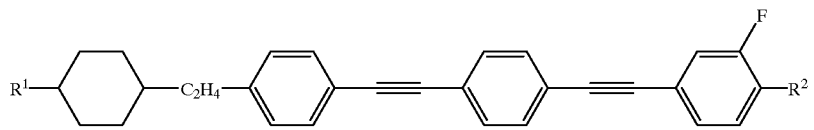
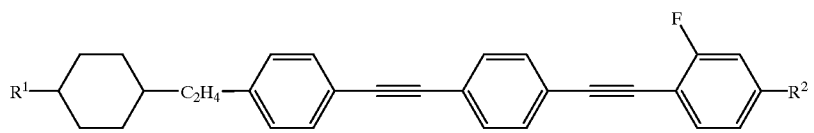
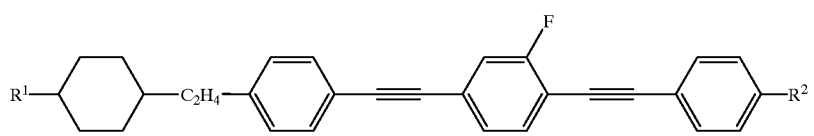
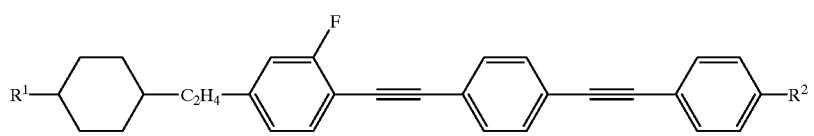
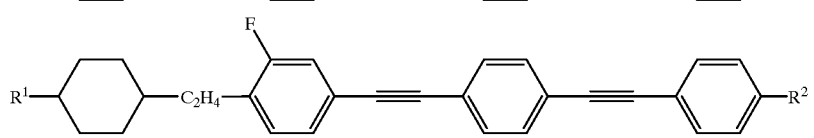
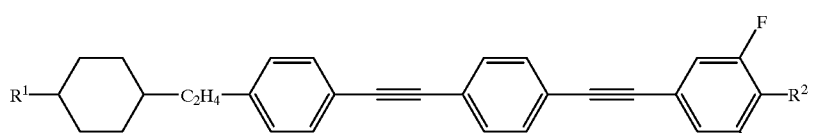
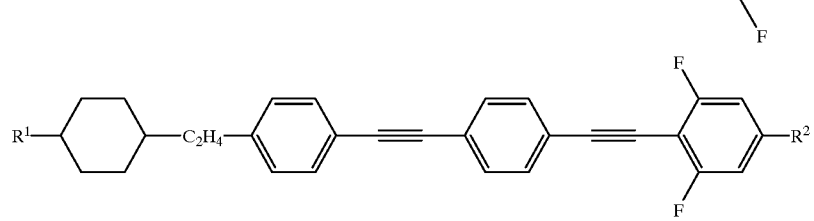
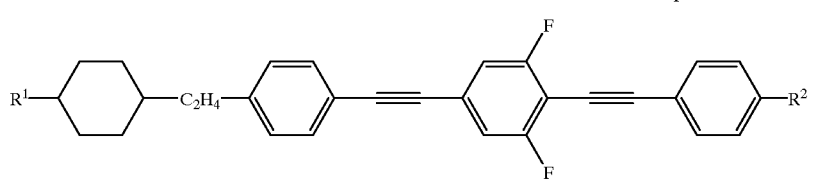
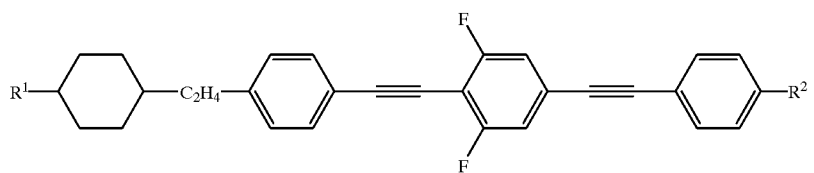
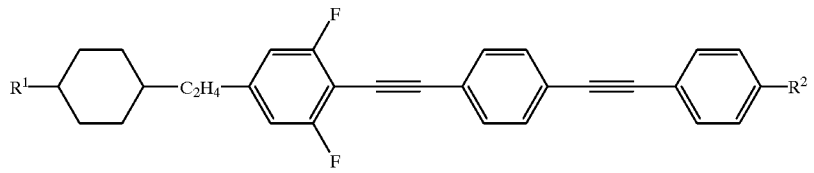

-continued
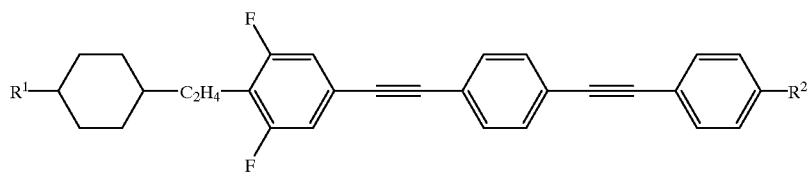
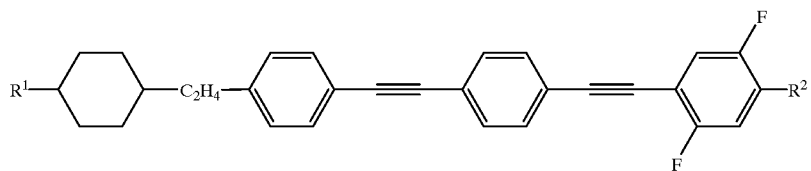
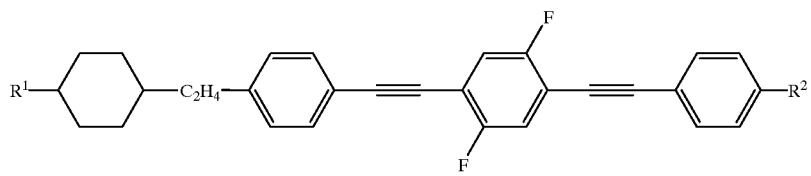
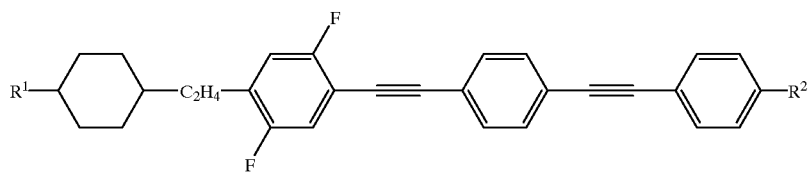
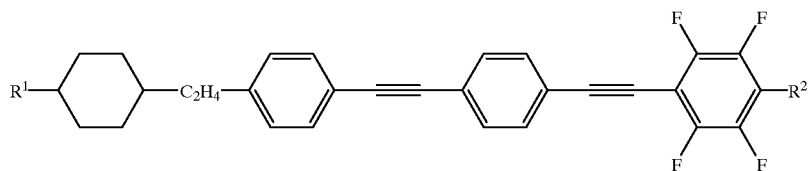
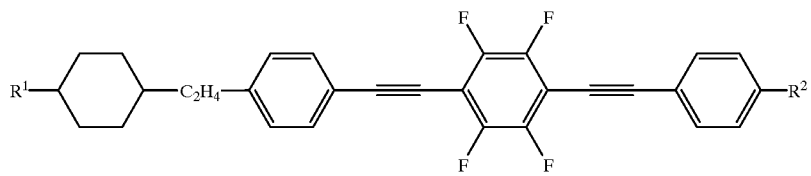
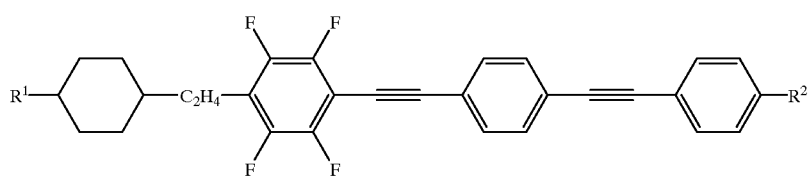
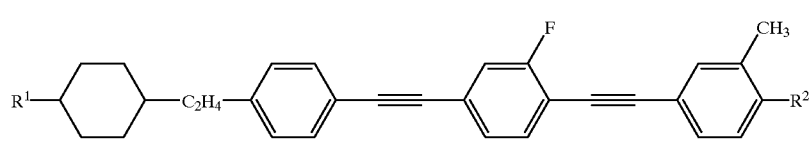
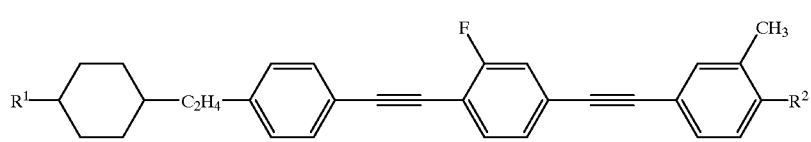
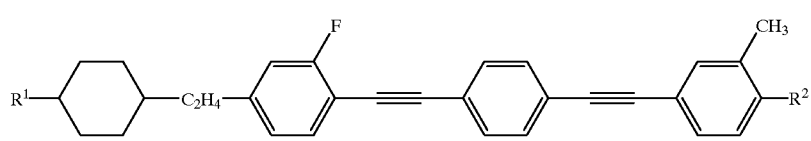

-continued
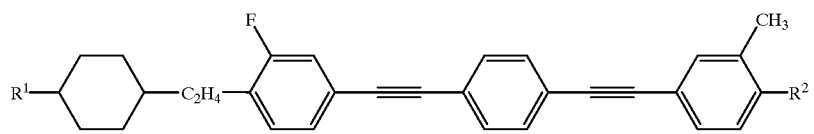
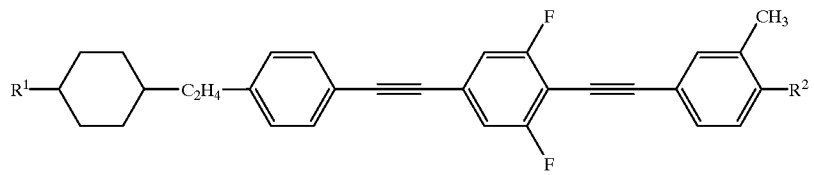
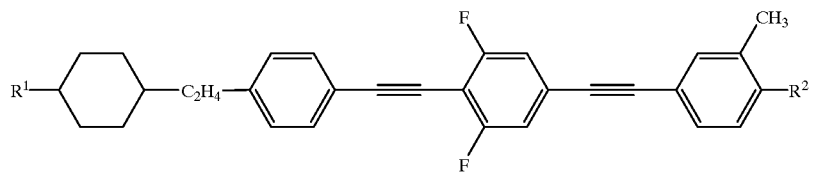
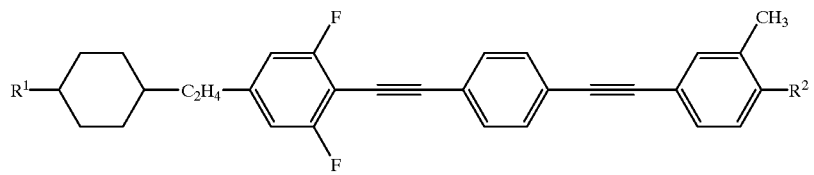
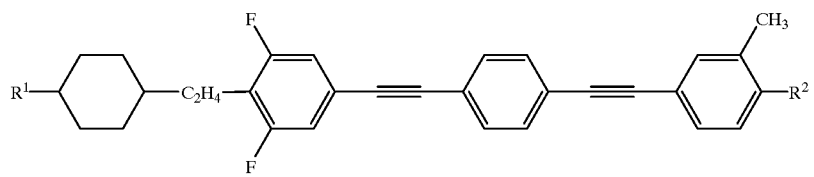
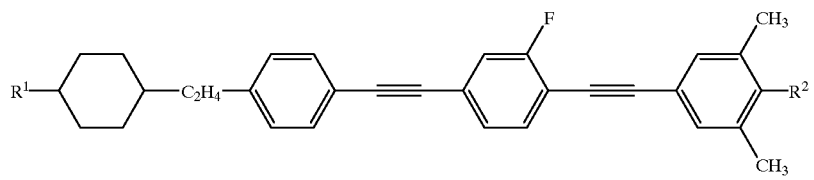
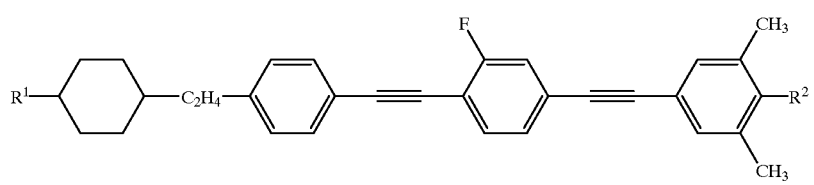
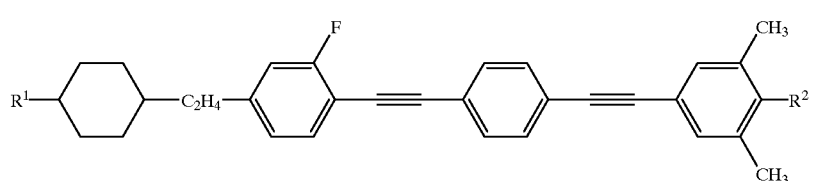
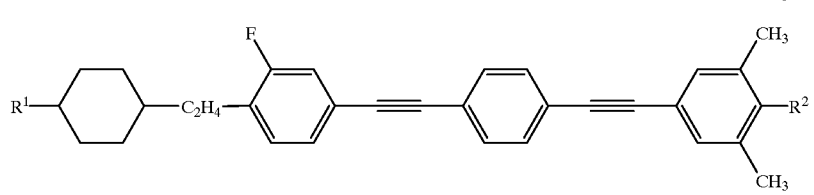

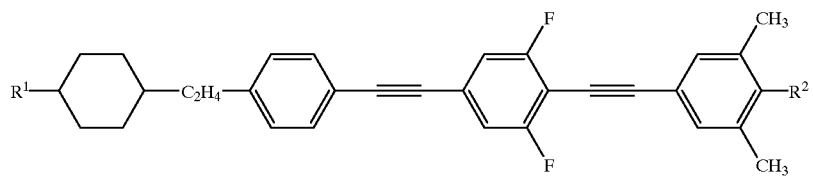
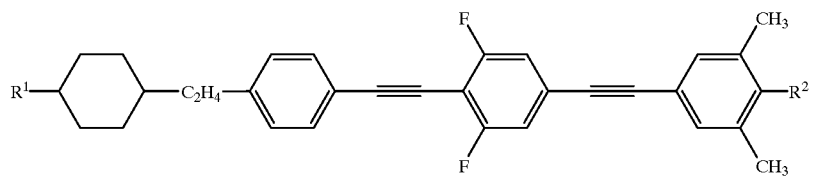
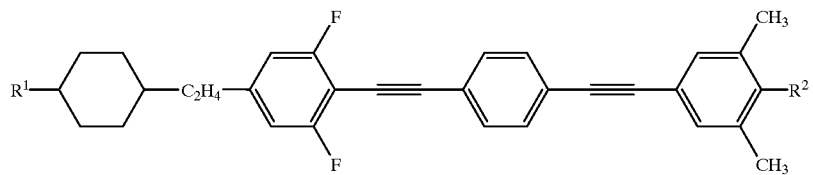
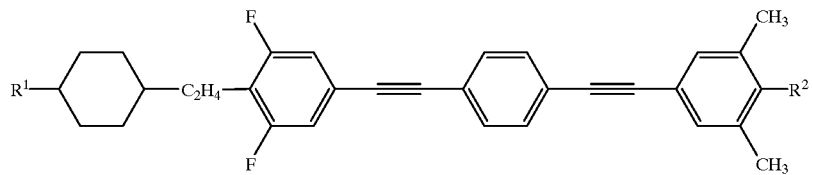
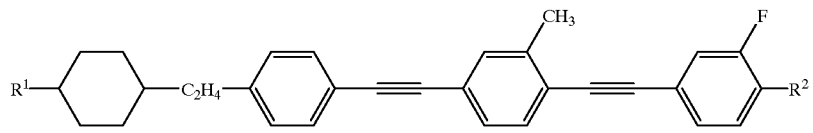
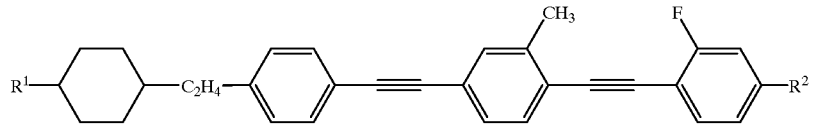
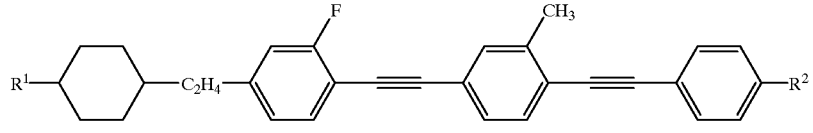
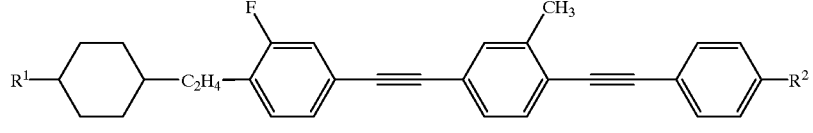
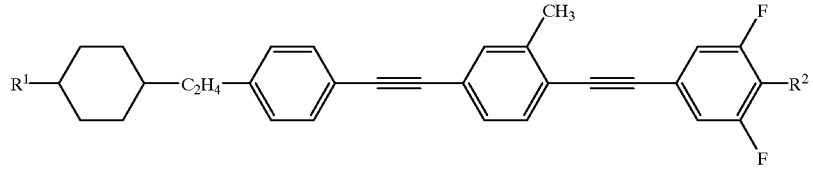
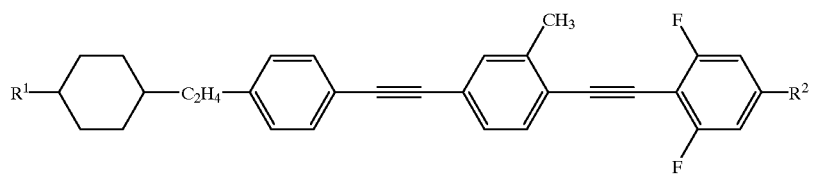

-continued
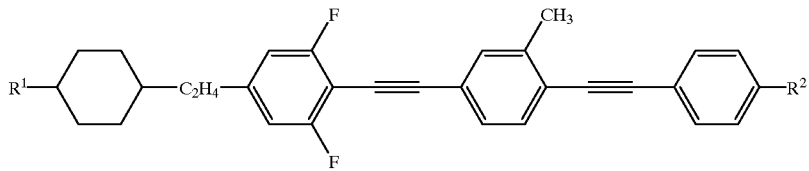
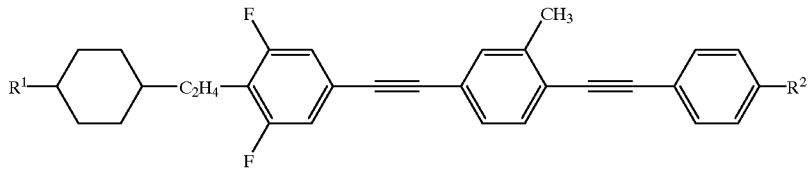
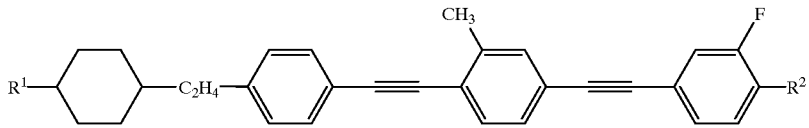
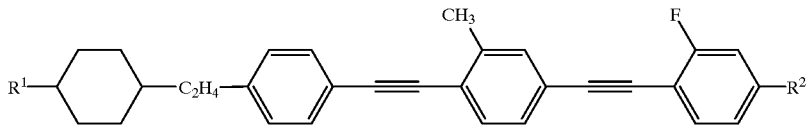
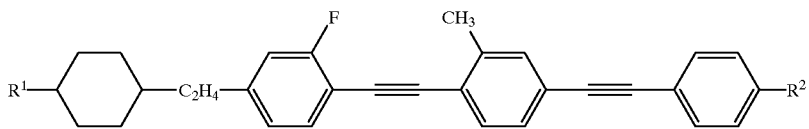
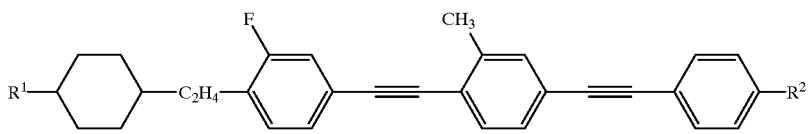
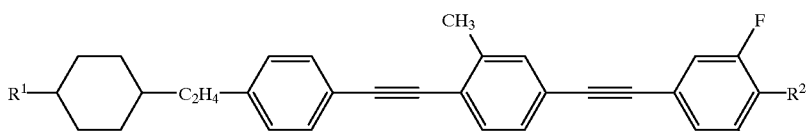
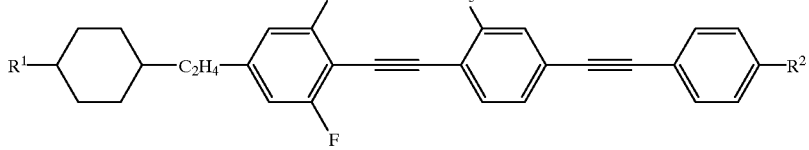
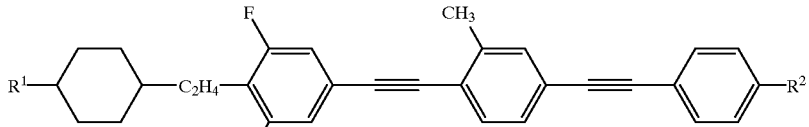
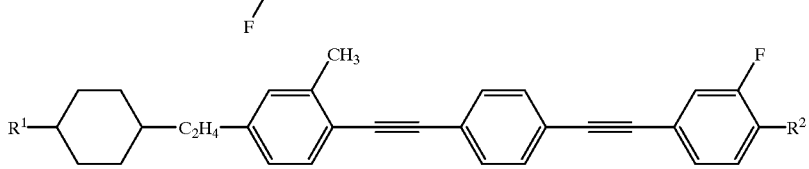

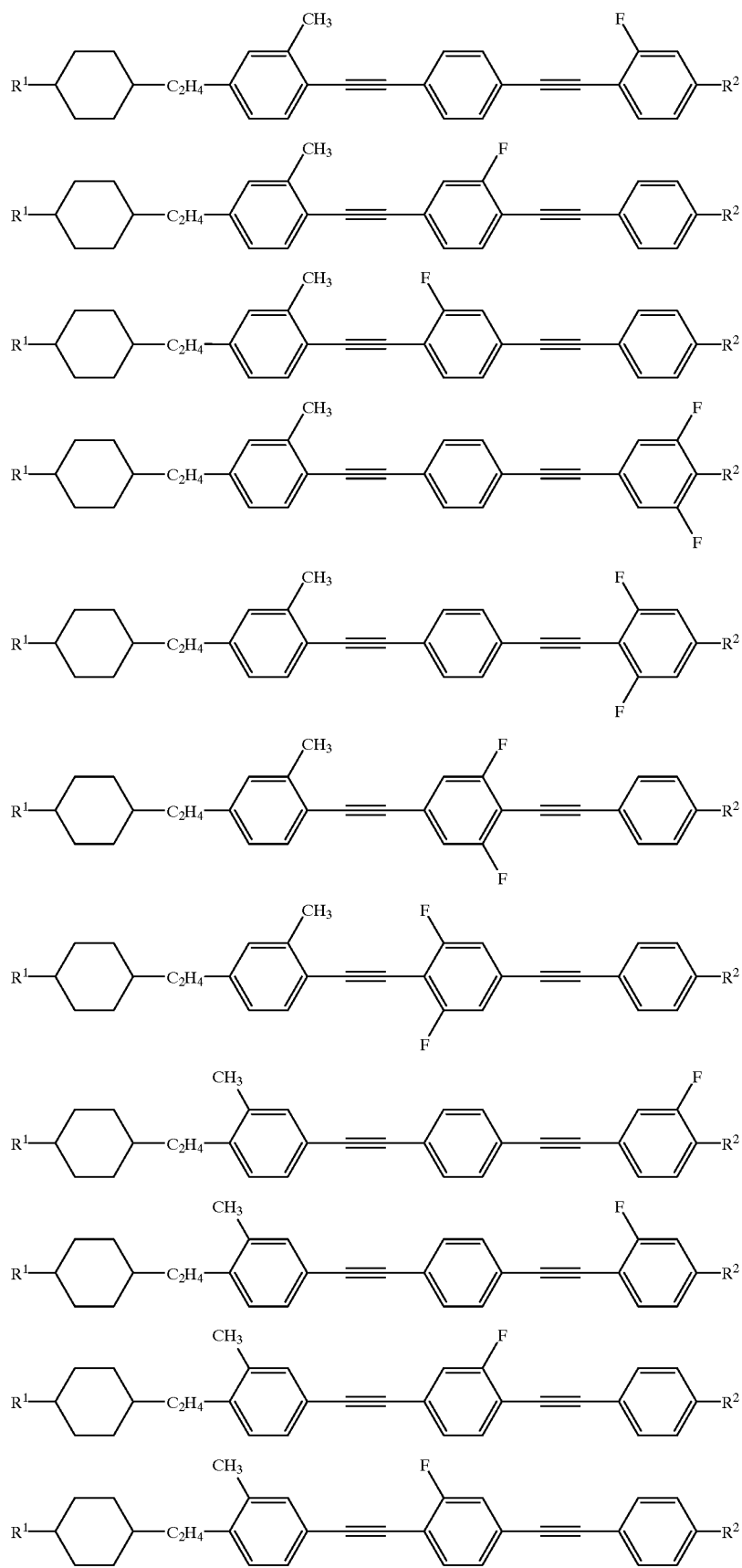

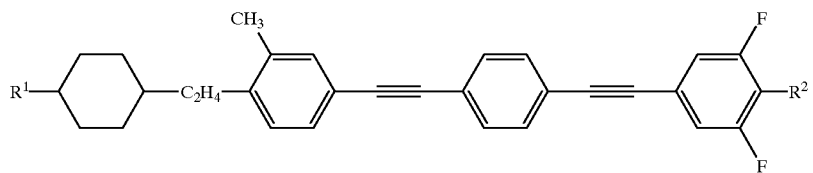
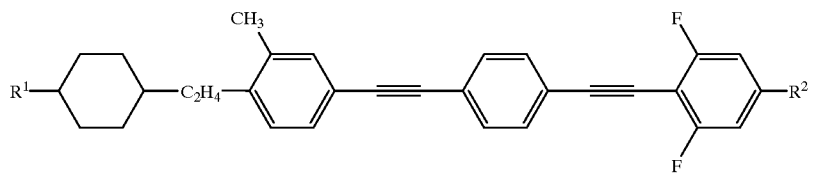
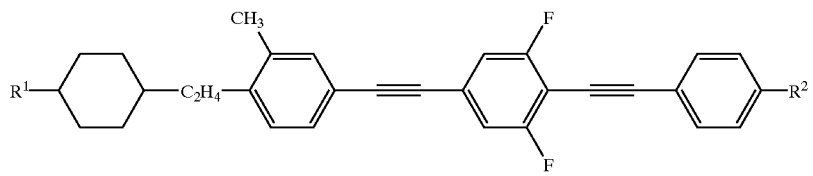
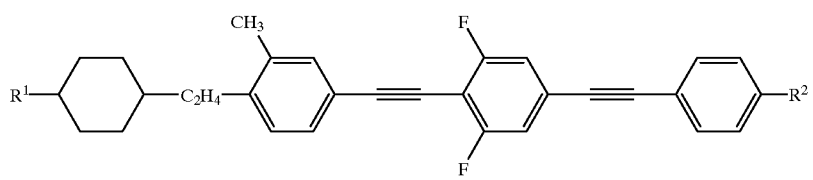
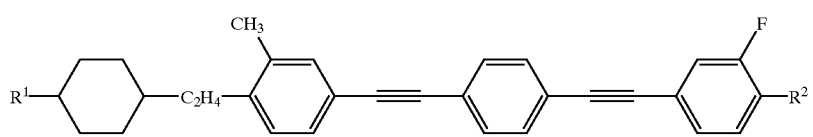
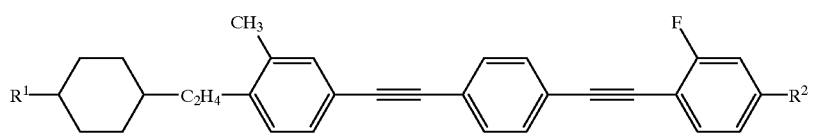
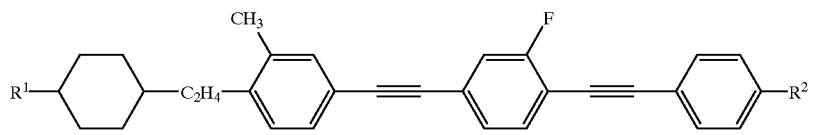
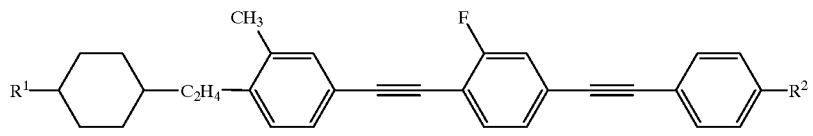
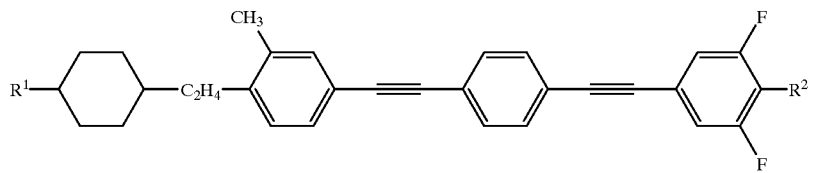
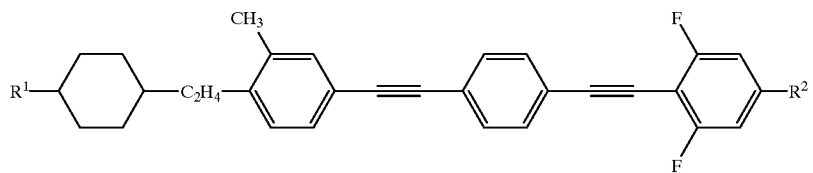

-continued
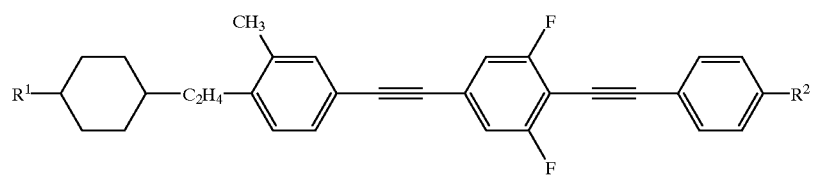
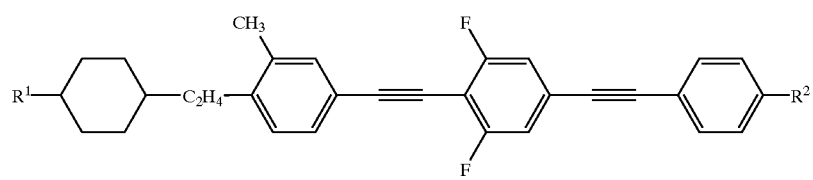
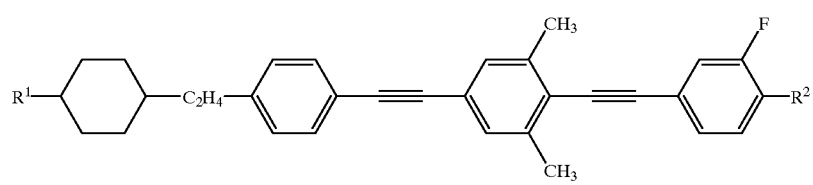
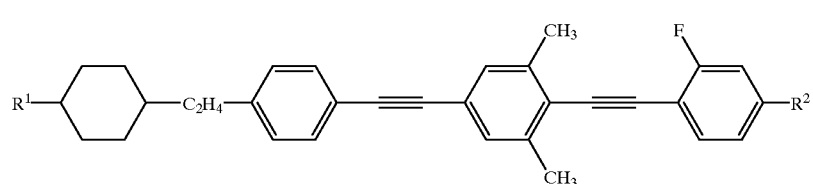
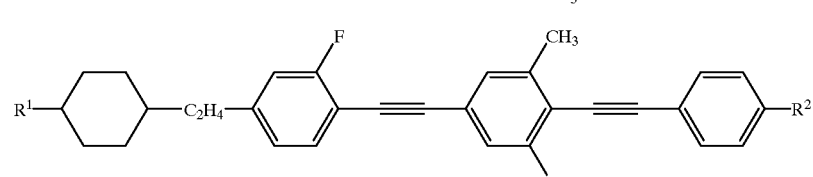
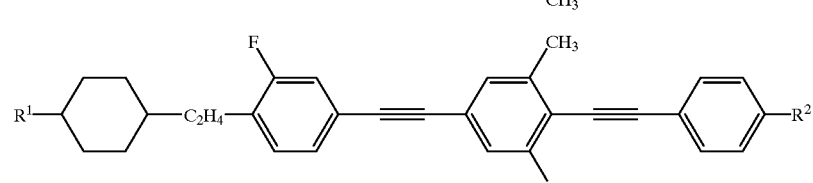
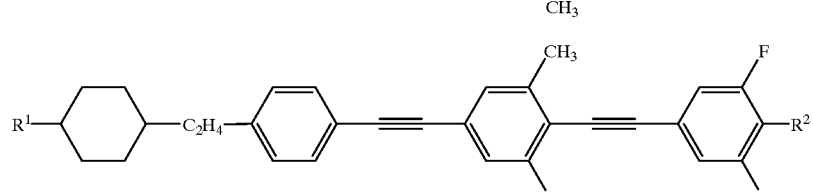
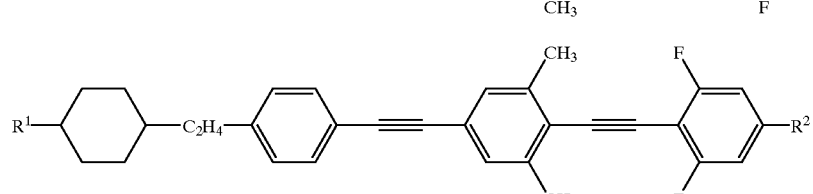
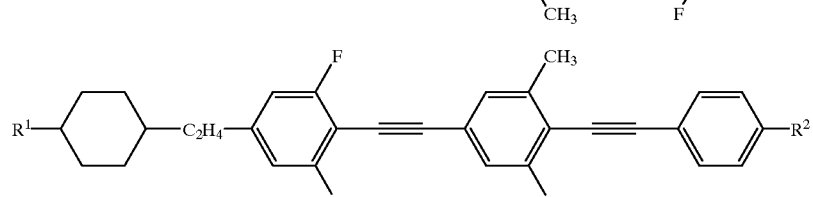

-continued
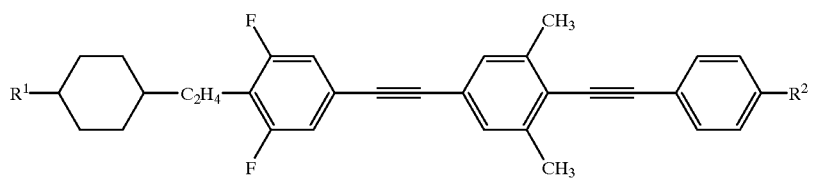
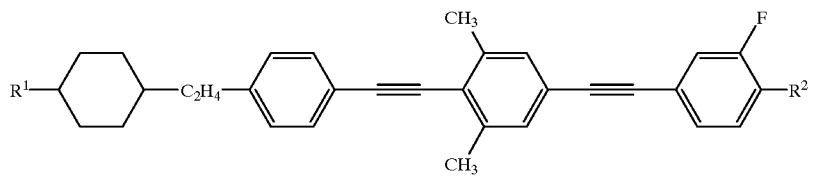
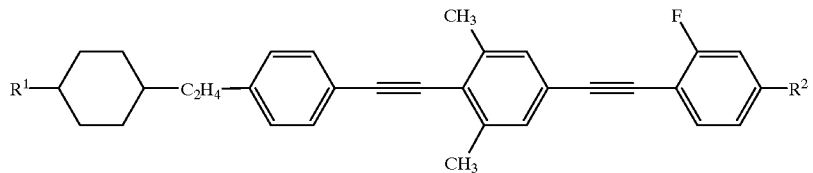
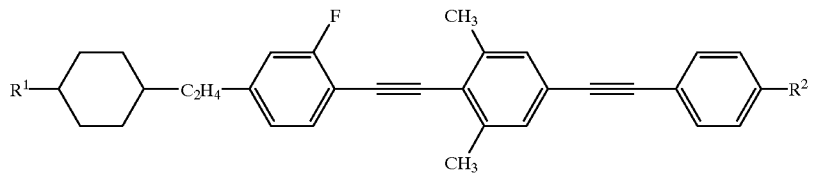
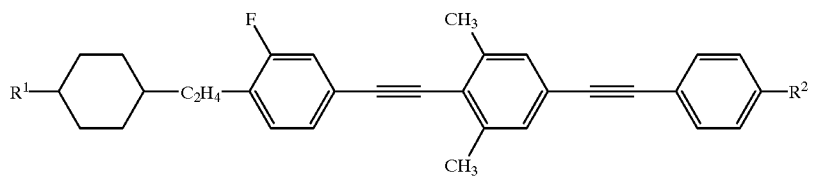
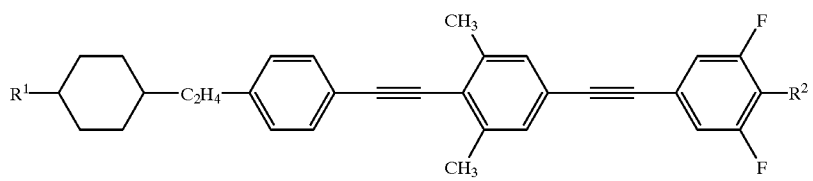
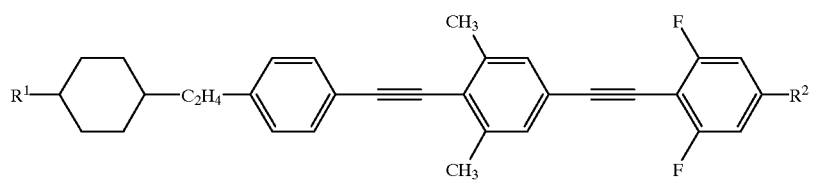
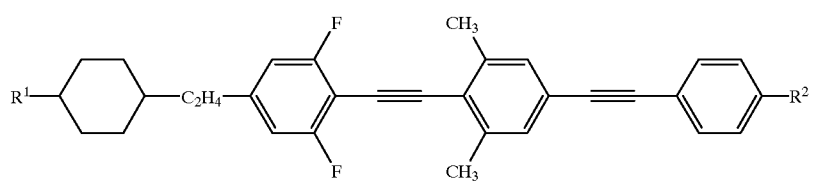
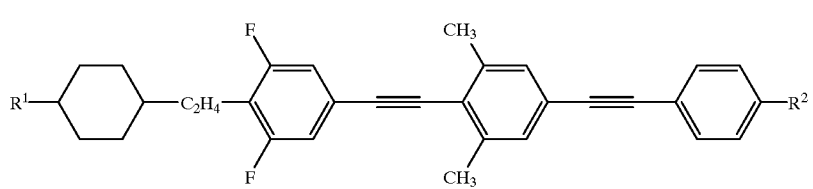

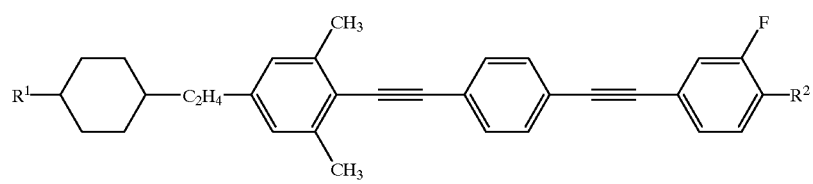
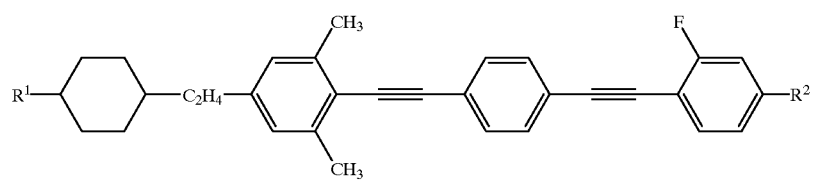
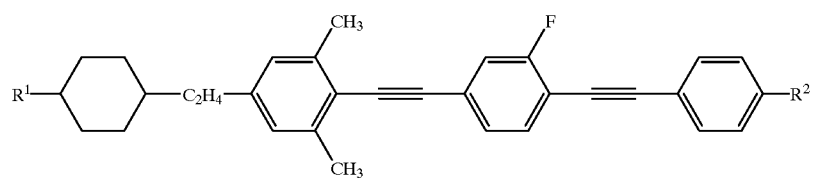
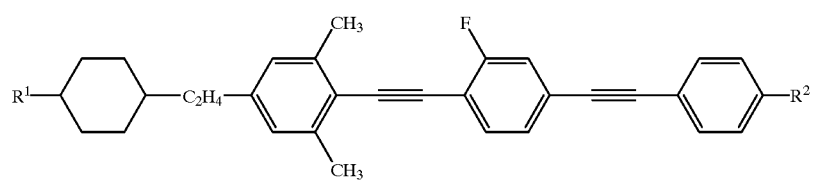
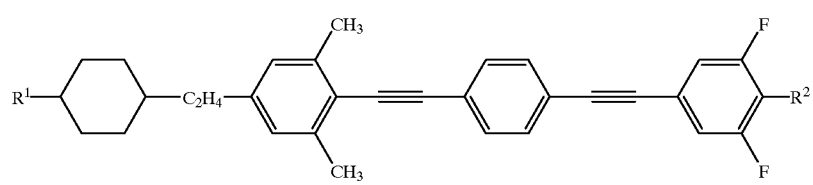
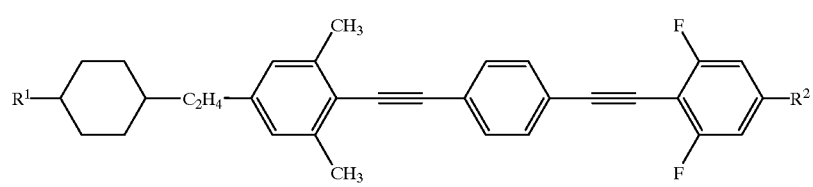
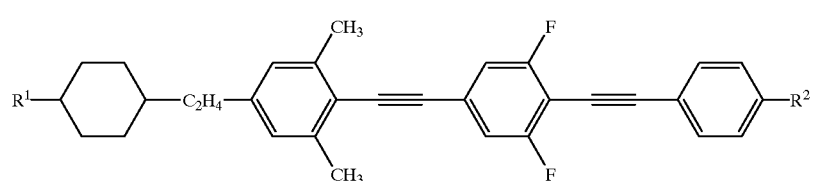
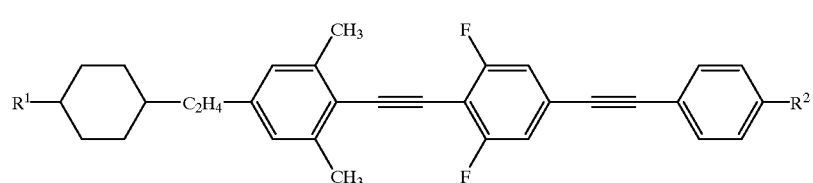
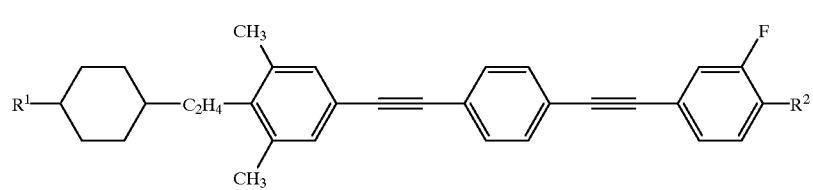

-continued

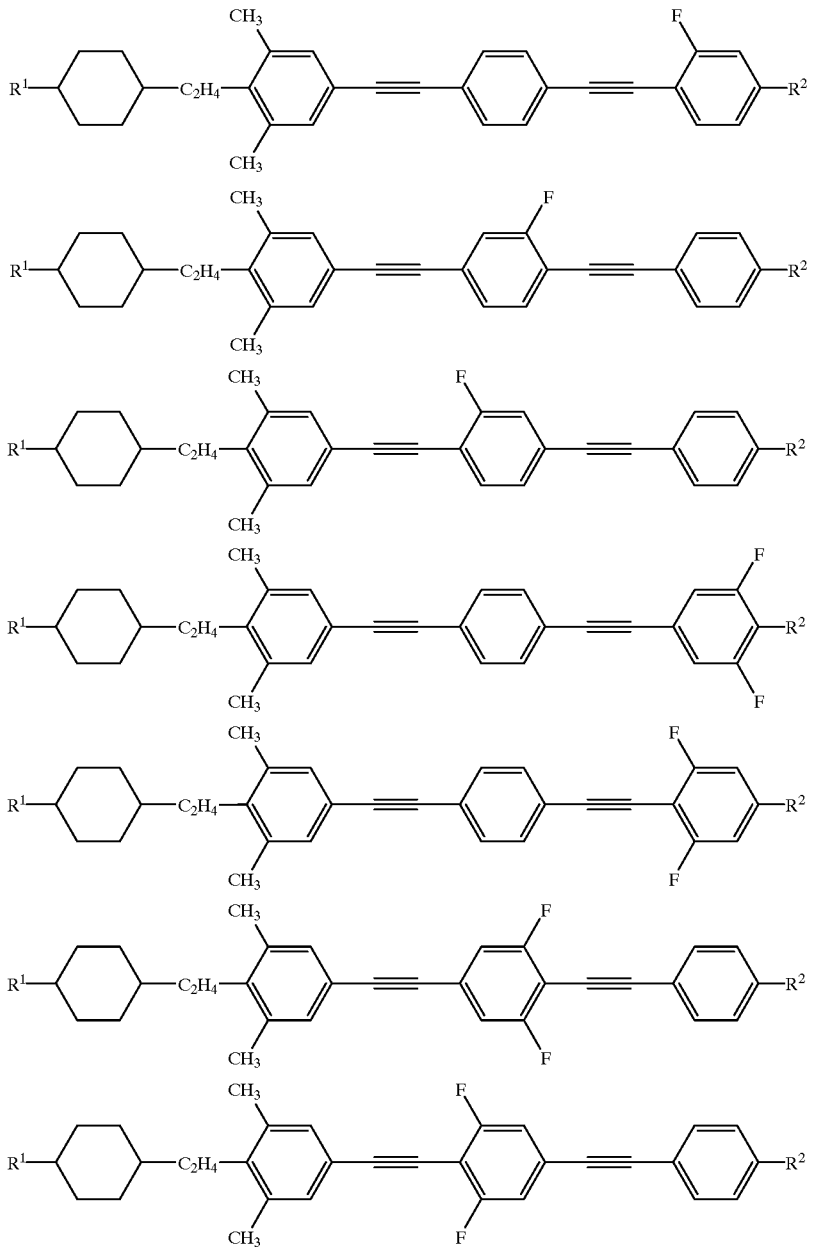

In the formula (3C) representing the compound used in the liquid crystal composition of the present invention, Rings A, B, C, and D each independently stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl. At least one of hydrogen atoms on Rings A, B, C, and D may optionally be substituted with a fluorine atom. $R^5$ and $R^6$ each independently stands for a hydrogen atom, a fluorine atom, a fluoromethyl group, a difluoromethyl group, a trifluoromethyl group, a fluoromethoxy group, a difluoromethoxy group, a trifluoromethoxy group, a cyano group, an alkyl group having 1 to 12 carbon atoms, an alkenyl group having 2 to 12 carbon atoms, an alkoxy group having 1 to 12 carbon atoms, an alkenyloxy group having 2 to 12 carbon atoms, an alkynyloxy group having 3 to 12 carbon atoms, an alkoxyalkyl group having 2 to 16 carbon atoms, or an alkoxyalkenyl group having 3 to 16 carbon atoms. At least one of methylene groups in these groups may optionally be substituted with an oxygen, sulfur, or silicon atom. These groups may be straight or branched. $Z^1$, $Z^2$, and $Z^3$ each independently stands for —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond. b, c, and d each independently denotes 0 or 1 while b+c+d≧1.

Examples of $R^5$ and $R^6$ may include a hydrogen atom; a fluorine atom; a fluoromethyl group; a difluoromethyl group; a trifluoromethyl group; a fluoromethoxy group; a difluoromethoxy group; a trifluoromethoxy group; a cyano group; an alkyl group such as a methyl, ethyl, propyl, butyl, pentyl, hexyl, heptyl, octyl, nonyl, decyl, undecyl, or dodecyl group; an alkenyl group such as an ethenyl, propenyl, butenyl, pentenyl, hexenyl, heptenyl, octenyl, nonenyl, decenyl, undecenyl, or dodecenyl group; an alkoxy group such as a methoxy, ethoxy, propoxy, butoxy, pentyloxy, hexyloxy, heptyloxy, octyloxy, nonyloxy, decyloxy, undecyloxy, or dodecyloxy group; an alkenyloxy group such as a vinyloxy, propenyloxy, butenyloxy, pentenyloxy, hexenyloxy, heptenyloxy, octenyloxy, nonenyloxy, or decenyloxy group; an alkynyloxy group such as a propynyloxy, butynyloxy, pentynyloxy, hexynyloxy, heptynyloxy, octynyloxy, nonynyloxy, decynyloxy, undecynyloxy, or dodecynyloxy group; or an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, decyloxypropyl, methoxybutyl, ethoxybutyl, propoxybutyl, butoxybutyl, pentyloxybutyl, hexyloxybutyl, heptyloxybutyl, octyloxybutyl, nonyloxybutyl, decyloxybutyl, methoxypentyl, ethoxypentyl, propoxypentyl, butoxypentyl, pentyloxypentyl, hexyloxypentyl, heptyloxypentyl, octyloxypentyl, nonyloxypentyl, or decyloxypentyl group.

Preferred examples of the compound represented by the formula (3C) may include compounds represented by the following formulae (4) to (10):

(4)
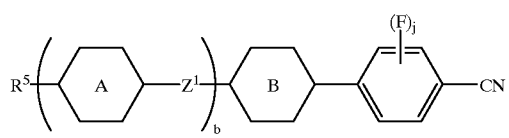

(5)
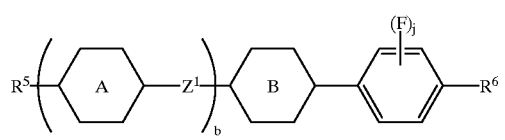

(6)
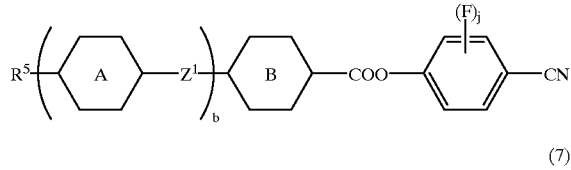

(7)
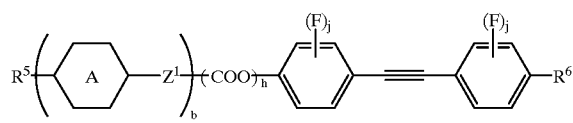

(8)
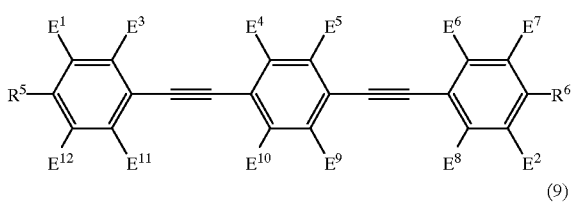

(9)
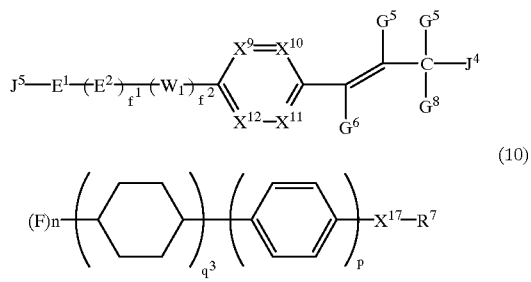

(10)
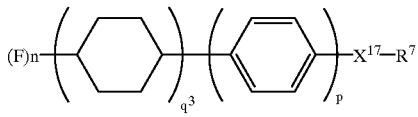

In the formulae (4) to (7), $R^5$, $R^6$, Ring A, Ring B, $Z^1$, and b mean the same as those in the formula (3C), respectively. j is 0, 1, or 2; h is 0 or 1; and i is 0, 1, or 2.

In the formula (8), $E^1$ to $E^{12}$ each independently stands for a hydrogen, fluorine, or chlorine atom.

In the formula (9), $X^9$ to $X^{12}$ each independently stands for CH or CF. $J^4$ stands for a hydrogen atom, a fluorine atom, a cyano group, an alkyl group having 1 to 12 carbon atoms optionally substituted with at least one fluorine atom, an alkenyl group having 2 to 12 carbon atoms optionally substituted with at least one fluorine atom, an alkoxy group having 1 to 12 carbon atoms optionally substituted with at least one fluorine atom, an alkenyloxy group having 2 to 12 carbon atoms optionally substituted with at least one fluorine atom, an alkynyloxy group having 3 to 12 carbon atoms optionally substituted with at least one fluorine atom, or an alkoxyalkyl group having 2 to 12 carbon atoms optionally substituted with at least one fluorine atom. $J^5$ stands for a hydrogen atom, a fluorine atom, a cyano group, or $J^6$—(O)$m^2$, wherein $m^2$ is 0 or 1, and $J^6$ stands for an alkyl group having 1 to 12 carbon atoms, an alkenyl group having 2 to 16 carbon atoms, or an alkynyl group having 3 to 16 carbon atoms, each of which groups may optionally be substituted with at least one fluorine atom. $E^1$ and $E^2$ each independently stands for one of the following groups, wherein $X^{13}$ to $X^{16}$ each independently stands for CH or CF:

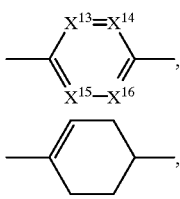 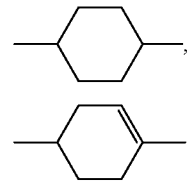

$W^1$ stands for —$C_2H_4$—, —$CH_2O$—, or —$OCH_2$—. $f^1$ and $f^2$ each independently denotes 0 or 1, while both $f^1$ and $f^2$ are not 1 at the same time. When $f^1$ is 1, at least one of $E^1$ and $E^2$ is a group represented by the formula:

$G^5$ to $G^8$ each independently stands for a hydrogen or fluorine atom.

In the formula (10), $R^7$ stands for an alkyl group having 1 to 10 carbon atoms. At least one hydrogen atom on the benzene ring in the formula (10) may optionally be substituted with a fluorine atom. n, p, and $q^3$ each denotes 1 or 2. $X^{17}$ stands for trans —CH═CH— or an ethynyl group, provided that when n is 1, $X^{17}$ may be —CH$_2$—CH$_2$—.

Examples of the compound represented by the formula (3C) may include compounds represented by the formulae below. The following examples also include examples of the compounds represented by the formulae (4) to (10). In the following formulae, W stands for a hydrogen or fluorine atom; x denotes an integer of 0 to 3; Ring H stands for 1,4-cyclohexylene; and Ring G stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl, each of which may optionally be substituted with at least one fluorine atom. Among these, Ring G is preferably 1,4-cyclohexylene, 1,4-cyclohexenylene, 4,1-cyclohexenylene, 2,5-cyclohexenylene, 5,2-cyclohexenylene, 3,6-cyclohexenylene, or 6,3-cyclohexenylene.

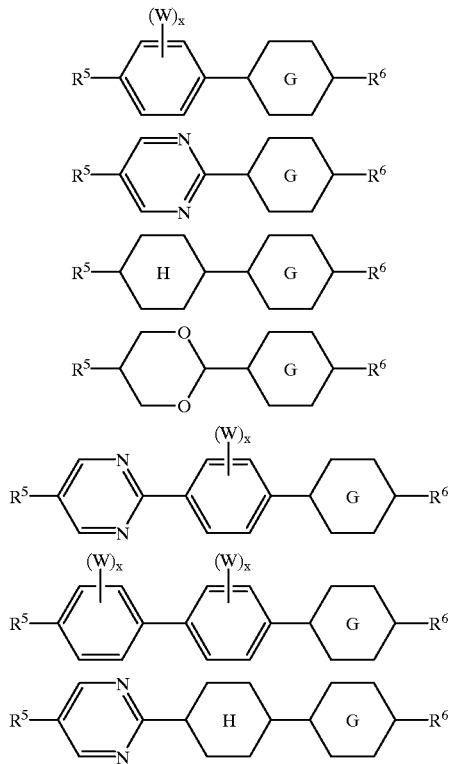

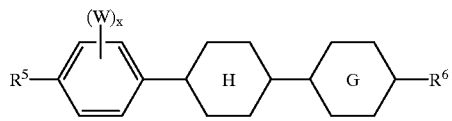
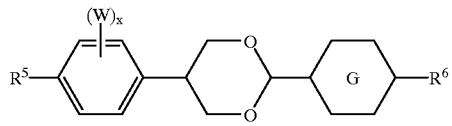
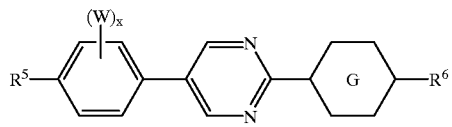
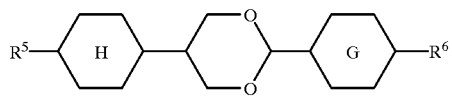
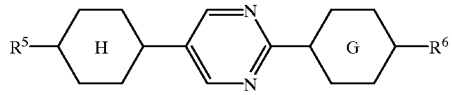
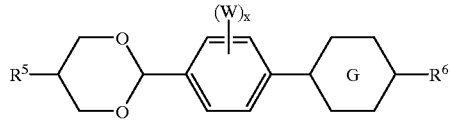
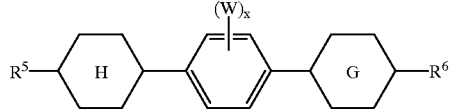
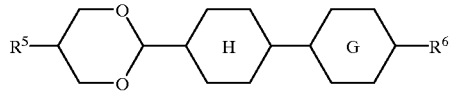
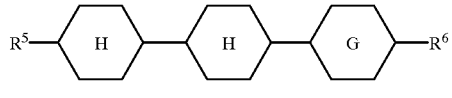
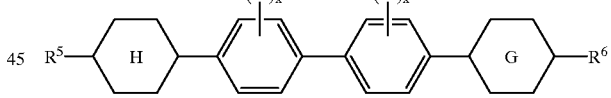
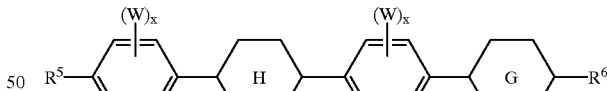
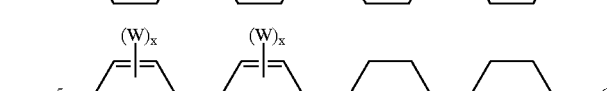
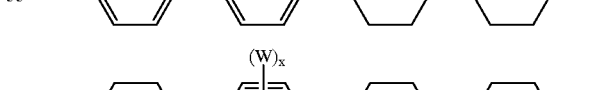
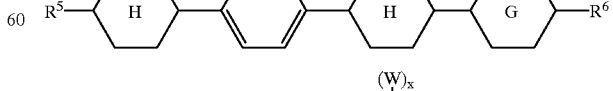

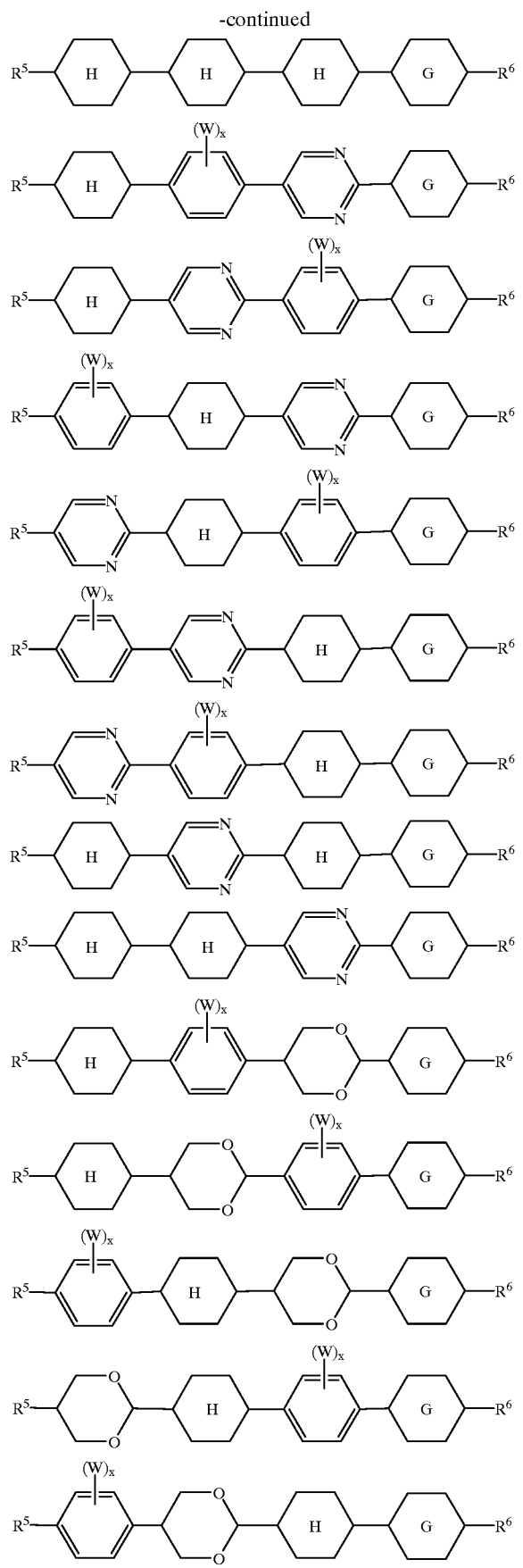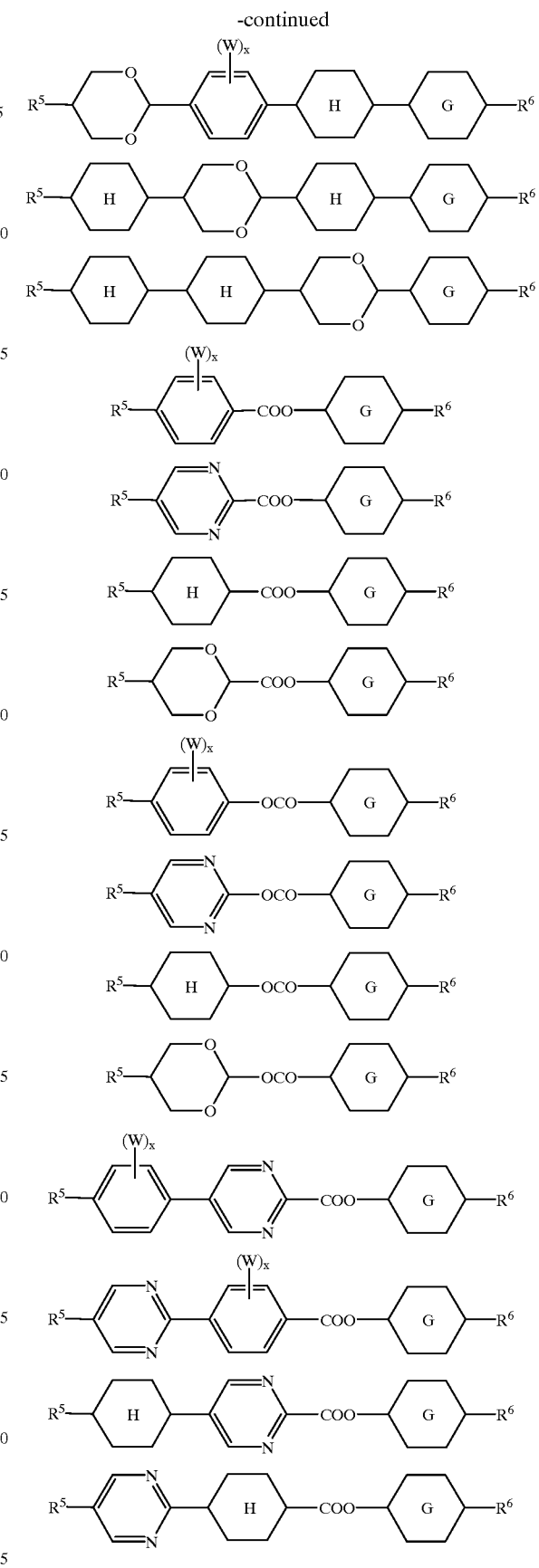

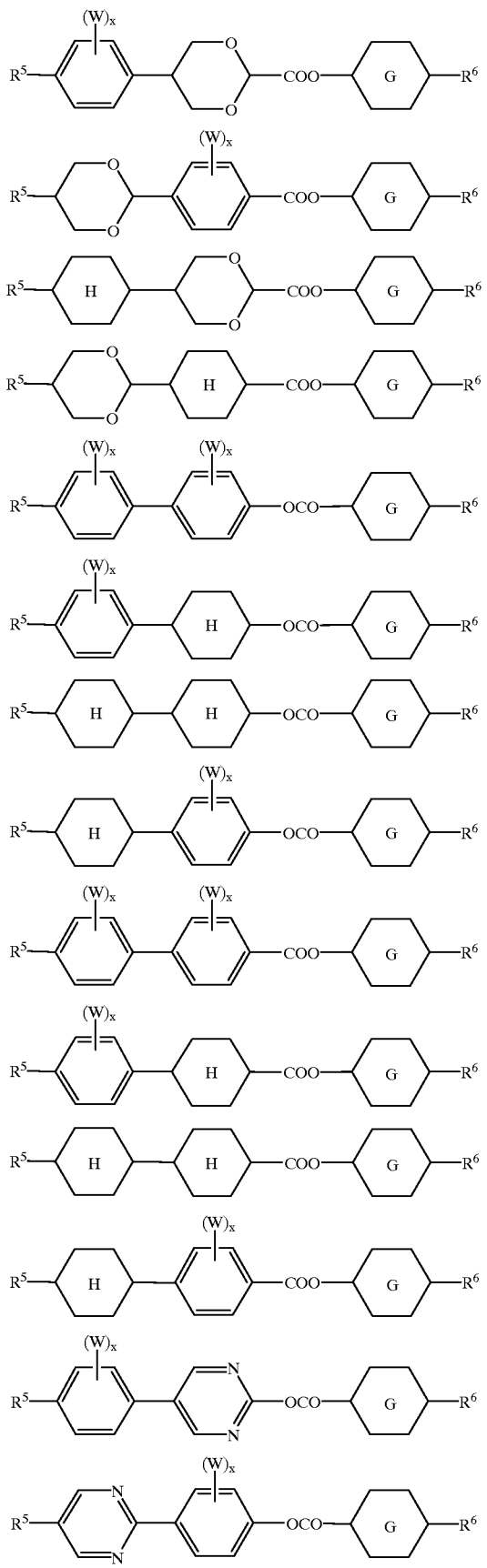
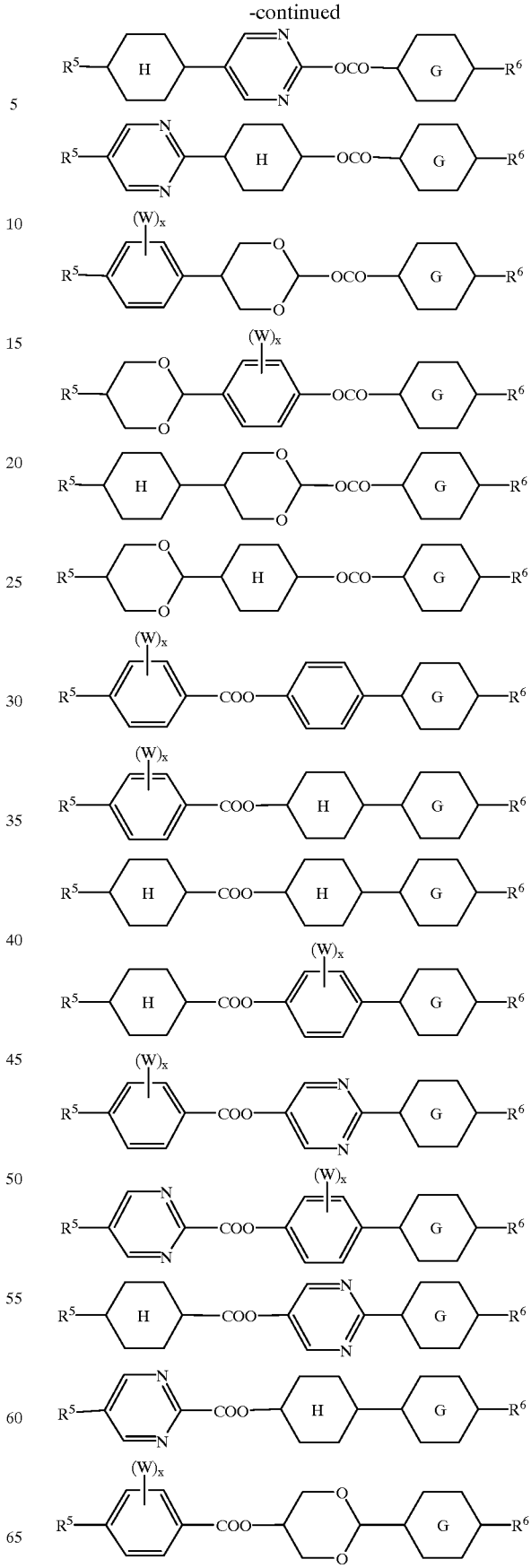

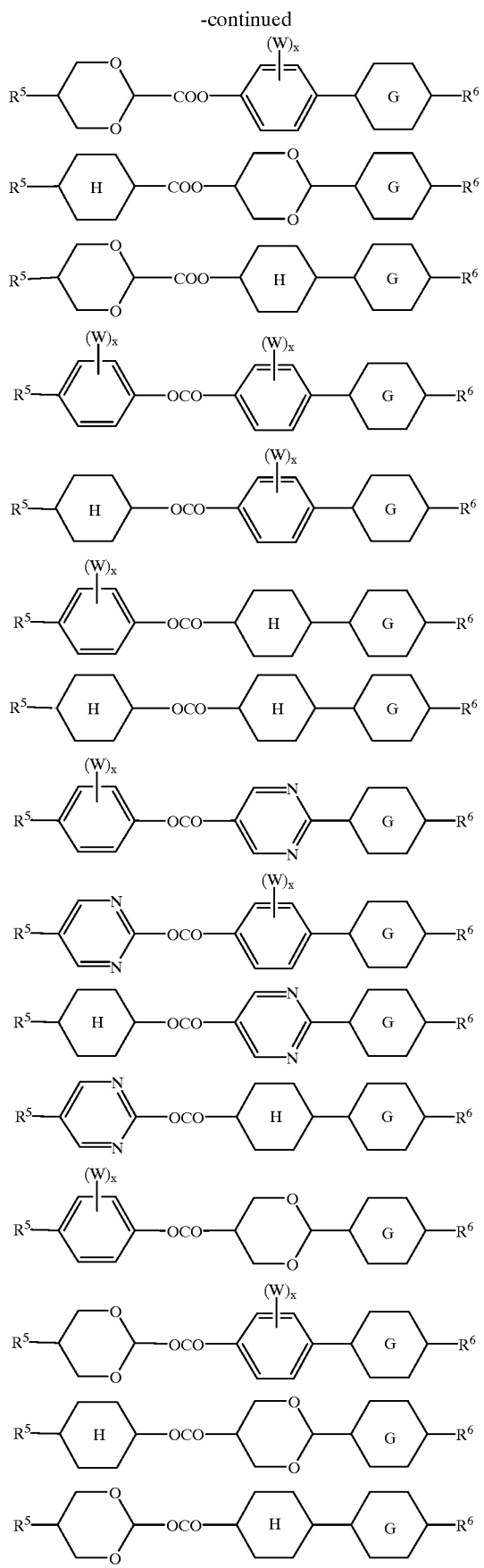
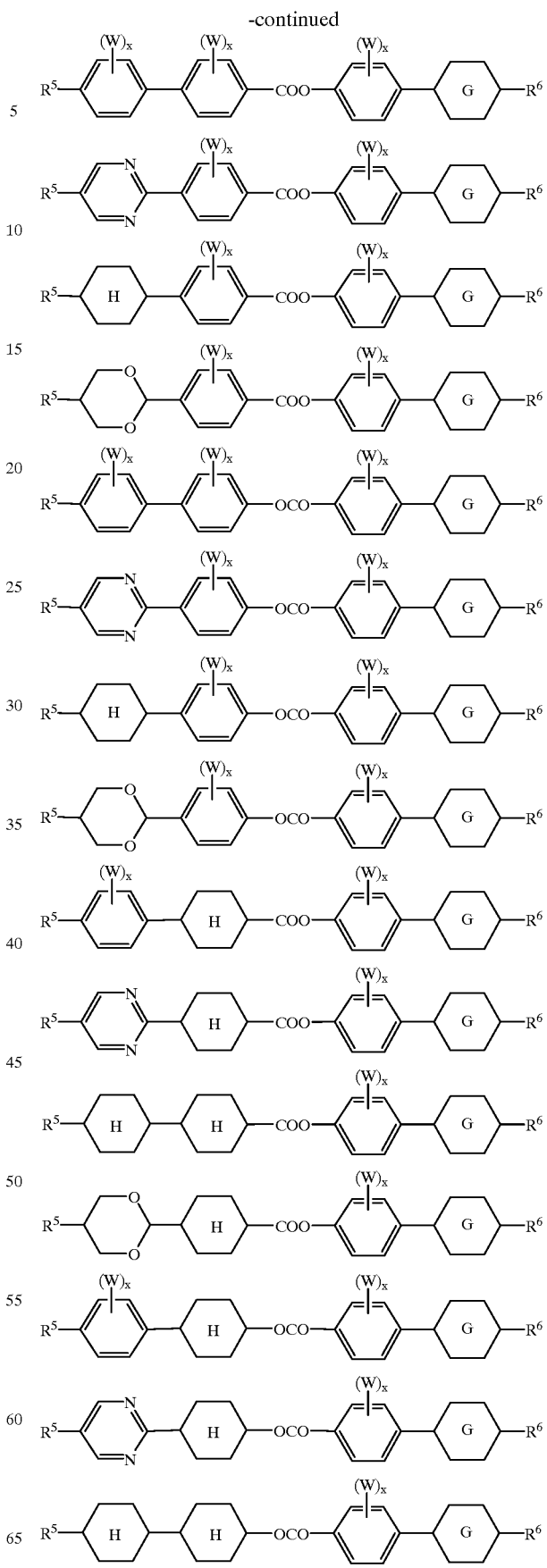

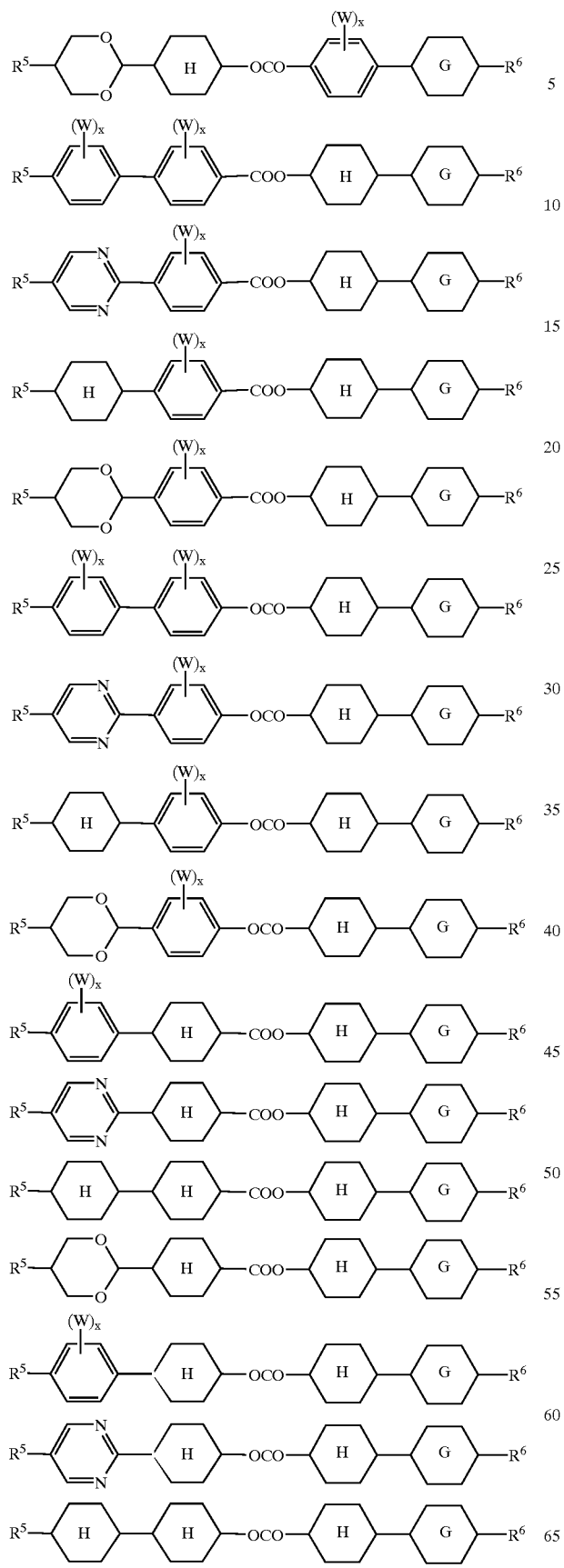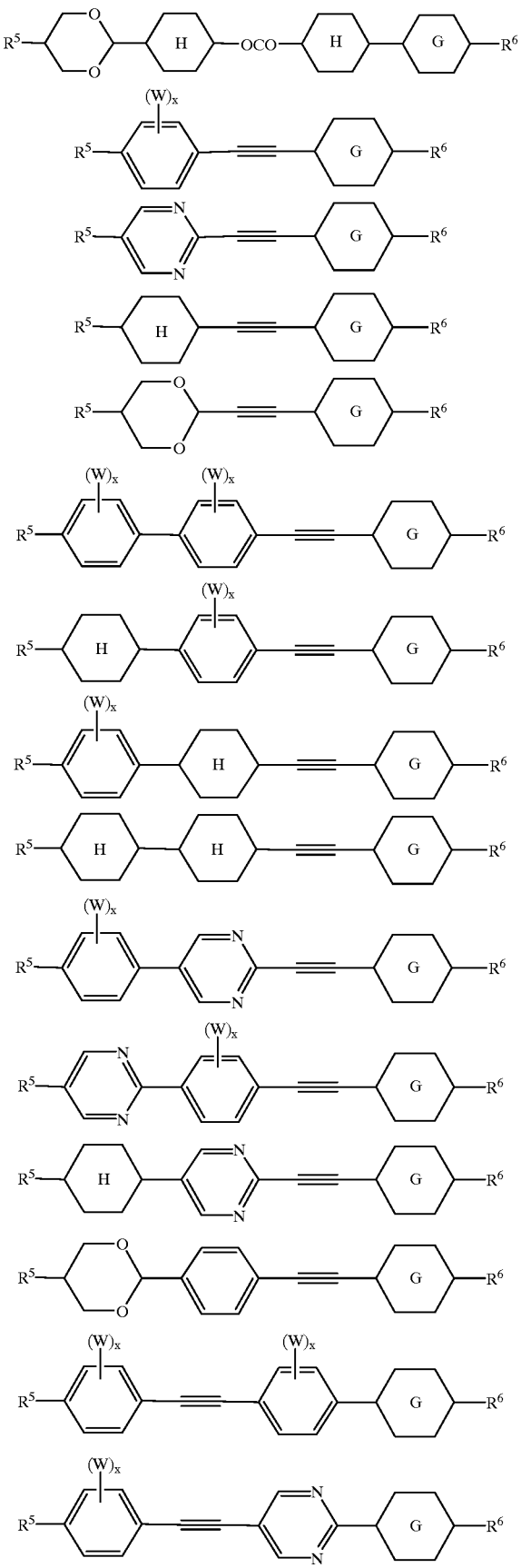

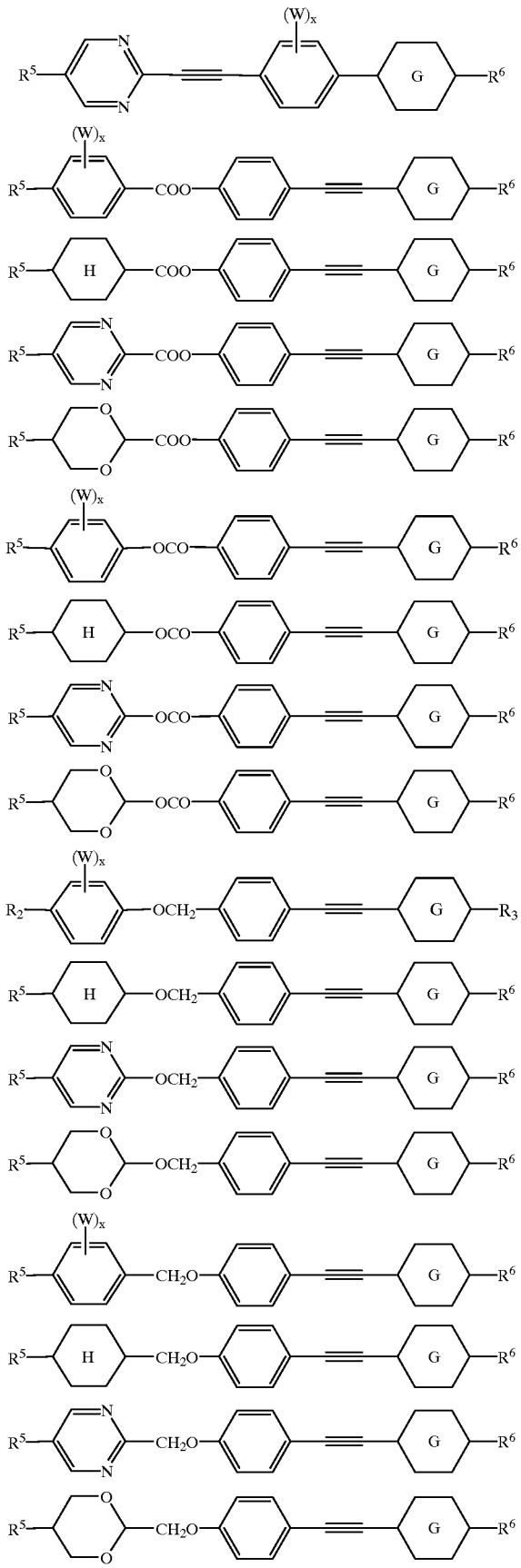
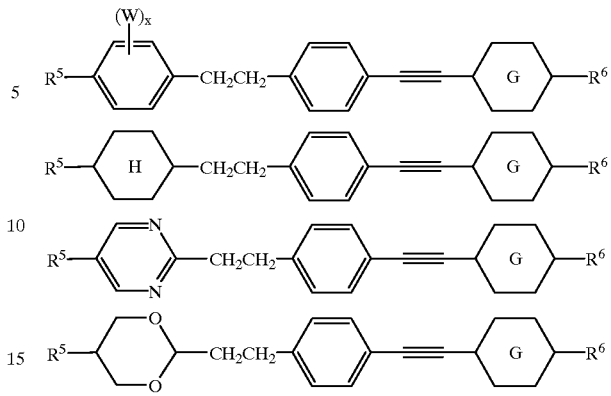

Examples of the compound represented by the formula (3C) also include the following compounds: 1-(1,2-difluoro-1-(E)-pentenyl)-4-(2-(4-propylphenyl)ethynyl)benzene, 1-(1,2-difluoro-1-(E)-heptenyl)-4-(2-(4-propylphenyl)ethynyl)benzene, 1-(1,2-difluoro-1-(E)-butenyl)-4-(2-(4-propylphenyl)ethynyl)benzene, 1-(1,2-difluoro-1-(E)-hexenyl)-4-(2-(4-methylphenyl)ethynyl)benzene, 1-(1,2-difluoro-1-(E)-hexenyl)-4-(2-(4-ethylphenyl)ethynyl)benzene, 1-(1,2-difluoro-1-(E)-hexenyl)-4-(2-(4-butylphenyl)ethynyl)benzene, 1-(1,2-difluoro-1-(E)-hexenyl)-4-(2-(4-pentylphenyl)ethynyl)benzene, 1-(1,2-difluoro-1-(E)-hexenyl)-4-(2-(4-hexylphenyl)ethynyl)benzene, 1-(1,2-difluoro-1-(E)-hexenyl)-4-(2-(4-heptylphenyl)ethynyl)benzene, 1-(1,2-difluoro-1-(E)-hexenyl)-4-(2-(4-methoxyphenyl)ethynyl)benzene, 1-(1,2-difluoro-1-(E)-hexenyl)-4-(2-(4-ethoxyphenyl)ethynyl)benzene, 1-(1,2-difluoro-1-(E)-hexenyl)-3-fluoro-4-(2-(4-pentylphenyl)ethynyl)benzene, 1-(1,2-difluoro-1-(E)-hexenyl)-2-fluoro-4-(2-(4-pentylphenyl)ethynyl)benzene, 1-(1-fluoro-1-(E)-pentenyl)-4-(2-(4-propynylphenyl)ethynyl)benzene, 1-(2-fluoro-1-(E)-pentenyl)-4-(2-(4-propynylphenyl)ethynyl)benzene, 1-(1-fluoro-1-(E)-butenyl)-4-(2-(4-propynylphenyl)ethynyl)benzene, 1-(2-fluoro-1-(E)-hexenyl)-4-(2-(4-methylphenyl)ethynyl)benzene, 1-(1-fluoro-1-(E)-hexenyl)-4-(2-(4-ethylphenyl)ethynyl)benzene, 1-(2-fluoro-1-(E)-hexenyl)-4-(2-(4-butylphenyl)ethynyl)benzene, 1-(1-fluoro-1-(E)-hexenyl)-4-(2-(4-pentylphenyl)ethynyl)benzene, 1-(2-fluoro-1-(E)-hexenyl)-4-(2-(4-hexylphenyl)ethynyl)benzene, 1-(1-fluoro-1-(E)-hexenyl)-4-(2-(4-heptylphenyl)ethynyl)benzene, 1-(2-fluoro-1-(E)-hexenyl)-4-(2-(4-methoxyphenyl)ethynyl)benzene, 1-(1-fluoro-1-(E)-hexenyl)-4-(2-(4-ethoxyphenyl)ethynyl)benzene, 1-(2-fluoro-1-(E)-hexenyl)-3-fluoro-4-(2-(4-pentylphenyl)ethynyl)benzene, 1-(1-fluoro-1-(E)-hexenyl)-2-fluoro-4-(2-(4-pentylphenyl)ethynyl)benzene, 4-(1,2-difluoro-1-(E)-hexenyl)-1-(2-(4-pentyl cyclohexylphenyl)ethynyl)benzene, 4-(1,2-difluoro-1-(E)-hexenyl)-3-fluoro-1-(2-(4-propyl cyclohexylphenyl)ethynyl)benzene, 4-(1-fluoro-1-(E)-hexenyl)-1-(2-(4-propyl cyclohexylphenyl)ethynyl)benzene, 4-(2-(4-(1,2-difluoro-1-(E)-pentenyl)phenyl)ethyl)benzonitrile, 4-(2-(4-(1,2-difluoro-1-(E)-heptenyl)phenyl)ethyl)benzonitrile, 4-(2-(4-(1-fluoro-1-(E)-pentenyl)phenyl)ethyl)benzonitrile, 4-(2-(4-(2-fluoro-1-(E)-pentenyl)phenyl)ethyl)benzonitrile, 4-(2-(4-(1,2-difluoro-1-(E)-pentenyl)phenyl)ethyl)-3-fluorobenzonitrile, 4-(2-(4-(1,2-difluoro-1-(E)-hexenyl)phenyl)ethyl)-3-fluorobenzonitrile, 4-(2-(4-(1,2-difluoro-1-(E)-pentenyl)phenyl)ethyl)-3-fluorobenzonitrile, 4-(2-(4-(1-fluoro-1-(E)-pentenyl)phenyl)ethyl)-3-fluorobenzonitrile, 4-(2-(4-(2-fluoro-1-(E)- pentenyl)phenyl)ethyl)-3-fluorobenzonitrile, 1-(1,2-difluoro-1-(E)-heptenyl)-4-(2-(4-trifluoromethoxyphenyl)ethynyl)benzene, 1-(1,2-difluoro-1-(E)-hexenyl)-4-(2-(4-trifluoromethoxyphenyl)ethynyl)benzene, 1-(1,2-difluoro-1-(E)-pentenyl)-4-(2-(4-trifluoromethoxyphenyl)ethynyl)benzene, 1-(1,2-difluoro-1-(E)-heptenyl)-3-fluoro-4-(2-(4-trifluoromethoxyphenyl)ethynyl)benzene, 1-(1,2-difluoro-1-(E)-hexenyl)-3-fluoro-4-(2-(4-trifluoromethoxyphenyl)ethynyl)benzene, 1-(1,2-difluoro-1-(E)-pentenyl)-3-fluoro-4-(2-(4-trifluoromethoxyphenyl)ethynyl)benzene, 1-(1-fluoro-1-(E)-heptenyl)-4-(2-(4-trifluoromethoxyphenyl)ethynyl)benzene, 1-(2-fluoro-1-(E)-hexenyl)-4-(2-(4-trifluoromethoxyphenyl)ethynyl)benzene, 1-(1-fluoro-1-(E)-pentenyl)-4-(2-(4-trifluoromethoxyphenyl)ethynyl)benzene, 1-(2-fluoro-1-(E)-heptenyl)-3-fluoro-4-(2-(4-trifluoromethoxyphenyl)ethynyl)benzene, 1-(1-fluoro-1-(E)-hexenyl)-3-fluoro-4-(2-(4-trifluoromethoxyphenyl)ethynyl)benzene, 1-(2-fluoro-1-(E)-pentenyl)-3-fluoro-4-(2-(4-trifluoromethoxyphenyl)ethynyl)benzene, 4-(1,2-difluoro-1-(E)-hexenyl)-1-(4-trans-propylcyclohexyl)benzene, 4-(1-fluoro-1-(E)-hexenyl)-1-(4-trans-propylcyclohexyl)benzene, 4-(1,2-difluoro-1-(E)-pentenyl)-1-(4-trans-propylcyclohexyl)benzene, 4-(1,2-difluoro-1-(E)-hexenyl)-1-(4-(4-trans-propylcyclohexyl)cyclohexyl)benzene, 4-(1,2-difluoro-1-(E)-pentenyl)-1-(4-(4-trans-propylcyclohexyl)cyclohexyl)benzene, 4-(1,2-difluoro-1-(E)-hexenyl)-2-fluoro-1-(4-(4-trans-propylcyclohexyl)cyclohexyl)benzene, 4-(1,2-difluoro-1-(E)-hexenyl)-3-fluoro-1-(4-(4-trans-propylcyclohexyl)cyclohexyl)benzene, 4-(1-fluoro-1-(E)-hexenyl)-1-(4-(4-trans-propylcyclohexyl)cyclohexyl)benzene, 4-(2-fluoro-1-(E)-pentenyl)-1-(4-(4-trans-propylcyclohexyl)cyclohexyl)benzene, 2-fluoro-4-(1-fluoro-1-(E)-hexenyl)-1-(4-(4-trans-propylcyclohexyl)cyclohexyl)benzene, 3-fluoro-4-(2-fluoro-1-(E)-hexenyl)-1-(4-(4-trans-propylcyclohexyl)cyclohexyl)benzene, 4-(1,2-difluoro-1-(E)-hexenyl)-4'-propylbiphenyl, 4-(1,2-difluoro-1-(E)-propenyl)-4'-propylbiphenyl, 4-(1,2-difluoro-1-(E)-heptenyl)-4'-propylbiphenyl, 4-(1,2-difluoro-1-(E)-hexenyl)-4'-methylbiphenyl, 4-(1,2-difluoro-1-(E)-heptenyl)-4'-ethylbiphenyl, 4-(1,2-difluoro-1-(E)-heptenyl)-4'-pentylbiphenyl, 4-(1,2-difluoro-1-(E)-nonenyl)-4'-decylbiphenyl, 1-(1,2-difluoro-1-(E)-nonenyl)-4'-nonylbiphenyl, 4-(1,2-difluoro-1-(E)-hexenyl)-4'-fluorobiphenyl, 4-(1,2-difluoro-1-(E)-hexenyl)-4'-cyano biphenyl, 4-(1,2-difluoro-1-(E)-hexenyl)-3'-fluoro-4'-cyano biphenyl, 2-fluoro-4-(1,2-difluoro-1-(E)-hexenyl)-4'-propylbiphenyl, 2'-fluoro-4-(1,2-difluoro-1-(E)-hexenyl)-4'-propylbiphenyl, 3-fluoro-4-(1,2-difluoro-1-(E)-hexenyl)-4'-propylbiphenyl, 2,3-difluoro-4-(1,2-difluoro-1-(E)-hexenyl)-4'-propylbiphenyl, 2,3-difluoro-4-(1,2-difluoro-1-(E)-nonenyl)-4'-decylbiphenyl, 4-(1-fluoro-1-(E)-hexenyl)-4'-propylbiphenyl, 4-(2-fluoro-1-(E)-propenyl)-4'-propylbiphenyl, 4-(1-fluoro-1-(E)-heptenyl)-4'-propylbiphenyl, 4-(2-fluoro-1-(E)-hexenyl)-4'-methylbiphenyl, 4-(1-fluoro-1-(E)-heptenyl)-4'-ethylbiphenyl, 4-(2-fluoro-1-(E)-heptenyl)-4'-pentylbiphenyl, 4-(1-fluoro-1-(E)-nonenyl)-4'-decylbiphenyl, 4-(2-fluoro-1-(E)-nonenyl)-4'-nonylbiphenyl, 4-(1-fluoro-1-(E)-hexenyl)-4'-fluorobiphenyl, 4-(2-fluoro-1-(E)-hexenyl)-4'-cyano biphenyl, 4-(1-fluoro-1-(E)-hexenyl)-3'-fluoro-4'-cyano biphenyl, 2-fluoro-4-(2-fluoro-1-(E)-hexenyl)-4'-propylbiphenyl, 2'-fluoro-4-(1-fluoro-1-(E)-hexenyl)-4'-propylbiphenyl, 3-fluoro-4-(2-fluoro-1-(E)-hexenyl)-4'-propylbiphenyl, 2,3-difluoro-4-(1-fluoro-1-(E)-hexenyl)-4'-propylbiphenyl, 2,3-difluoro-4-(1-fluoro-1-(E)-nonenyl)-4'-decylbiphenyl, 4-(1,2-difluoro-1-(E)-hexenyl)-4''-propyl-p-terphenyl, 4-(1,2-difluoro-1-(E)-hexenyl)-4''-cyano-p-terphenyl, 4-(1,2-difluoro-1-(E)-hexenyl)-4''-cyano-3''-fluoro-p-terphenyl, 4-(1-fluoro-1-(E)-hexenyl)-4''-propyl-p-terphenyl, 4-(2-fluoro-1-(E)-hexenyl)-4''-cyano-p-terphenyl, 2-(4-(1-(1,2-difluoro-1-(E)-hexenyl))phenyl)-5-propylpyrimidine, 2-(4-(1-(1,2-difluoro-1-(E)-pentenyl))phenyl)-5-propylpyrimidine, 2-(4-(1-(1,2-difluoro-1-(E)-nonenyl))phenyl)-5-decyl pyrimidine, 2-(4-(1-(1,2-difluoro-1-(E)-nonenyl))-2,3-difluorophenyl)-5-decyl pyrimidine, 2-(4-(1-(1,2-difluoro-1-(E)-nonenyl))-3-fluorophenyl)-5-decyl pyrimidine, 2-(4-(1-(1-fluoro-1-(E)-hexenyl))phenyl)-5-propylpyrimidine, 2-(4-(1-(2-fluoro-1-(E)-pentenyl))phenyl)-5-propylpyrimidine, 2-(4-(1-(1-fluoro-1-(E)-nonenyl))phenyl)-5-decyl pyrimidine, 2-(4-(1-(2-fluoro-1-(E)-nonenyl))-2,3-difluorophenyl)-5-decyl pyrimidine, 2-(4-(1-(1-fluoro-1-(E)-nonenyl))-3-fluorophenyl)-5-decyl pyrimidine, 1-(4-methylphenyl-methyl)-4-(1,2-difluoro-1-(E)-pentenyl)benzene, 1-(4-ethylphenyl-methyl)-4-(1,2-difluoro-1-(E)-pentenyl)benzene, 1-(4-propylphenyl-methyl)-4-(1-fluoro-1-(E)-pentenyl)benzene, 1-(4-propylphenyl-methyl)-4-(1,2-difluoro-1-(E)-hexenyl)benzene, 1-(4-propylphenyl-methyl)-4-(2-fluoro-1-(E)-heptenyl)benzene, 1-(4-trifluoromethylphenyl-methyl)-4-(1,2-difluoro-1-(E)-pentenyl)benzene, 1-(3,4,5-trifluorophenyl-methyl)-4-(1-fluoro-1-(E)-pentenyl)benzene, 1-(2-(4-methylphenyl)ethyl)-4-(1,2-difluoro-1-(E)-pentenyl)benzene, 1-(2-(4-ethylphenyl)ethyl)-4-(2-fluoro-1-(E)-pentenyl)benzene, 1-(2-(4-propylphenyl)ethyl)-4-(1,2-difluoro-1-(E)-pentenyl)benzene, 1-(2-(4-butylphenyl)ethyl)-4-(1-fluoro-1-(E)-pentenyl)benzene, 1-(2-(4-pentylphenyl)ethyl)-4-(1,2-difluoro-1-(E)-pentenyl)benzene, 1-(2-(4-hexylphenyl)ethyl)-4-(2-fluoro-1-(E)-pentenyl)benzene, 1-(2-(4-heptylphenyl)ethyl)-4-(1,2-difluoro-1-(E)-pentenyl)benzene, 1-(2-(4-octylphenyl)ethyl)-4-(1-fluoro-1-(E)-pentenyl)benzene, 1-(2-(4-nonylphenyl)ethyl)-4-(1,2-difluoro-1-(E)-pentenyl)benzene, 1-(2-(4-decylphenyl)ethyl)-4-(2-fluoro-1-(E)-pentenyl)benzene, 1-(2-(4-propylphenyl)ethyl)-4-(1,2-difluoro-1-(E)-propenyl)benzene, 1-(2-(4-propylphenyl)ethyl)-4-(1-fluoro-1-(E)-butenyl)benzene, 1-(2-(4-propylphenyl)ethyl)-4-(1,2-difluoro-1-(E)-hexenyl)benzene, 1-(2-(4-propylphenyl)ethyl)-4-(2-fluoro-1-(E)-heptenyl)benzene, 1-(2-(4-propylphenyl)ethyl)-4-(1,2-difluoro-1-(E)-octenyl)benzene, 1-(2-(4-decylphenyl)ethyl)-4-(1-fluoro-1-(E)-nonenyl)benzene, 1-(2-(4-decylphenyl)ethyl)-4-(1,2-difluoro-1-(E)-nonenyl)benzene, 1-(4-propylcyclohexyl)-4-(2-(4-(2-fluoro-1-(E)-propenyl)-phenyl)ethyl)benzene, 1-(4-propylcyclohexyl)-4-(2-(4-(1,2-difluoro-1-(E)-butenyl)-phenyl)ethyl)benzene, 1-(4-propylcyclohexyl)-4-(2-(4-(1-fluoro-1-(E)-pentenyl)-phenyl)ethyl)benzene, 1-(4-propylcyclohexyl)-4-(2-(4-(1,2-difluoro-1-(E)-hexenyl)-phenyl)ethyl)benzene, 1-(4-propylcyclohexyl)-4-(2-(4-(2-fluoro-1-(E)-heptenyl)-phenyl)ethyl)benzene, 1-(4-propylcyclohexyl)-4-(2-(4-(1,2-difluoro-1-(E)-octenyl)-phenyl)ethyl)benzene, 1-(4-propylcyclohexyl)-4-(2-(4-(1-fluoro-1-(E)-nonenyl)phenyl)ethyl)benzene, 1-(4-butyl cyclohexyl)-4-(2-(4-(1,2-difluoro-1-(E)-pentenyl)phenyl)ethyl)benzene, 1-(4-pentylcyclohexyl)-4-(2-(4-(2-fluoro-1-(E)-pentenyl)-phenyl)ethyl)benzene, 1-(4-propyl-1-cyclohexenyl)-4-(2-(4-(1,2-difluoro-1-(E)-pentenyl)phenyl)ethyl)benzene, 1-(4-propyl-1-cyclohexenyl)-4-(2-(4-(1-fluoro-1-(E)-heptenyl)phenyl)ethyl)benzene, 1-(2-(4-trifluoromethylphenyl)ethyl)-4-(1,2-difluoro-1-(E)-pentenyl)benzene, 1-(2-(4-cyano phenyl)ethyl)-4-(2-fluoro-1-(E)-pentenyl)benzene, 1-(2-(4-fluorophenyl)ethyl)-4-(1,2-difluoro-1-(E)-pentenyl)benzene, 1-(2-(3,4-difluorophenyl)ethyl)-4-(1-fluoro-1-(E)-pentenyl)benzene, 1-(2-(3,4-difluorophenyl)ethyl)-4-(1,2-difluoro-1-(E)-heptenyl)benzene, 1-(2-(3,4,5-trifluorophenyl)ethyl)-4-(2-fluoro-1-(E)-propenyl)benzene, 1-(2-(3,4,5-trifluorophenyl)ethyl)-4-(1,2-difluoro-1-(E)-butenyl)benzene, 1-(2-(3,4,5-trifluorophenyl)ethyl)-4-(1-fluoro-1-(E)-pentenyl)benzene, 1-(2-(3,4,5-trifluorophenyl)ethyl)-4-(1,2-difluoro-1-(E)-hexenyl)benzene, 1-(2-(3,4,5-trifluorophenyl)ethyl)-4-(2-fluoro-1-(E)-heptenyl)benzene, 1-(2-(3,4,5-trifluorophenyl)ethyl-4-(1,2-difluoro-1-(E)-octenyl)benzene, 1-(2-(3,4,5-trifluorophenyl)ethyl)-4-(1-fluoro-1-(E)-nonenyl)benzene, 1-(2-(4-propyl-3,5-difluorophenyl)ethyl)-4-(1,2-difluoro-1-(E)-propenyl)benzene, 1-(2-(4-propyl-3,5-difluorophenyl)ethyl)-4-(2-fluoro-1-(E)-butenyl)benzene, 1-(2-(4-propyl-3,5-difluorophenyl)ethyl)-4-(1,2-difluoro-1-(E)-pentenyl)benzene, 1-(2-(4-propyl-3,5-difluorophenyl)ethyl)-4-(1-fluoro-1-(E)-hexenyl)benzene, 1-(2-(4-propyl-3,5-difluorophenyl)ethyl)-4-(1,2-difluoro-1-(E)-heptenyl)benzene, 1-(2-(4-methyl-3,5-difluorophenyl)ethyl)-4-(2-fluoro-1-(E)-pentenyl)benzene, 1-(2-(4-ethyl-3,5-difluorophenyl)ethyl)-4-(1,2-difluoro-1-(E)-pentenyl)benzene, 1-(2-(4-butyl-3,5-difluorophenyl)ethyl)-4-(1-fluoro-1-(E)-pentenyl)benzene, 1-(2-(4-pentyl-3,5-difluorophenyl)ethyl)-4-(1,2-difluoro-1-(E)-pentenyl)benzene, 2-fluoro-1-(2-(4-propylphenyl)ethyl)-4-(2-fluoro-1-(E)-pentenyl)benzene, 2-fluoro-1-(2-(4-propylphenyl)ethyl)-4-(1,2-difluoro-1-(E)-hexenyl)benzene, 2-fluoro-1-(2-(4-propylphenyl)ethyl)-4-(1-fluoro-1-(E)-heptenyl)benzene, 3-fluoro-1-(2-(4-propylphenyl)ethyl)-4-(1,2-difluoro-1-(E)-pentenyl)benzene, 3-fluoro-1-(2-(4-propylphenyl)ethyl)-4-(2-fluoro-1-(E)-hexenyl)benzene, 2-fluoro-1-(2-(3,4,5-trifluorophenyl)ethyl)-4-(1,2-difluoro-1-(E)-pentenyl)benzene, 2,6-difluoro-1-(2-(3,4,5-trifluorophenyl)ethyl)-4-(1-fluoro-1-(E)-pentenyl)benzene, 2-fluoro-1-(2-(3,4-difluorophenyl)ethyl)-4-(1,2-difluoro-1-(E)-pentenyl)benzene, 2,6-difluoro-1-(2-(3,4-difluorophenyl)ethyl)-4-(2-fluoro-1-(E)-pentenyl)benzene, 2,6-difluoro-1-(2-(4-propyl-3,5-difluorophenyl)ethyl)-4-(1,2-difluoro-1-(E)-pentenyl)benzene, 2,6-difluoro-1-(2-(4-trifluoromethyl-3,5-difluorophenyl)ethyl)-4-(1-fluoro-1-(E)-pentenyl)benzene, 2,6-difluoro-1-(2-(4-trifluoromethoxy-3,5-difluorophenyl)ethyl)-4-(1,2-difluoro-1-(E)-pentenyl)benzene, 1-(2-(4-cyano-3-fluorophenyl)ethyl)-4-(2-fluoro-1-(E)-pentenyl)benzene, 1-(2-(4-cyano-3-fluorophenyl)ethyl)-4-(1,2-difluoro-1-(E)-heptenyl)benzene, 1-(2-(4-cyano-3-fluorophenyl)ethyl)-2-fluoro-4-(1-fluoro-1-(E)-pentenyl)benzene, 1-(2-(4-cyano-3-fluorophenyl)ethyl)-2,6-difluoro-4-(1,2-difluoro-1-(E)-pentenyl)benzene, 1-(2-(4-cyano-3,5-difluorophenyl)ethyl)-4-(2-fluoro-1-(E)-pentenyl)benzene, 1-(2-(4-cyano-3,5-difluorophenyl)ethyl)-2-fluoro-4-(1,2-difluoro-1-(E)-pentenyl)benzene, 1-(2-(4-cyano-3,5-difluorophenyl)ethyl)-2,6-difluoro-4-(1-fluoro-1-(E)-pentenyl)benzene, 1-(4,4-difluorocyclohexyl)-4-(2-(4-(1,2-difluoro-1-(E)-pentenyl)phenyl)ethyl]benzene, 1-(4-fluorocyclohexyl-4-(2-(4-(2-fluoro-1-(E)-pentenyl)phenyl)ethylbenzene, 1-(2-(4'-propyl-dicyclohexyl)ethyl)-4-(1,2-difluoro-1-(E)-pentenyl)benzene, 1-(2-(4',4-dipropyl-dicyclohexyl)ethyl)-4-(1-fluoro-1-(E)-pentenyl)benzene, 1-(2-(4'-fluorodicyclohexyl)ethyl)-4-(1,2-difluoro-1-(E)-pentenyl)benzene, 1-(2-(4',4-difluorodicyclohexyl)ethyl)-4-(2-fluoro-1-(E)-pentenyl)benzene, 1-(3-(4-propylphenyl)propyl-4-(1,2-difluoro-1-(E)-pentenyl)benzene, 1-(3-(3,4-difluorophenyl)propyl)-4-(1-fluoro-1-(E)-pentenyl)benzene, 1-(3-(3,4,5-trifluorophenyl)propyl)-4-(1,2-difluoro-1-(E)-pentenyl)benzene, 1-(4-(4-propylphenyl)butyl)-4-(2-fluoro-1-(E)-pentenyl)benzene, 1-(4-(3,4-difluorophenyl)butyl)-4-(1,2-difluoro-1-(E)-pentenyl)benzene, 1-(4-(3,4,5-trifluorophenyl)butyl)-4-(1-fluoro-1-(E)-pentenyl)benzene, 1-(4-(3,5-difluoro-4-propylphenyl)butyl)-4-(1,2-difluoro-1-(E)-pentenyl)benzene, 4-(4-methylbenzyloxy)-1-(2-fluoro-1-(E)-pentenyl)benzene, 4-(4-ethylbenzyloxy)-1-(1,2-difluoro-1-(E)-pentenyl)benzene, 4-(4-propylbenzyloxy)-1-(1-fluoro-1-(E)-pentenyl)benzene, 4-(4-butylbenzyloxy)-1-(1,2-difluoro-1-(E)-pentenyl)benzene, 4-(4-pentylbenzyloxy)-1-(2-fluoro-1-(E)-pentenyl)benzene, 4-(4-hexylbenzyloxy)-1-(1,2-difluoro-1-(E)-pentenyl)benzene, 4-(4-heptylbenzyloxy)-1-(1-fluoro-1-(E)-pentenyl)benzene, 4-(4-octylbenzyloxy)-1-(1,2-difluoro-1-(E)-pentenyl)benzene, 4-(4-propylbenzyloxy)-1-(2-fluoro-1-(E)-heptenyl)benzene, 4-(4-nonylbenzyloxy)-1-(1,2-difluoro-1-(E)-heptenyl)benzene, 4-(4-hexylbenzyloxy)-1-(1-fluoro-1-(E)-nonenyl)benzene, 4-(4-heptylbenzyloxy)-1-(1,2-difluoro-1-(E)-nonenyl)benzene, 4-(4-octylbenzyloxy)-1-(2-fluoro-1-(E)-nonenyl)benzene, 4-(4-nonylbenzyloxy)-1-(1,2-difluoro-1-(E)-nonenyl)benzene, 4-(4-decylbenzyloxy)-1-(1-fluoro-1-(E)-nonenyl)benzene, 4-(4-undecylbenzyloxy)-1-(1,2-difluoro-1-(E)-nonenyl)benzene, 4-(4-trifluorobenzyloxy)-1-(2-fluoro-1-(E)-pentenyl)benzene, 4-(4-trifluorobenzyloxy)-1-(1,2-difluoro-1-(E)-heptenyl)benzene, 4-(4-cyanobenzyloxy)-1-(1-fluoro-1-(E)-pentenyl)benzene, 1-(4-(E)-pentenylbenzyloxy)-4-methylbenzene, 1-(4-(E)-pentenylbenzyloxy)-4-ethylbenzene, 1-(4-(E)-pentenylbenzyloxy)-4-propylbenzene, 1-(4-(E)-pentenylbenzyloxy)-4-butylbenzene, 1-(4-(E)-pentenylbenzyloxy)-4-pentylbenzene, 1-(4-(E)-hexenylbenzyloxy)-4-propylbenzene, 1-(4-(E)-heptenylbenzyloxy)-4-propylbenzene, 1-(4-(E)-pentenylbenzyloxy)-4-trifluoromethylbenzene, 1-(4-(E)-pentenylbenzyloxy)-3,4,5-trifluorobenzene, 1-(4-(E)-pentenylbenzyloxy)-4-cyanobenzene, 4-(4-methylphenoxy)-1-(1,2-difluoro-1-(E)-pentenyl)benzene, 4-(4-ethylphenoxy)-1-(2-fluoro-1-(E)-pentenyl)benzene, 4-(4-propylphenoxy)-1-(1,2-difluoro-1-(E)-pentenyl )benzene, 4-(4-butylphenoxy)-1-(1-fluoro-1-(E)-pentenyl)benzene, 4-(4-pentyphenoxy)-1-(1,2-difluoro-1-(E)-pentenyl)benzene, 4-(4-hexylphenoxy)-1-(2-fluoro-1-(E)-pentenyl)benzene, 4-(4-propylphenoxy)-1-(1,2-difluoro-1-(E)-propenyl)benzene, 4-(4-propylphenoxy)-1-(1-fluoro-1-(E)-butenyl)benzene, 4-(4-propylphenoxy)-1-(1,2-difluoro-1-(E)-pentenyl)benzene, 4-(4-propylphenoxy)-1-(2-fluoro-1-(E)-hexenyl)benzene, 4-(4-propylphenoxy)-1-(1,2-difluoro-1-(E)-heptenyl)benzene, 4-(4-propylphenoxy)-1-(1-fluoro-1-(E)-octenyl)benzene, 4-(4-trifluoromethylphenoxy)-1-(1,2-difluoro-1-(E)-pentenyl)benzene, (4-(2-fluoro-1-(E)-propenyl))phenyl-(4-propyl)benzoate, (4-(1,2-difluoro-1-(E)-butenyl))phenyl-(4-propyl)benzoate, (4-(1-fluoro-1-(E)-pentenyl))phenyl-(4-propyl)benzoate, (4-(1,2-difluoro-1-(E)-hexenyl))phenyl-(4-propyl)benzoate, (4-(2-fluoro-1-(E)-heptenyl))phenyl-(4-propyl)benzoate, (4-(1,2-difluoro-1-(E)-octenyl))phenyl-(4-propyl)benzoate, (4-(1-fluoro-1-(E)-pentenyl))phenyl-(4-methyl)benzoate, (4-(1,2-difluoro-1-(E)-pentenyl))phenyl-(4-ethyl)benzoate, (4-(2-fluoro-1-(E)-pentenyl))phenyl-(4-propyl)benzoate, (4-(1,2-difluoro-1-(E)-pentenyl))phenyl-(4-butyl)benzoate, (4-(1-fluoro-1-(E)-pentenyl))phenyl-(4-pentyl)benzoate, (4-(1,2-difluoro-1-(E)-propenyl))phenyl-(4-(4-propylcyclohexyl))benzoate, (4-(2-fluoro-1-(E)-butenyl))phenyl-(4-(4-propylcyclohexyl))benzoate, (4-(1,2-difluoro-1-(E)-pentenyl))phenyl-(4-(4-propylcyclohexyl))benzoate, (4-(1-fluoro-1-(E)-hexenyl))phenyl-(4-(4-propylcyclohexyl))benzoate, (4-(1,2-difluoro-1-(E)-heptenyl))phenyl-(4-(4-propylcyclohexyl))benzoate, (4-(2-fluoro-1-(E)-octenyl))phenyl-(4-(4-propylcyclohexyl))benzoate, (4-(1,2-difluoro-1-(E)-heptenyl))phenyl-(4-(4- methylcyclohexyl))benzoate, (4-(1-fluoro-1-(E)-pentenyl)) phenyl-(4-(4-ethylcyclohexyl))benzoate, (4-(1,2-difluoro-1-(E)-pentenyl))phenyl-(4-(4-butylcyclohexyl))benzoate, (4-(2-fluoro-1-(E)-pentenyl))phenyl-(4-(4-pentylcyclohexyl)) benzoate, (4-(1,2-difluoro-1-(E)-pentenyl))phenyl-(4-(4-propylcyclohexyl))benzoate, (4-(1-fluoro-1-(E)-pentenyl)) phenyl-(4-(4-pentylcyclohexyl))benzoate, (4-(1,2-difluoro-1-(E)-propenyl))phenyl-(4-cyano-3-fluoro)benzoate, (4-(2-fluoro-1-(E)-butenyl))phenyl-(4-cyano-3-fluoro)benzoate, (4-(1,2-difluoro-1-(E)-pentenyl))phenyl-(4-cyano-3-fluoro) benzoate, (4-(1-fluoro-1-(E)-hexenyl))phenyl-(4-cyano-3-fluoro)benzoate, (4-(1,2-difluoro-1-(E)-heptenyl))phenyl-(4-cyano-3-fluoro)benzoate, (4-(2-fluoro-1-(E)-octenyl))phenyl-(4-cyano-3-fluoro)benzoate, (4-(1,2-difluoro-1-(E)-propenyl))phenyl-(3,4-difluoro))benzoate, (4-(1-fluoro-1-(E)-pentenyl))phenyl-(3,4-difluoro))benzoate, (4-(1,2-difluoro-1-(E)-heptenyl))phenyl-(3,4-difluoro)benzoate, (4-(2-fluoro-1-(E)-propenyl))phenyl-(3,4,5-trifluoro)) benzoate, (4-(1,2-difluoro-1-(E)-pentenyl))phenyl-(3,4,5-trifluoro))benzoate, (4-(1-fluoro-1-(E)-heptenyl))phenyl-(3, 4,5-trifluoro))benzoate, 4-methylphenyl-(4-(1,2-difluoro-1-(E)-pentenyl))benzoate, 4-ethylphenyl-(4-(2-fluoro-1-(E)-pentenyl))benzoate, 4-propylphenyl-(4-(1,2-difluoro-1-(E)-pentenyl))benzoate, 4-butylphenyl-(4-(1-fluoro-1-(E)-pentenyl))benzoate, 4-pentylphenyl-(4-(1,2-difluoro-1-(E)-pentenyl))benzoate, 4-hexylphenyl-(4-(2-fluoro-1-(E)-pentenyl))benzoate, 4-heptylphenyl-(4-(1,2-difluoro-1-(E)-pentenyl))benzoate, 4-octylphenyl-(4-(1-fluoro-1-(E)-nonenyl))benzoate, 4-nonylphenyl-(4-(1,2-difluoro-1-(E)-nonenyl))benzoate, 4-decylphenyl-(4-(2-fluoro-1-(E)-nonenyl))benzoate, 4-undecylphenyl-(4-(1,2-difluoro-1-(E)-nonenyl))benzoate, 4-octylphenyl-(4-(1-fluoro-1-(E)-nonenyl))benzoate, 4-nonyloxyphenyl-(4-(1,2-difluoro-1-(E)-nonenyl))benzoate, 4-decyloxyphenyl-(4-(2-fluoro-1-(E)-nonenyl))benzoate, 4-(4-methylcyclohexyl)phenyl-(4-(1,2-difluoro-1-(E)-pentenyl))benzoate, 4-(4-ethylcyclohexyl)phenyl-(4-(1-fluoro-1-(E)-pentenyl)) benzoate, 4-(4-propylcyclohexyl)phenyl-(4-(1,2-difluoro-1-(E)-pentenyl))benzoate, 4-(4-butylcyclohexyl)phenyl-(4-(2-fluoro-1-(E)-pentenyl))benzoate, 4-(4-pentylcyclohexyl) phenyl-(4-(1,2-difluoro-1-(E)-pentenyl))benzoate, 4-(4-hexylcyclohexyl)phenyl-(4-(1-fluoro-1-(E)-pentenyl)) benzoate, 4-(4-propylcyclohexyl)phenyl-(4-(1,2-difluoro-1-(E)-propenyl))benzoate, 4-(4-propylcyclohexyl)phenyl-(4-(2-fluoro-1-(E)-butenyl))benzoate, 4-(4-propylcyclohexyl) phenyl-(4-(1,2-difluoro-1-(E)-hexenyl))benzoate, 4-(4-propylcyclohexyl)phenyl-(4-(1-fluoro-1-(E)-heptenyl)) benzoate, 4-(4-propylcyclohexyl)phenyl-(4-(1,2-difluoro-1-(E)-octenyl))benzoate, 4-(4-propylcyclohexyl)phenyl-(4-(2-fluoro-1-(E)-pentenyl))benzoate, 4-(4-cyano-3-fluoro) phenyl-(4-(1,2-difluoro-1-(E)-pentenyl))benzoate, 4-(4-cyano-3-fluoro)phenyl-(4-(1-fluoro-1-(E)-heptenyl)) benzoate, 4-(3,4-difluoro)phenyl-(4-(1,2-difluoro-1-(E)-pentenyl))benzoate, 4-(3,4-difluoro)phenyl-(4-(2-fluoro-1-(E)-heptenyl))benzoate, 4-(3,4,5-trifluoro)phenyl-(4-(1,2-difluoro-1-(E)-pentenyl))benzoate, 4-(3,4,5-trifluoro) phenyl-(4-(1-fluoro-1-(E)-heptenyl))benzoate, 1-(4-methylphenyl-methyl)-4-(1-(E)-pentenyl)benzene, 1-(4-ethylphenyl-methyl)-4-(1-(E)-pentenyl)benzene, 1-(4-propylphenyl-methyl)-4-(1-(E)-pentenyl)benzene, 1-(4-propylphenyl-methyl)-4-(1-(E)-hexenyl)benzene, 1-(4-propylphenyl-methyl)-4-(1-(E)-heptenyl)benzene, 1-(4-trifluoromethylphenyl-methyl)-4-(1-(E)-pentenyl)benzene, 1-(3,4,5-trifluorophenylmethyl)-4-(1-(E)-pentenyl)benzene, 1-(2-(4-methylphenyl)ethyl)-4-(1-(E)-pentenyl)benzene, 1-(2-(4-ethylphenyl)ethyl)-4-(1-(E)-pentenyl)benzene, 1-(2-(4-propylphenyl)ethyl)-4-(1-(E)-pentenyl)benzene, 1-(2-(4-butylphenyl)ethyl)-4-(1-(E)-pentenyl)benzene, 1-(2-(4-pentylphenyl)ethyl)-4-(1-(E)-pentenyl)benzene, 1-(2-(4-hexylphenyl)ethyl)-4-(1-(E)-pentenyl)benzene, 1-(2-(4-heptylphenyl)ethyl)-4-(1-(E)-pentenyl)benzene, 1-(2-(4-octylphenyl)ethyl)-4-(1-(E)-pentenyl)benzene, 1-(2-(4-nonylphenyl)ethyl)-4-(1-(E)-pentenyl)benzene, 1-(2-(4-decylphenyl)ethyl)-4-(1-(E)-pentenyl)benzene, 1-(2-(4-propylphenyl)ethyl)-4-(1-(E)-propenyl)benzene, 1-(2-(4-propylphenyl)ethyl)-4-(1-(E)-butenyl)benzene, 1-(2-(4-propylphenyl)ethyl)-4-(1-(E)-hexenyl)benzene, 1-(2-(4-propylphenyl)ethyl)-4-(1-(E)-heptenyl)benzene, 1-(2-(4-propylphenyl)ethyl)-4-(1-(E)-octenyl)benzene, 1-(2-(4-decylphenyl)ethyl)-4-(1-(E)-nonenyl)benzene, 1-(2-(4-decyloxyphenyl)ethyl)-4-(1-(E)-nonenyl)benzene, 1-(4-propylcyclohexyl)-4-(2-(4-(1-(E)-propenyl)-phenyl)ethyl) benzene, 1-(4-propylcyclohexyl)-4-(2-(4-(1-(E)-butenyl)-phenyl)ethyl)benzene, 1-(4-propylcyclohexyl)-4-(2-(4-(1-(E)-pentenyl)-phenyl)ethyl)benzene, 1-(4-propylcyclohexyl)-4-(2-(4-(1-(E)-hexenyl)-phenyl)ethyl) benzene, 1-(4-propylcyclohexyl)-4-(2-(4-(1-(E)-heptenyl)-phenyl)ethyl)benzene, 1-(4-propylcyclohexyl)-4-(2-(4-(1-(E)-octenyl)-phenyl)ethyl)benzene, 1-(4-propylcyclohexyl)-4-(2-(4-(1-(E)-nonenyl)-phenyl)ethyl)benzene, 1-(4-butylcyclohexyl-4-(2-(4-(1-(E)-pentenyl)-phenyl)ethyl) benzene, 1-(4-pentylcyclohexyl)-4-(2-(4-(1-(E)-pentenyl)-phenyl)ethyl)benzene, 1-(4-propyl-1-cyclohexenyl)-4-(2-(4-(1-(E)-pentenyl-phenyl)ethyl)benzene, 1-(4-propyl-1-cyclohexenyl)-4-(2-(4-(1-(E)-heptenyl)-phenyl)ethyl) benzene, 1-(2-(4-trifluoromethylphenyl)ethyl)-4-(1-(E)-pentenyl)benzene, 1-(2-(4-cyanophenyl)ethyl)-4-(1-(E)-pentenyl)benzene, 1-(2-(4-fluorophenyl)ethyl)-4-(1-(E)-pentenyl)benzene, 1-(2-(3,4-difluorophenyl)ethyl)-4-(1-(E)-pentenyl)benzene, 1-(2-(3,4-difluorophenyl)ethyl)-4-(1-(E)-heptenyl)benzene, 1-(2-(3,4,5-trifluorophenyl)ethyl)-4-(1-(E)-propenyl)benzene, 1-(2-(3,4,5-trifluorophenyl)ethyl)-4-(1-(E)-butenyl)benzene, 1-(2-(3,4,5-trifluorophenyl)ethyl)-4-(1-(E)-pentenyl)benzene, 1-(2-(3,4,5-trifluorophenyl) ethyl)-4-(1-(E)-hexenyl)benzene, 1-(2-(3,4,5-trifluorophenyl)ethyl)-4-(1-(E)-heptenyl)benzene, 1-(2-(3,4, 5-trifluorophenyl)ethyl)-4-(1-(E)-octenyl)benzene, 1-(2-(3, 4,5-trifluorophenyl)ethyl)-4-(1-(E)-nonenyl)benzene, 1-(2-(4-propyl-3,5-difluorophenyl)ethyl)-4-(1-(E)-propenyl) benzene, 1-(2-(4-propyl-3,5-difluorophenyl)ethyl)-4-(1-(E)-butenyl)benzene, 1-(2-(4-propyl-3,5-difluorophenyl)ethyl)-4-(1-(E)-pentenyl)benzene, 1-(2-(4-propyl-3,5-difluorophenyl)ethyl)-4-(1-(E)-hexenyl)benzene, 1-(2-(4-propyl-3,5-difluorophenyl)ethyl)-4-(1-(E)-heptenyl) benzene, 1-(2-(4-methyl-3,5-difluorophenyl)ethyl)-4-(1-(E)-pentenyl)benzene, 1-(2-(4-ethyl-3,5-difluorophenyl) ethyl)-4-(1-(E)-pentenyl)benzene, 1-(2-(4-butyl-3,5-difluorophenyl)ethyl)-4-(1-(E)-pentenyl)benzene, 1-(2-(4-pentyl-3,5-difluorophenyl)ethyl)-4-(1-(E)-pentenyl) benzene, 2-fluoro-1-(2-(4-propylphenyl)ethyl)-4-(1-(E)-pentenyl)benzene, 2-fluoro-1-(2-(4-propylphenyl)ethyl)-4-(1-(E)-hexenyl)benzene, 2-fluoro-1-(2-(4-propylphenyl) ethyl)-4-(1-(E)-heptenyl)benzene, 3-fluoro-1-(2-(4-propylphenyl)ethyl)-4-(1-(E)-pentenyl)benzene, 3-fluoro-1-(2-(4-propylphenyl)ethyl)-4-(1-(E)-hexenyl)benzene, 2-fluoro-1-(2-(3,4,5-trifluorophenyl)ethyl)-4-(1-(E)-pentenyl)benzene, 2,6-difluoro-1-(2-(3,4,5-trifluorophenyl) ethyl)-4-(1-(E)-pentenyl)benzene, 2-fluoro-1-(2-(3,4-difluorophenyl)ethyl)-4-(1-(E)-pentenyl)benzene, 2,6-difluoro-1-(2-(3,4-difluorophenyl)ethyl)-4-(1-(E)-pentenyl) benzene, 2,6-difluoro-1-(2-(4-propyl-3,5-difluorophenyl) ethyl)-4-(1-(E)-pentenyl)benzene, 2,6-difluoro-1-(2-(4-trifluoromethyl-3,5-difluorophenyl)ethyl)-4-(1-(E)-pentenyl)benzene, 2,6-difluoro-1-(2-(4-trifluoromethoxy-3, 5-difluorophenyl)ethyl)-4-(1-(E)-pentenyl)benzene, 1-(2-(4-cyano-3-fluorophenyl)ethyl)-4-(1-(E)-pentenyl)benzene, 1-(2-(4-cyano-3-fluorophenyl)ethyl)-4-(1-(E)-heptenyl)benzene, 1-(2-(4-cyano-3-fluorophenyl)ethyl)-2-fluoro-4-(1-(E)-pentenyl)benzene, 1-(2-(4-cyano-3-fluorophenyl)ethyl)-2,6-difluoro-4-(1-(E)-pentenyl)benzene, 1-(2-(4-cyano-3,5-difluorophenyl)ethyl)-4-(1-(E)-pentenyl)benzene, 1-(2-(4-cyano-3,5-difluorophenyl)ethyl)-2-fluoro-4-(1-(E)-pentenyl)benzene, 1-(2-(4-cyano-3,5-difluorophenyl)ethyl)-2,6-difluoro-4-(1-(E)-pentenyl)benzene, 1-(4,4-difluorocyclohexyl)-4-(2-(4-(1-(E)-pentenyl)phenyl)ethyl)-benzene, 1-(4-fluorocyclohexyl-4-(2-(4-(1-(E)-pentenyl)phenyl)ethyl)-benzene, 1-(2-(4'-propyldicyclohexyl)ethyl-4-(1-(E)-pentenyl)-benzene, 1-(2-(4',4'-dipropyl-dicyclohexyl)ethyl)-4-(1-(E)-pentenyl)-benzene, 1-(2-(4'-fluoro-dicyclohexyl)ethyl)-4-(1-(E)-pentenyl)-benzene, 1-(2-(4',4'-fluoro-dicyclohexyl)ethyl)-4-(1-(E)-pentenyl)-benzene, 1-(3-(4-propylphenyl)propyl)-4-(1-(E)-pentenyl)benzene, 1-(3-(3,4-difluorophenyl)propyl)-4-(1-(E)-pentenyl)benzene, 1-(3-(3,4,5-trifluorophenyl)propyl)-4-(1-(E)-pentenyl)benzene, 1-(4-propylphenyl)butyl)-4-(1-(E)-pentenyl)benzene, 1-(4-(3,4-difluorophenyl)butyl)-4-(1-(E)-pentenyl)benzene, 1-(4-(3,4,5-trifluorophenyl)butyl)-4-(1-(E)-pentenyl)benzene, 1-(4-(3,5-difluoro-4-propylphenyl)butyl)-4-(1-(E)-pentenyl)benzene, 4-(4-methylbenzyloxy)-1-(1-(E)-pentenyl)benzene, 4-(4-ethylbenzyloxy)-(1-(E)-pentenyl)benzene, 4-(4-propylbenzyloxy)-1-(1-(E)-pentenyl)benzene, 4-(4-butylbenzyloxy)-1-(1-(E) -pentenyl)benzene, 4-(4-pentylbenzyloxy)-1-(1-(E)-pentenyl)benzene, 4-(4-hexylbenzyloxy)-1-(1-(E)-pentenyl)benzene, 4-(4-heptylbenzyloxy)-1-(1-(E)-pentenyl)benzene, 4-(4-octylbenzyloxy)-1-(1-(E)-peptenyl)benzene, 4-(4-propylbenzyloxy)-1-(1-(E)-heptenyl)benzene, 4-(4-nonylbenzyloxy)-1-(1-(E)-heptenyl)benzene, 4-(4-hexylbenzyloxy)-1-(1-(E)-nonenyl)benzene, 4-(4-heptylbenzyloxy)-1-(1-(E)-nonenyl)benzene, 4-(4-octylbenzyloxy)-1-(1-(E) -nonenyl)benzene, 4-(4-nonylbenzyloxy)-1-(1-(E)-nonenyl)benzene, 4-(4-decylbenzyloxy)-1-(1-(E)-nonenyl)benzene, 4-(4-undecylbenzyloxy)-1-(1-(E)-nonenyl)benzene, 4-(4-trifluoromethylbenzyloxy)-1-(1-(E)-pentenyl)benzene, 4-(4-trifluoromethylbenzyloxy)-1-(1-(E)-heptenyl)benzene, 4-(4-cyano benzyloxy)-1-(1-(E)-pentenyl)benzene, 1-(4-(E)-pentenylbenzyloxy)-4-methylbenzene, 1-(4-(E)-pentenylbenzyloxy)-4-ethylbenzene, 1-(4-(E)-pentenylbenzyloxy)-4-propylbenzene, 1-(4-(E)-pentenylbenzyloxy)-4-butylbenzene, 1-(4-(E)-pentenylbenzyloxy)-4-pentylbenzene, 1-(4-(E)-pentenylbenzyloxy)-4-propylbenzene, 1-(4-(E)-hexenylbenzyloxy)-4-propylbenzene, 1-(4-(E)-heptenylbenzyloxy)-4-propylbenzene, 1-(4-(E)-pentenylbenzyloxy)-4-trifluoromethylbenzene, 1-(4-(E)-pentenylbenzyloxy)-3,4,5-trifluorobenzene, 1-(4-(E)-pentenylbenzyloxy)-4-cyano benzene, 4-(4-methylphenoxy)-1-(1-(E)-pentenyl)benzene, 4-(4-ethylphenoxy)-1-(1-(E)-pentenyl)benzene, 4-(4-propylphenoxy)-1-(1-(E)-pentenyl)benzene, 4-(4-butylphenoxy)-1-(1-(E)-pentenyl)benzene, 4-(4-pentylphenoxy)-1-(1-(E)-pentenyl)benzene, 4-(4-hexylphenoxy)-1-(1-(E)-pentenyl)benzene, 4-(4-propylphenoxy)-1-(1-(E)-propenyl)benzene, 4-(4-propylphenoxy)-1-(1-(E)-butenyl)benzene, 4-(4-propylphenoxy)-1-(1-(E)-pentenyl)benzene, 4-(4-propylphenoxy)-1-(1-(E)-hexenyl)benzene, 4-(4-propylphenoxy)-1-(1-(E)-heptenyl)benzene, 4-(4-propylphenoxy)-1-(1-(E)-octenyl)benzene, 4-(4-trifluoromethylphenoxy)-1-(1-(E)-pentenyl)benzene, (4-(1-(E)-propenyl))phenyl-(4-propyl)benzoate, (4-(1-(E)-butenyl))phenyl-(4-propyl)benzoate, (4-(1-(E)-pentenyl))phenyl-(4-propyl)benzoate, (4-(1-(E)-hexenyl))phenyl-(4-propyl)benzoate, (4-(1-(E)-heptenyl))phenyl-(4-propyl)benzoate, (4-(1-(E)-octenyl))phenyl-(4-propyl)benzoate, (4-(1-(E)-pentenyl))phenyl-(4-methyl)benzoate, (4-(1-(E)-pentenyl))phenyl-(4-ethyl)benzoate, (4-(1-(E)-pentenyl))phenyl-(4-propyl)benzoate, (4-(1-(E)-pentenyl))phenyl-(4-butyl)benzoate, (4-(1-(E)-pentenyl))phenyl-(4-pentyl)benzoate, (4-(1-(E)-propenyl))phenyl-(4-(4-propylcyclohexyl))benzoate, (4-(1-(E)-butenyl))phenyl-(4-(4-propylcyclohexyl))benzoate, (4-(1-(E)-pentenyl))phenyl-(4-(4-propylcyclohexyl))benzoate, (4-(1-(E)-hexenyl))phenyl-(4-(4-propylcyclohexyl))benzoate, (4-(1-(E)-heptenyl))phenyl-(4-(4-propylcyclohexyl))benzoate, (4-(1-(E)-octenyl))phenyl-(4-(4-propylcyclohexyl))benzoate, (4-(1-(E)-pentenyl))phenyl-(4-(4-methylcyclohexyl))benzoate, (4-(1-(E)-pentenyl))phenyl-(4-(4-ethylcyclohexyl))benzoate, (4-(1-(E)-pentenyl))phenyl-(4-(4-butylcyclohexyl))benzoate, (4-(1-(E)-pentenyl))phenyl-(4-(4-pentylcyclohexyl))benzoate, (4-(1-(E)-pentenyl))phenyl-(4-(4-propylcyclohexenyl))benzoate, (4-(1-(E)-pentenyl))phenyl-(4-(4-pentylcyclohexenyl))benzoate, (4-(1-(E)-propenyl))phenyl-(4-cyano-3-fluoro)benzoate, (4-(1-(E)-butenyl))phenyl-(4-cyano-3-fluoro)benzoate, (4-(1-(E)-pentenyl))phenyl-(4-cyano-3-fluoro)benzoate, (4-(1-(E)-hexenyl))phenyl-(4-cyano-3-fluoro)benzoate, (4-(1-(E)-heptenyl))phenyl-(4-cyano-3-fluoro)benzoate, (4-(1-(E)-octenyl))phenyl-(4-cyano-3-fluoro)benzoate, (4-(1-(E)-propenyl))phenyl-(3,4-difluoro)benzoate, (4-(1-(E)-pentenyl))phenyl-(3,4-difluoro)benzoate, (4-(1-(E)-heptenyl))phenyl-(3,4-difluoro)benzoate, (4-(1-(E)-propenyl))phenyl-(3,4,5-trifluoro)benzoate, (4-(1-(E)-pentenyl))phenyl-(3,4,5-trifluoro)benzoate, (4-(1-(E)-heptenyl))phenyl-(3,4,5-trifluoro)benzoate, 4-methylphenyl-(4-(1-(E)-pentenyl))benzoate, 4-ethylphenyl-(4-(1-(E)-pentenyl))benzoate, 4-propylphenyl-(4-(1-(E)-pentenyl))benzoate, 4-butylphenyl-(4-(1-(E)-pentenyl))benzoate, 4-pentylphenyl-(4-(1-(E)-pentenyl))benzoate, 4-hexylphenyl-(4-(1-(E)-pentenyl))benzoate, 4-heptylphenyl-(4-(1-(E)-pentenyl))benzoate, 4-octylphenyl-(4-(1-(E)-nonenyl))benzoate, 4-nonylphenyl-(4-(1-(E)-nonenyl))benzoate, 4-decylphenyl-(4-(1-(E)-nonenyl))benzoate, 4-undecylphenyl-(4-(1-(E)-nonenyl))benzoate, 4-octyloxyphenyl-(4-(1-(E)-nonenyl))benzoate, 4-nonyloxyphenyl-(4-(1-(E)-nonenyl))benzoate, 4-decyloxyphenyl-(4-(1-(E)-nonenyl))benzoate, 4-(4-methylcyclohexyl)phenyl-(4-(1-(E)-pentenyl))benzoate, 4-(4-ethylcyclohexyl)phenyl-(4-(1-(E)-pentenyl))benzoate, 4-(4-propylcyclohexyl)phenyl-(4-(1-(E)-pentenyl))benzoate, 4-(4-butylcyclohexyl)phenyl-(4-(1-(E)-pentenyl))benzoate, 4-(4-pentylcyclohexyl)phenyl-(4-(1-(E)-pentenyl))benzoate, 4-(4-hexylcyclohexyl)phenyl-(4-(1-(E)-pentenyl))benzoate, 4-(4-propylcyclohexyl)phenyl-(4-(1-(E)-propenyl))benzoate, 4-(4-propylcyclohexyl)phenyl-(4-(1-(E)-butenyl))benzoate, 4-(4-propylcyclohexyl)phenyl-(4-(1-(E)-hexynyl))benzoate, 4-(4-propylcyclohexyl)phenyl-(4-(1-(E)-heptenyl))benzoate, 4-(4-propylcyclohexyl)phenyl-(4-(1-(E)-octenyl))benzoate, 4-(4-propylcyclohexenyl)phenyl-(4-(1-(E)-pentenyl))benzoate, 4-(4-cyano-3-fluoro)phenyl-(4-(1-(E)-pentenyl))benzoate, 4-(4-cyano-3-fluoro)phenyl-(4-(1-(E)-heptenyl))benzoate, 4-(3,4-difluoro)phenyl-(4-(1-(E)-pentenyl))benzoate, 4-(3,4-difluoro)phenyl-(4-(1-(E)-heptenyl))benzoate, 4-(3,4,5-trifluoro)phenyl-(4-(1-(E)-pentenyl))benzoate, and 4-(3,4,5-trifluoro)phenyl-(4-(1-(E)-heptenyl))benzoate.

The compound represented by the formula (3C) may preferably be a compound wherein Ring D in the formula (3C) is 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, or 6,3-cyclohexenylene, each of which may optionally be substituted with at least one fluorine atom.

The compound represented by the formula (3C) may be prepared, for example, by a method disclosed in JP-A-7-330636 or JP-A-8-99917.

In the formula (3D), $B^1$ to $B^{12}$ each independently stands for a hydrogen atom, a fluorine atom, or an alkyl or alkoxy group having 1 to 10 carbon atoms. At least one of $B^1$ to $B^{12}$ is an alkyl or alkoxy group having 1 to 10 carbon atoms. $R^7$ and $R^8$ each independently stands for a hydrogen atom, a fluorine atom, a cyano group, a4-$R^9$-(cycloalkyl) group, a4-$R^9$-(cycloalkenyl) group, or a $R^{10}$—(O)q group, wherein $R^9$ stands for a hydrogen atom or a straight or branched alkyl group having 1 to 12 carbon atoms optionally substituted with at least one fluorine atom, $R^{10}$ stands for a straight or branched alkyl group having 1 to 12 carbon atoms optionally substituted with at least one fluorine atom; and q is 0 or 1.

Examples of $R^7$ and $R^8$ in the formula (3D) may include a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkoxy-alkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group; a 4-alkyl-cycloalkyl group such as a 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkyl-cycloalkyl group substituted with at least one fluorine atom, i.e., a 4-fluoroalkyl-cycloalkyl group; a 4-alkyl-cycloalkenyl group such as a 4-propylcyclohexenyl or 4-pentylcyclohexenyl group, or a 4-alkyl-cycloalkenyl group substituted with at least one fluorine atom, i.e., a 4-fluoroalkyl-cycloalkenyl group; and a cyano group.

Preferred examples of the phenylacetylene compound represented by the formula (3D) may include compounds represented by the following formulae, wherein $R^7$ and $R^8$ each independently stands preferably for one of the above examples, but are not limited thereto.

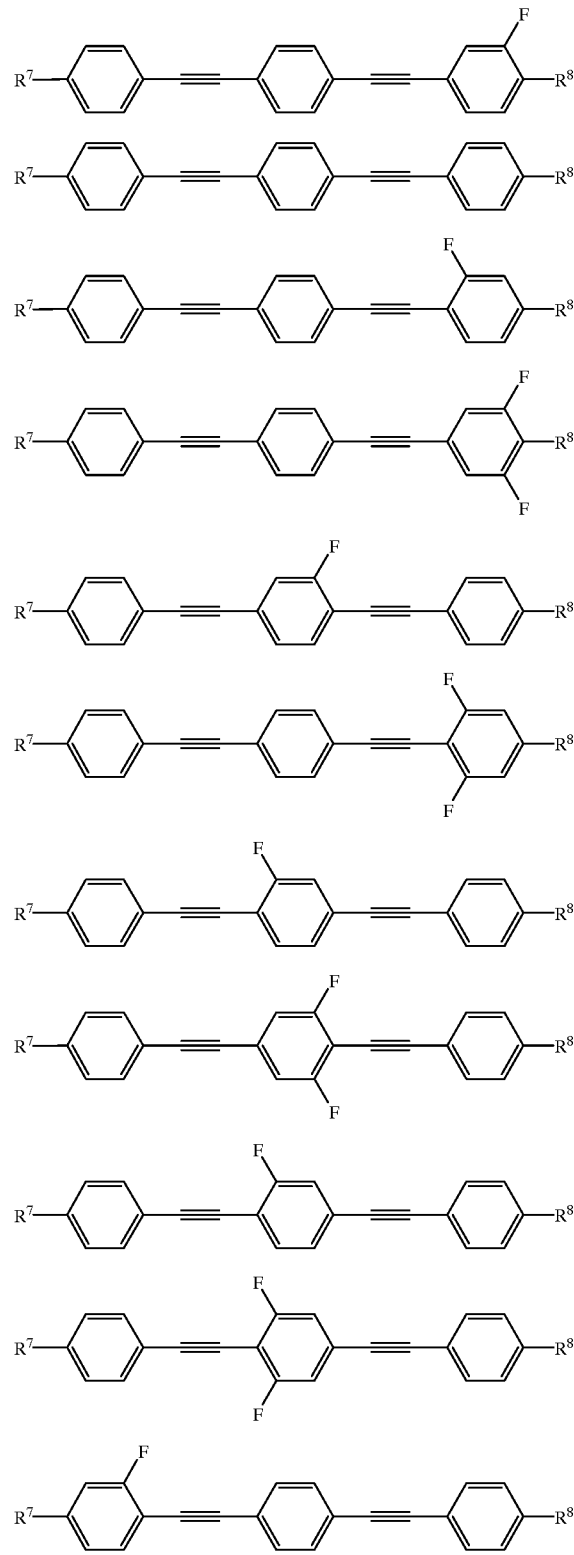

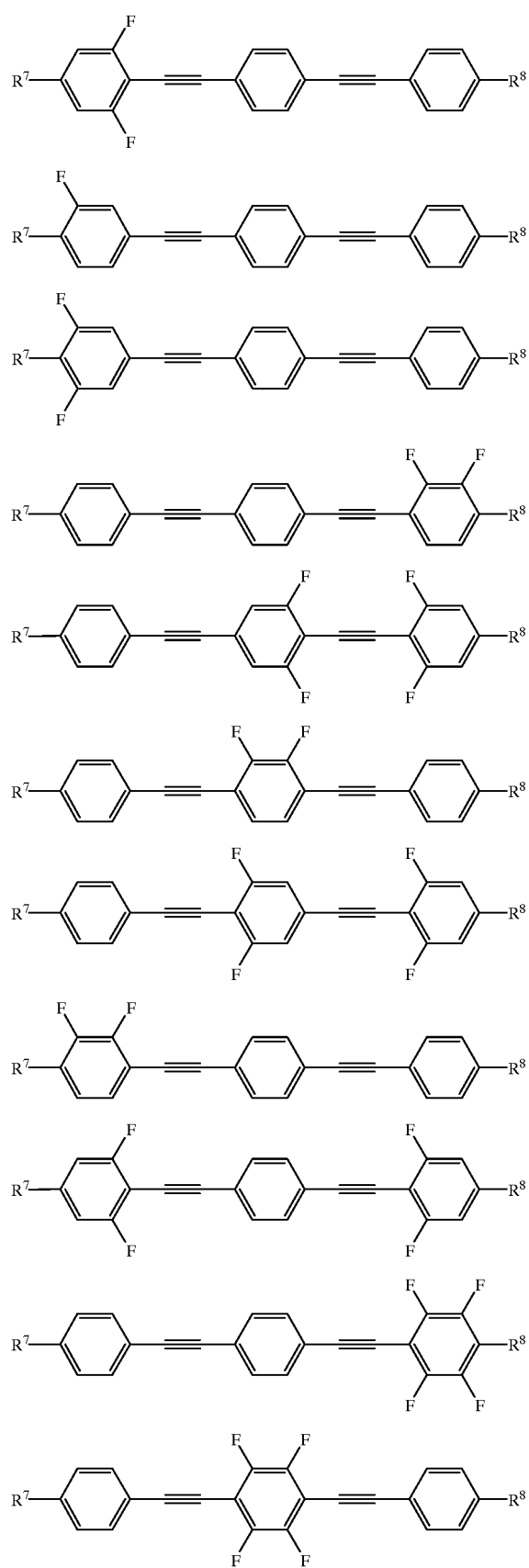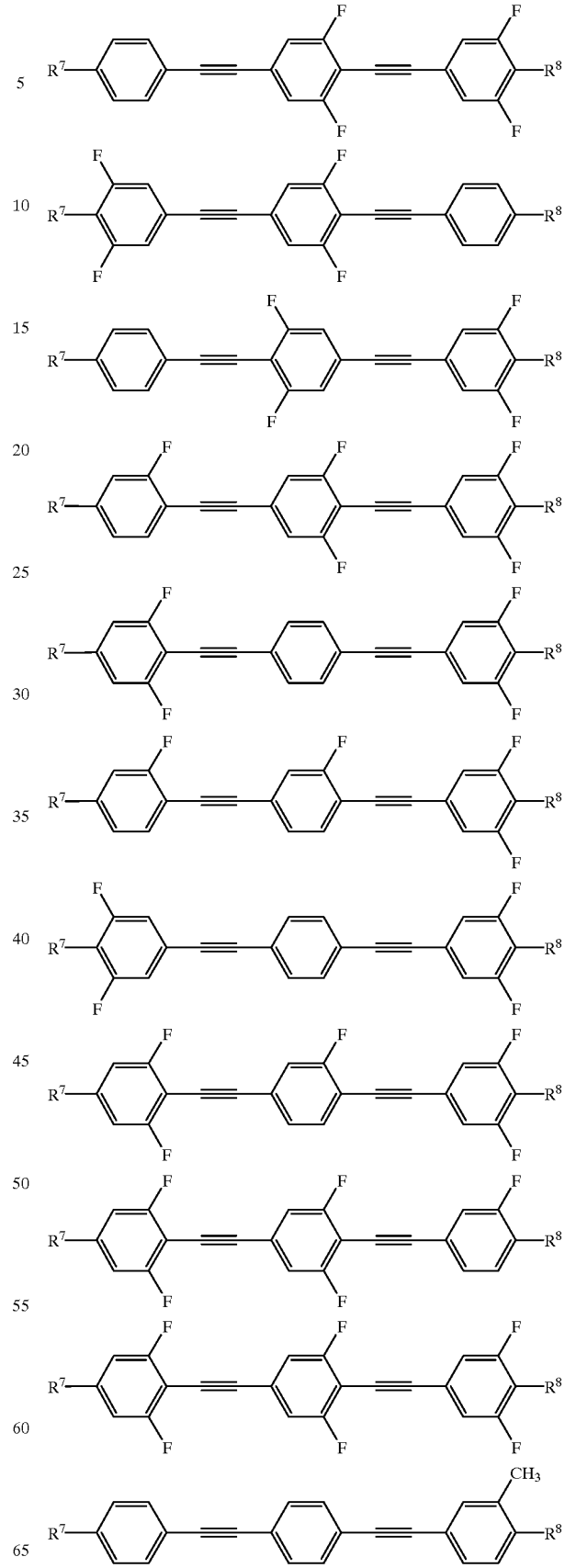

101
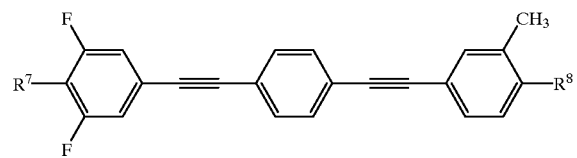
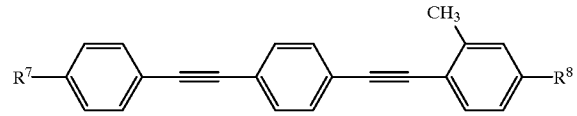
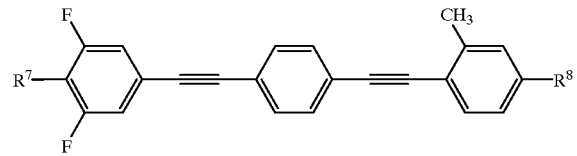
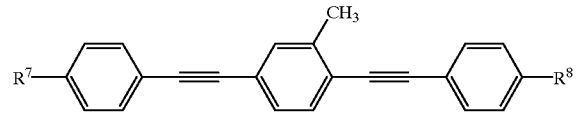
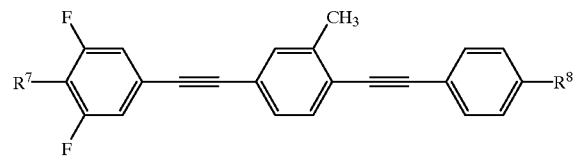
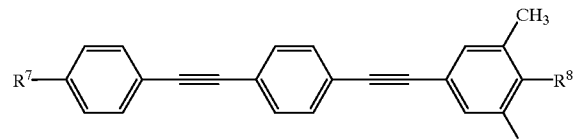
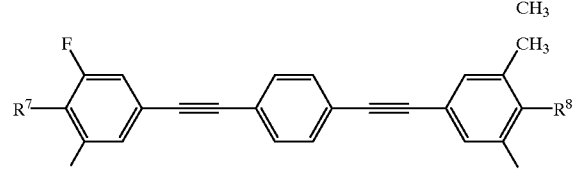
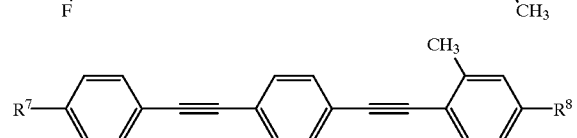
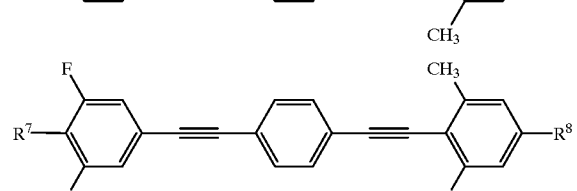
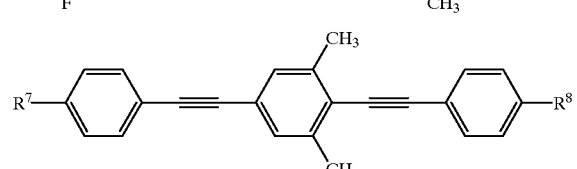
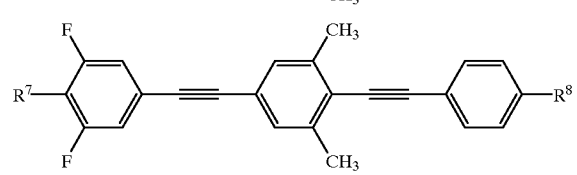
102
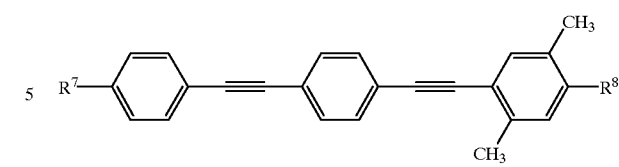
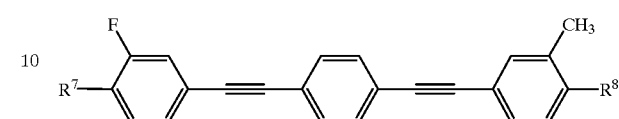
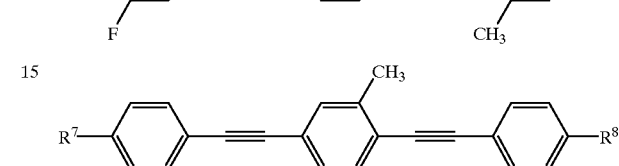
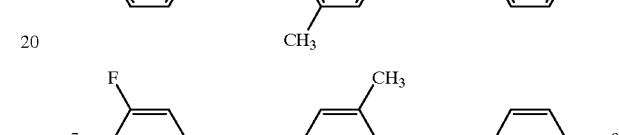
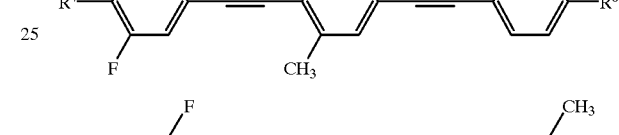
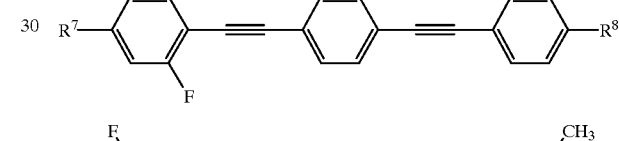
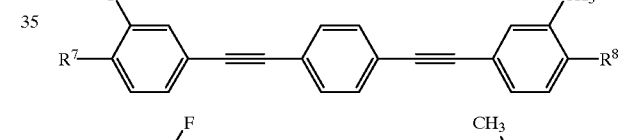
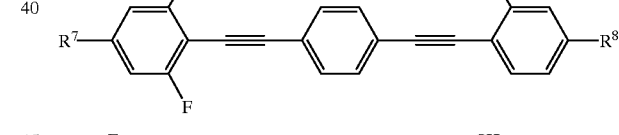
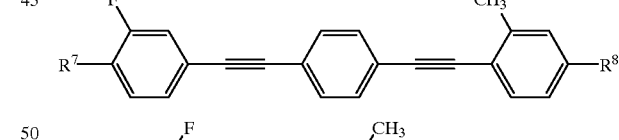
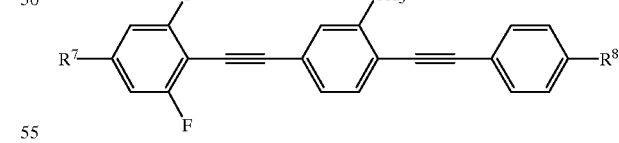
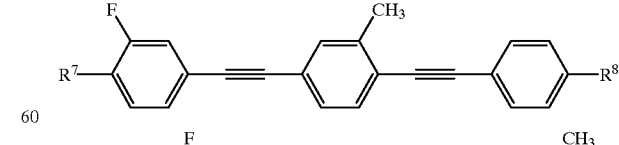
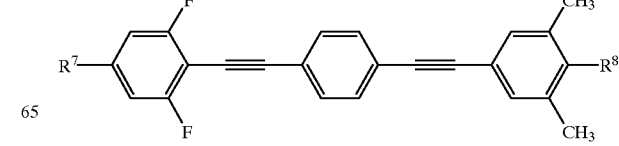

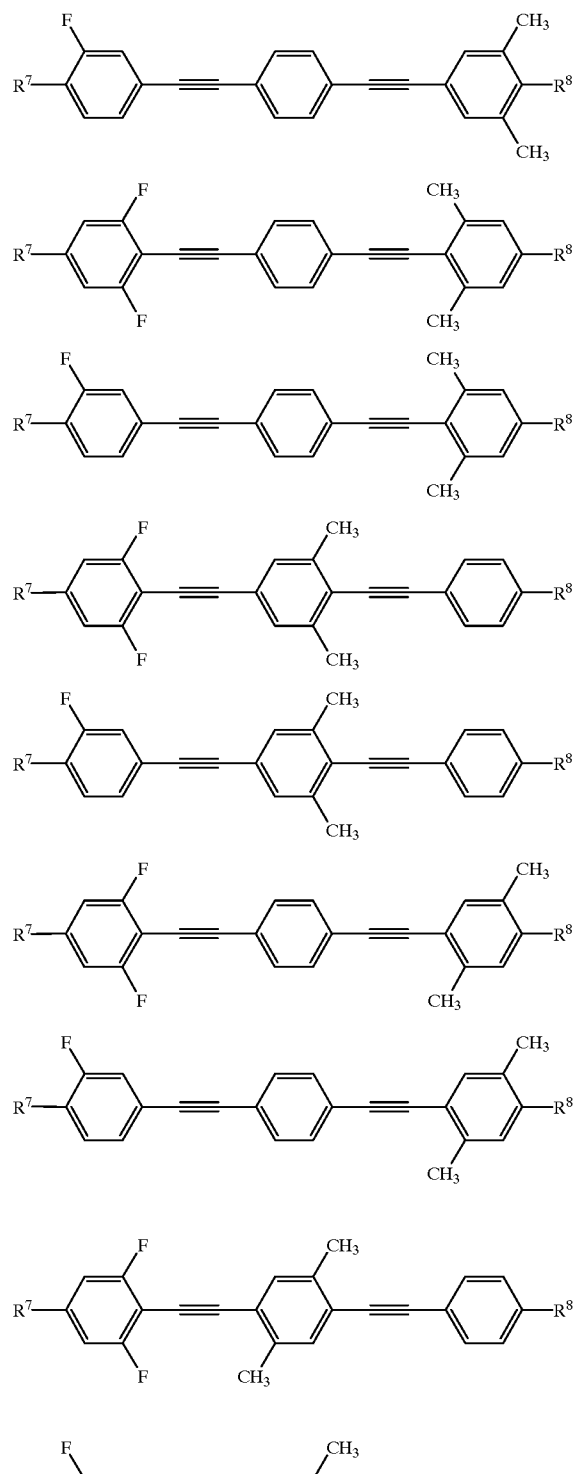
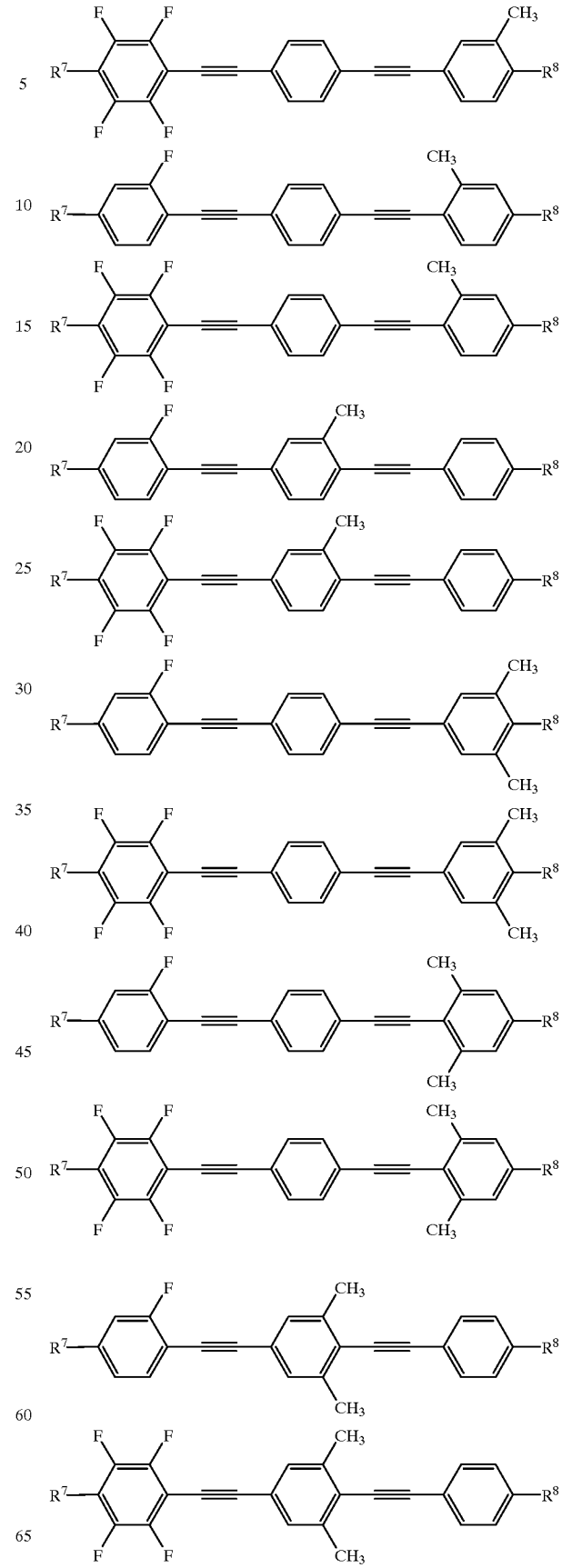

105
-continued
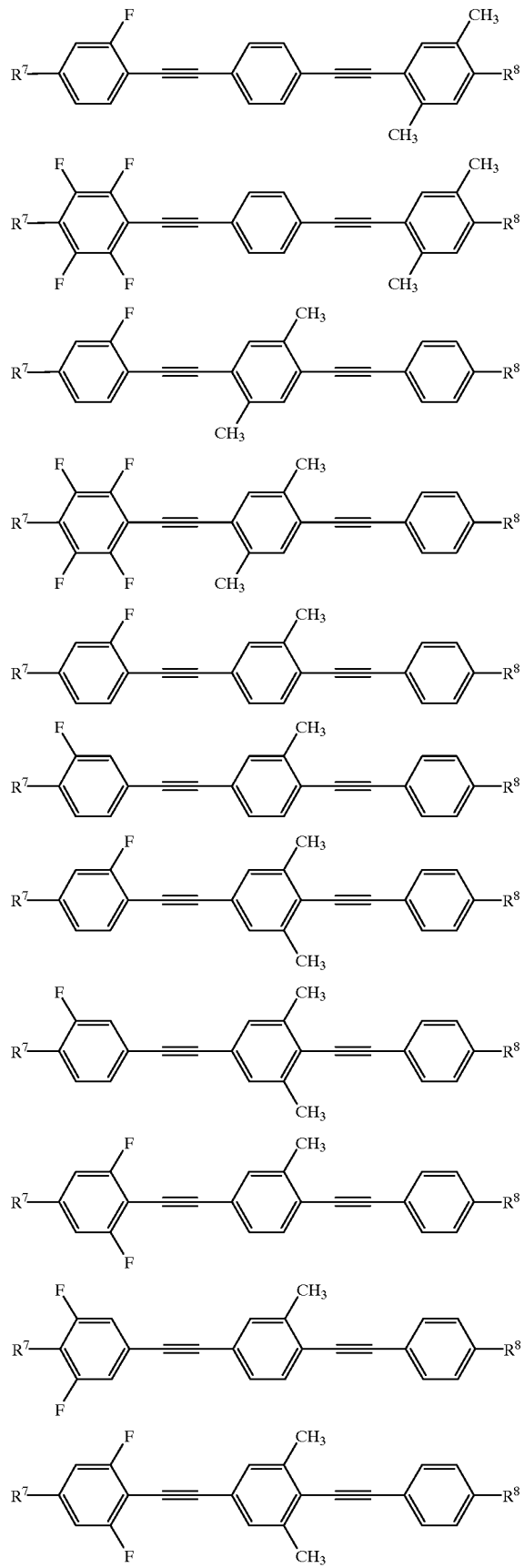
106
-continued
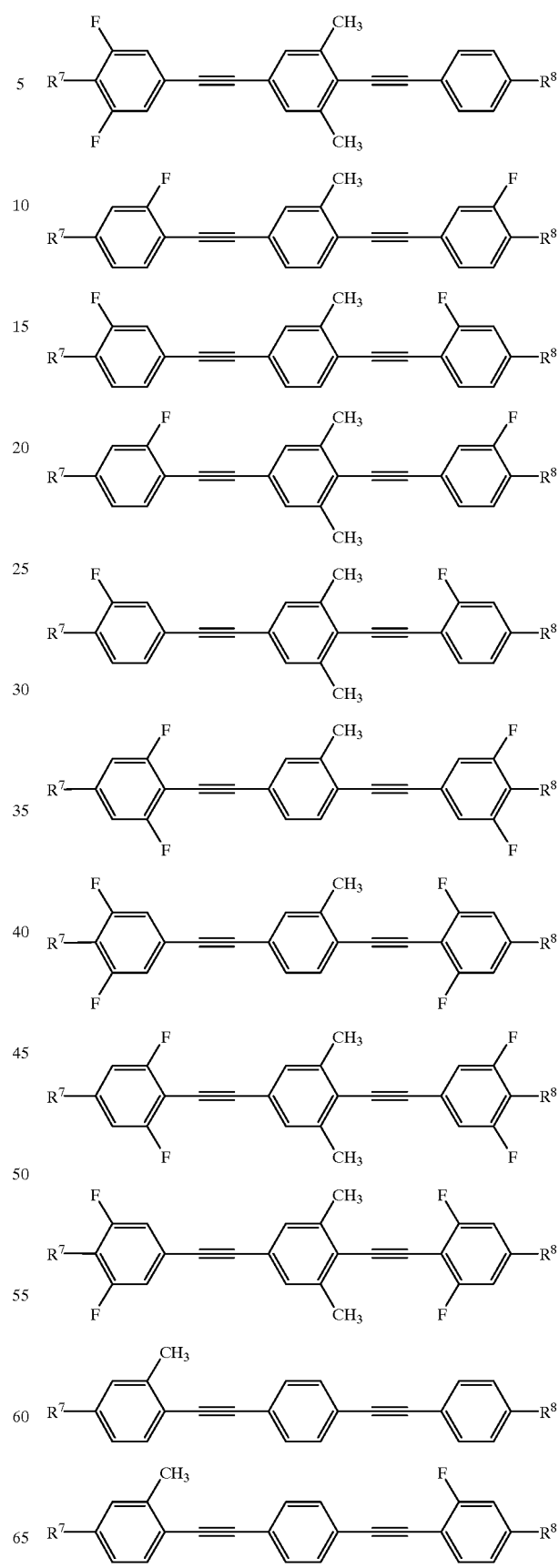

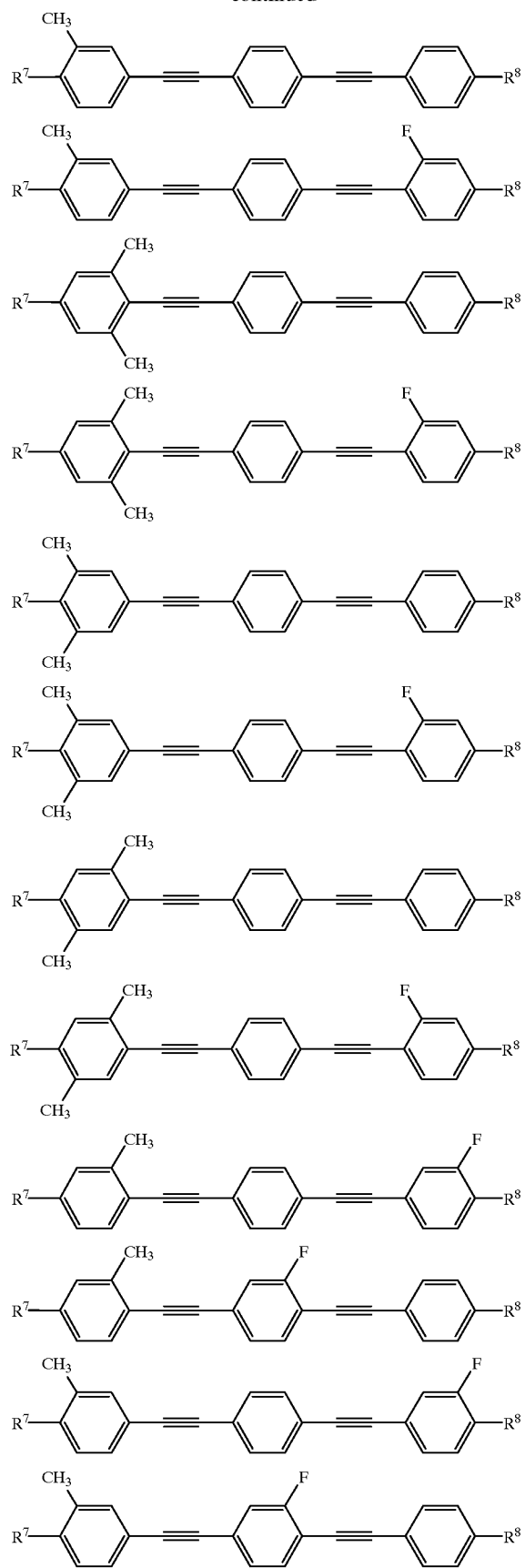
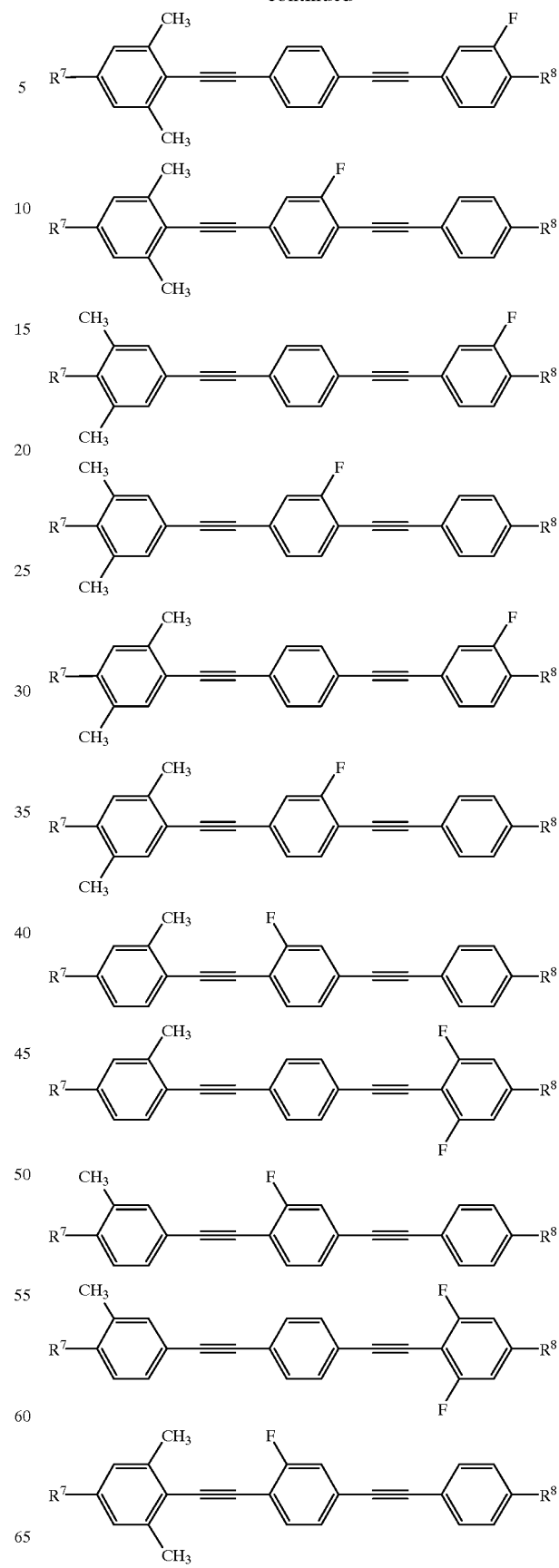

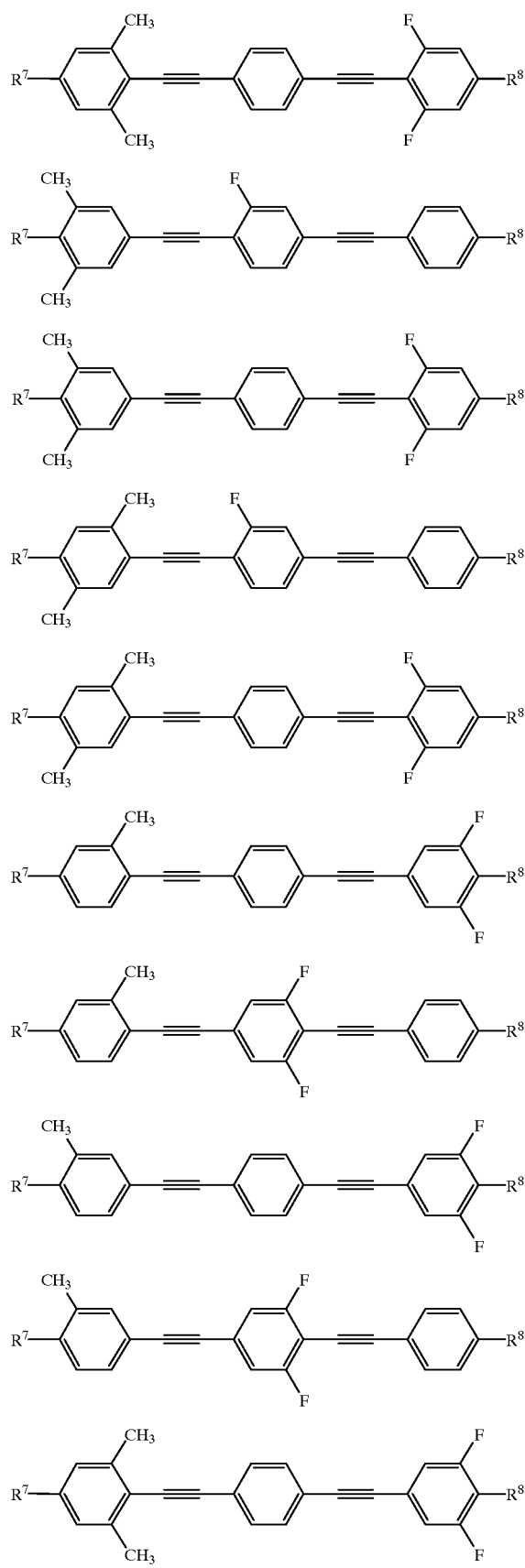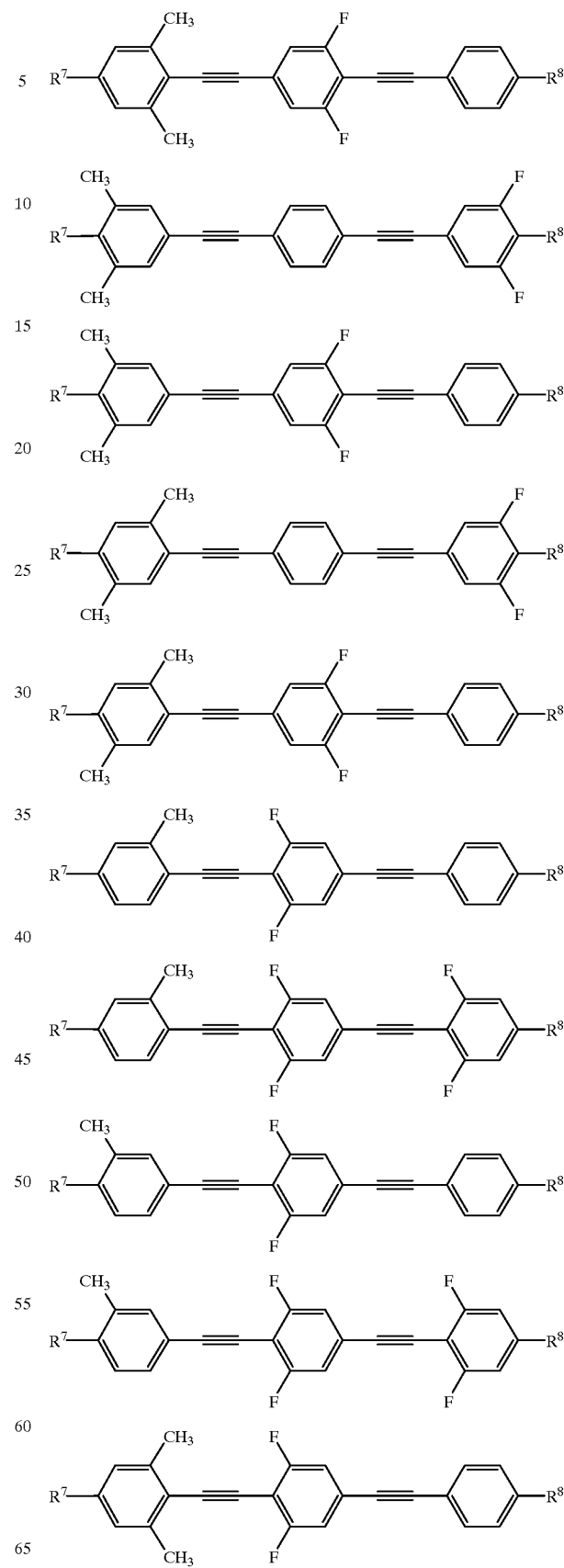

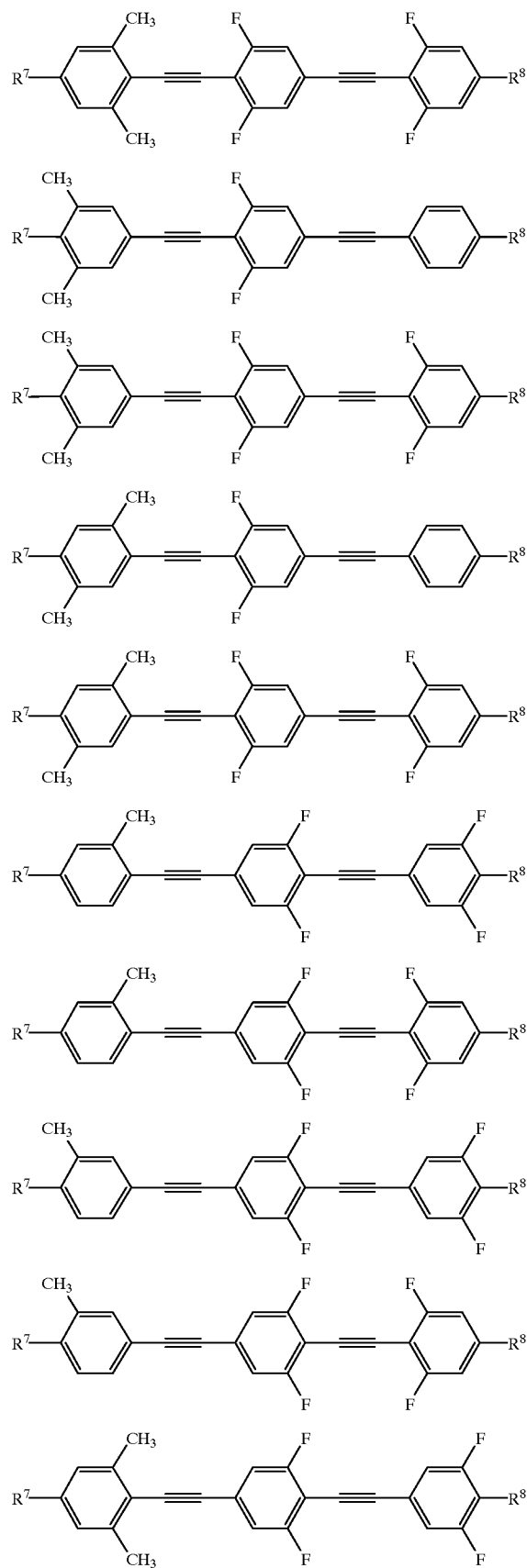

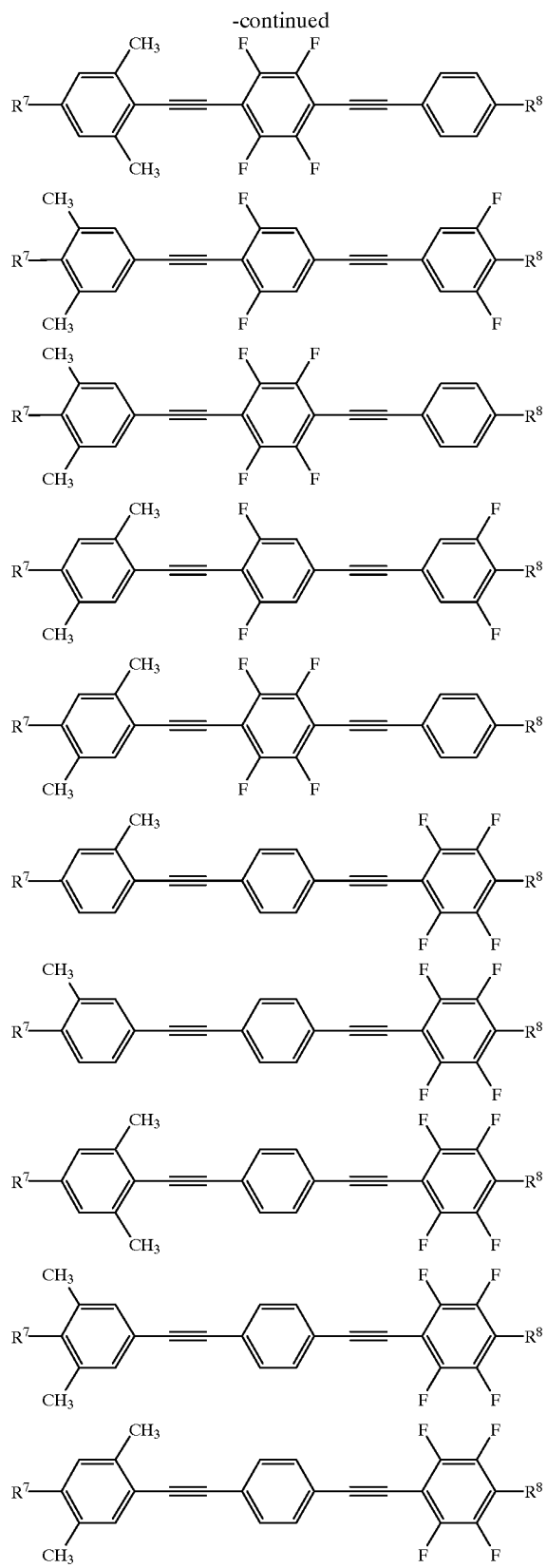

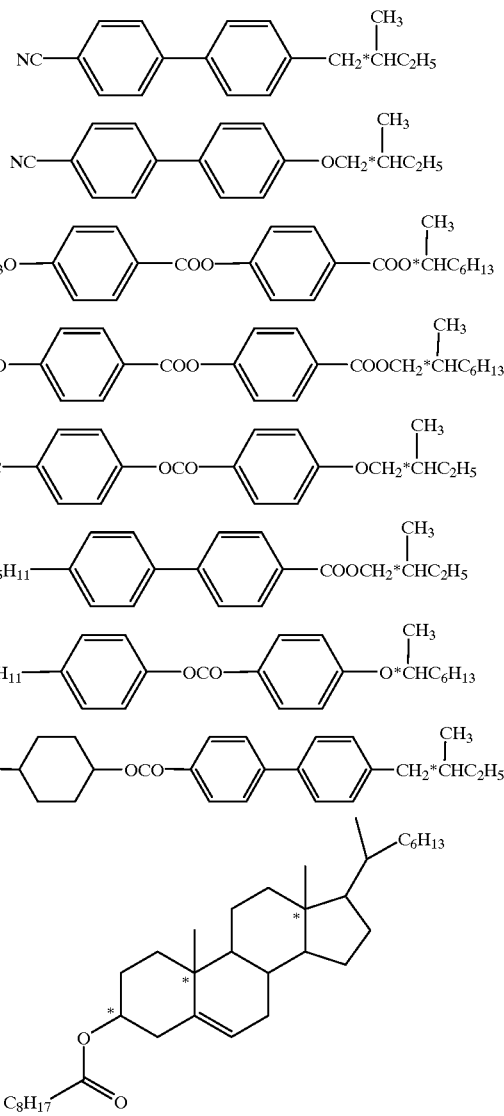

of the total amount of the compounds represented by the formula (3A) is preferably 5 to 90 mol %, and that of the total amount of the compounds represented by the formulae (3B), (3C), and (3D) is preferably 10 to 95 mol %.

The liquid crystal composition of the present invention may further contain one or more chiral compounds as a twisting agent. The chiral compound is not particularly limited, and preferred examples of this compound may include the following compounds, wherein * denotes an asymmetric carbon:

In the liquid crystal composition of the present invention, the content of the chiral compound is not particularly limited and may suitably be selected depending on the composition or the like conditions.

The liquid crystal element according to the present invention is not particularly limited as long as the element includes the liquid crystal composition as mentioned above held between a pair of electrode substrates, and an element having a structure similar to that of conventional liquid crystal elements may be employed. The kind and configuration of the electrodes are not particularly limited, and conventional electrodes may be used. The liquid crystal element of the present invention may be manufactured In the liquid crystal composition of the present invention, the compositional ratio (mole percentage of each component based on 100 mol % of the total amount of the composition)

generally in accordance with the fabrication process of conventional liquid crystal elements, and additional components may also be provided as desired.

EXAMPLES

The present invention will now be explained in detail with reference to the examples, but the present invention is not limited thereto.

In the examples, properties of the liquid crystal compositions were measured in accordance with the following method:
1) the refractive index anisotropy (Δn) was measured by injecting a sample into a wedge-shaped cell having the apex angle of 1.6°, aligning the liquid crystal molecules, irradiating the cell with He—Ne laser, and measuring the refraction angle of the laser.
2) The upper critical temperature (TNI) and the lower critical temperature (m.p.) of the nematic (N) phase of a liquid crystal composition were measured under a polarization microscope.

Example 1-1

A flask equipped with a stirrer and a thermometer was charged with 9.60 g of intermediate (M1-1) shown below, 0.29 g of dichlorobis(triphenylphosphine)palladium, 6.63 g of triethyl amine, and 57.6 g of N,N-dimethylformamide (DMF) under a nitrogen atmosphere, and heated up to 60° C. Then 3.48 g of intermediate (M1-2) shown below dissolved in 7.0 g of DMF was added dropwise, and the resulting mixture was stirred at 60 to 65° C. for 3 hours. After the completion of the reaction, the reaction mass was cooled down to room temperature, diluted with ethylacetate and hexane, and washed with water. The organic phase was separated, washed twice with water, and concentrated. The concentrate was purified through silica gel chromatography using a 10/1 (by volume) mixture of hexane/ethylacetate mixed with 0.1 wt % triethyl amine as an eluting solvent. The resulting product was recrystallized repeatedly from ethanol and hexane, to thereby obtain 4.76 g of the objective compound.

The $^1$H-NMR spectrum data of the resulting compound was determined, from which the compound was identified as compound (1A-1) having the following structure:

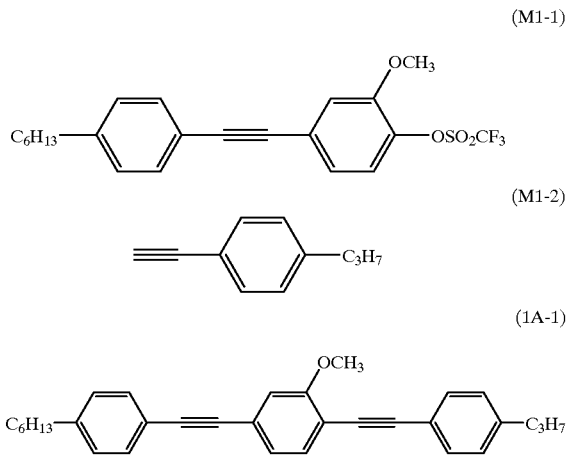

The intermediates (M1-1) and (M1-2) had been synthesized in accordance with the following process:

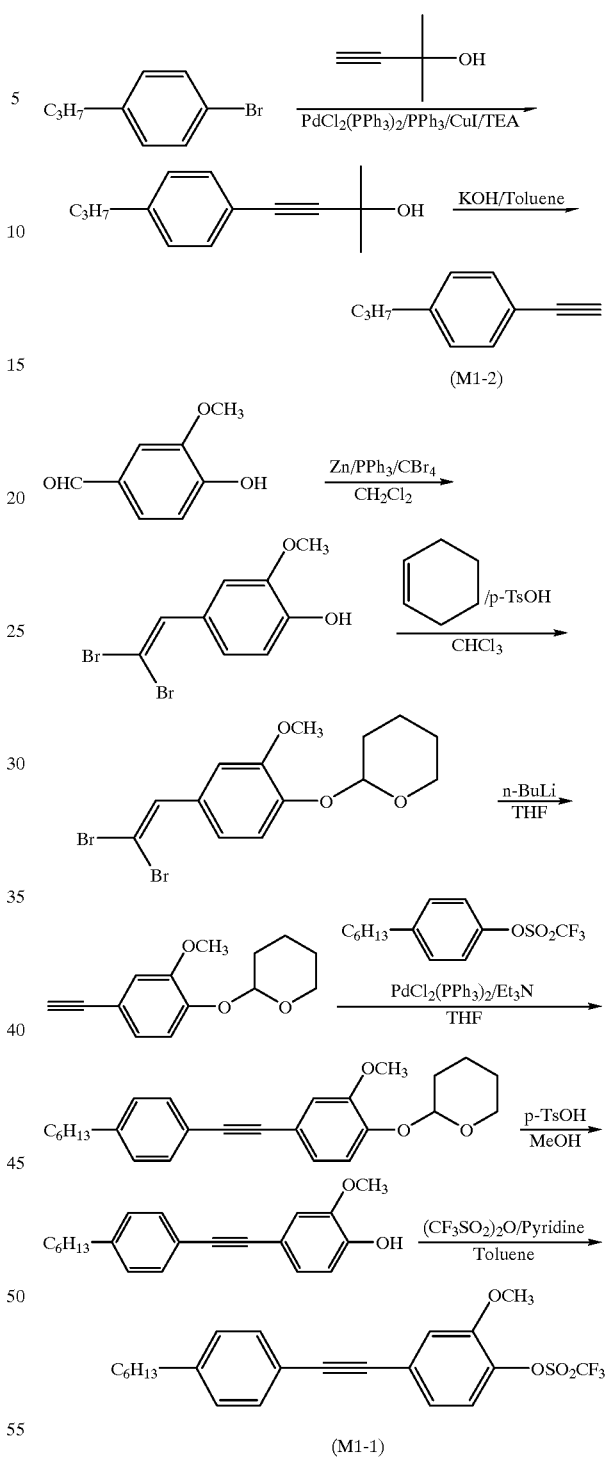

The $^1$H-NMR spectrum data of the compound (1A-1) were as follows:

$^1$H-NMR (δ): 0.88(t,3H,J=7.3 Hz),0.93(t,3H,J=7.3 Hz), 1.20–1.40(m,6H),1.53–1.71(m,4H),2.59(t,2H,J=7.1 Hz), 2.61(t,2H,J=7.1 Hz),3.93(s,3H),7.03–7.18(m,6H), 7.42–7.48(m,5H)

The phase sequence of the compound (1A-1) was evaluated through a polarization microscopic observation. The compound exhibited a crystalline phase below 86° C., a nematic phase in the range of 86 to 108° C., and an isotropic phase over 108° C. It was thus determined that this compound was a liquid crystalline compound.

Further, 10 wt % of the compound (1A-1) was added to a nematic composition MJ931381 (manufactured by Merck Japan Co.) and the refractive index anisotropy Δn was determined, from which Δn of the compound was extrapolated based on the concentration. It was determined that the Δn of the compound was 0.39, which is an extremely large value. Δn was measured with an Abbe refractometer at 20° C. and at the wavelength of 589 nm.

The phenylacetylene compound having an alkoxy group bound to its skeleton in accordance with the present invention, as well as the liquid crystal composition containing this compound, is large in refractive index anisotropy, stable, and easy to mix with other liquid crystals, and thus is particularly useful as a material for liquid crystal elements such as STN (supertwisted nematic) liquid crystal elements or PDLC (polymer dispersed liquid crystal) elements.

Example 2-1

(Step 1-1)

A flask equipped with a stirrer and a thermometer was charged with a mixed solution of 25.95 g of 4-bromophenol, 0.01 g of p-toluenesulfonic acid, and 103.8 g of chloroform under a nitrogen atmosphere, and stirred in an ice bed. Then a solution of 15.14 g of 3,4-dihydro-2H-pyran and 15.1 g of chloroform was added dropwise under stirring at a temperature not higher than 5° C. After all the solution was added dropwise, the resulting mixture was stirred for 2 hours at the same temperature, neutralized with 2 g of triethyl amine, and concentrated at 60° C. under a pressure of 20 Torr. The concentrate was purified through silica gel chromatography using a 20/1 (by volume) mixture of hexane/ethylacetate mixed with 0.1 wt % of triethyl amine as an eluting solvent, to thereby obtain 38.07 g of 1-bromo-4-perhydro-2H-pyrane-2-yl oxybenzene at 99% yield.

(Step 1-2)

In a flask equipped with a stirrer and a thermometer, 25.01 g of 1-bromo-4-perhydro-2H-pyrane-2-yl oxybenzene prepared in Step 1-1, 0.46 g of tetrakis(triphenylphosphine) palladium, and 15.30 g of (1E)hept-1-enoylboronate were dissolved in a mixed solution of 75 g of toluene and 30 g of ethanol under a nitrogen atmosphere, and heated up to 78° C. under stirring. Then 144.4 g of a 7.5 wt % aqueous solution of sodium carbonate was added dropwise at 78 to 79° C. over 2 hours.

The resulting mixture was refluxed under heating at 79° C. for 1 hour, and cooled down to room temperature. The organic phase was extracted with toluene and water, washed three times with water, and concentrated at 60° C. under a pressure of 20 Torr. The concentrate was purified through silica gel chromatography using a 20/1 (by volume) mixture of hexane/ethylacetate mixed with 0.1 wt % triethyl amine as an eluting solvent, to thereby obtain 24.50 g of 2-(4-((1E)hept-1-enoyl)phenoxy)perhydro-2H-pyrane at 92% yield.

(Step 1-3)

In a flask equipped with a stirrer and a thermometer, 18.50 g of 2-(4-((1E)hept-1-enoyl)phenoxy)perhydro-2H-pyrane prepared in Step 1-2, 19.86 g of diiodomethane, 26.07 g of copper-zinc (1:1 by weight) alloy, and 0.01 g of iodine were suspended in a mixed solution of 37 g of toluene and 15 g of diethylether under a nitrogen atmosphere, and the suspension was heated up to 40° C. under stirring. The resulting mass was further stirred at the same temperature for 19 hours, and concentrated at 60° C. under a pressure of 20 Torr. Then the concentrate was purified through silica gel chromatography using a 20/1 (by volume) mixture of hexane/ethylacetate mixed with 0.1 wt % triethyl amine as an eluting solvent, to thereby obtain a mixture of 2-(4-(2-pentylcyclopropyl)phenoxy)perhydro-2H-pyrane and unreacted 2-(4-((1E)hept-1-enoyl)phenoxy)perhydro-2H-pyrane. This mixture was dissolved in 30 g of methanol at room temperature, mixed with 0.1 g of p-toluenesulfonic acid, and stirred overnight. Then the resulting mixture was neutralized with 2 g of triethyl amine, and concentrated at 60° C. under a pressure of 20 Torr. The concentrate was purified through silica gel chromatography using a 20/1 (by volume) mixture of hexane/ethylacetate mixed with 0.1 wt % triethyl amine as an eluting solvent, to thereby obtain 7.39 g of a mixture of 4-(2-pentylcyclopropyl)phenol and 4-((1E) hept-1-enoyl)phenol.

(Step 1-4)

In a flask equipped with a stirrer and a thermometer, 5.70 g of the mixture of 4-(2-pentylcyclopropyl)phenol and 4-((1E)hept-1-enoyl)phenol prepared in Step 1-3, 0.11 g of 4-pyrrolidinopyridine, and 11.40 g of pyridine were dissolved in 28.5 g of toluene under a nitrogen atmosphere, and cooled down to −3° C. under stirring. Then a solution of 11.81 g of trifluoromethanesulfonic acid anhydride and 17.7 g of toluene was added dropwise at a temperature not higher than 0° C. over 1 hour, and stirred overnight at the same temperature. After the reaction was terminated by adding water to the reaction mass, the organic phase was extracted with toluene, washed three times with water, and concentrated at 60° C. under a pressure of 20 Torr. The concentrate was purified through silica gel chromatography using hexane as an eluting solvent, to thereby obtain 6.90 g of a mixture of 4-(2-pentylcyclopropyl)phenyl (trifluoromethyl) sulfonate and 4-((1E)hept-1-enoyl)phenyl(trifluoromethyl) sulfonate.

(Step 2-1)

The process of Step 1-1 was followed except that 4-bromophenol was replaced with 4-iodo-2-methylphenol, to thereby obtain 1-iodo-4-perhydro-2H-pyrane-2-yloxy-3-methylbenzene at 99% yield.

(Step 2-2)

In a flask equipped with a stirrer and a thermometer, 13.36 g of 1-iodo-4-perhydro-2H-pyrane-2-yloxy-3-methylbenzene prepared in Step 2-1, 0.24 g of dichlorobis (triphenylphosphine)palladium, 0.24 g of triphenylphosphine, 0.12 g of copper iodide (I), and 12.75 g of triethyl amine were suspended in 50 g of ethylacetate under a nitrogen atmosphere, and heated up to 58° C. under stirring. Then a solution of 6.20 g of trimethylsilylacetylene and 6.20 g of ethylacetate was added dropwise at 58 to 64° C. over 2 hours. The resulting mixture was stirred at the same temperature for 3 hours, cooled down to room temperature, and filtered. The residue was washed with ethylacetate, and the resulting filtrate was concentrated at 60° C. under a pressure of 20 Torr. The concentrate was purified through silica gel chromatography using hexane mixed with 0.1 wt % triethyl amine as an eluting solvent, to thereby obtain 11.87 g of 2-(4-(trimethylsilylethynyl)-2-methylphenoxy)perhydro-2H-pyrane at 98% yield.

(Step 2-3)

In a flask equipped with a stirrer and a thermometer, 11.87 g of 2-(4-(trimethylsilylethynyl)-2-methylphenoxy) perhydro-2H-pyrane prepared in Step 2-2 and 0.13 g of potassium carbonate were suspended in 50 g of methanol under a nitrogen atmosphere, stirred at room temperature for 7 hours, and concentrated at 60° C. under a pressure of 20 Torr. The concentrate was purified through silica gel chromatography using a 20/1 (by volume) mixture of hexane/ ethylacetate mixed with 0.1 wt % triethyl amine as an eluting solvent, to thereby obtain 8.10 g of 2-(4-ethynyl-2-methylphenoxy)perhydro-2H-pyrane at 91% yield.
(Step 3-1)

In a flask equipped with a stirrer and a thermometer, 41.0 g of 1-bromo-4-pentyloxybenzene, 0.82 g of dichlorobis(triphenylphosphine)palladium, 0.82 g of triphenylphosphine, 0.41 g of copper iodide (I), and 68.3 g of triethyl amine were suspended in 164 g of ethylacetate under a nitrogen atmosphere, and heated up to 60° C. under stirring. Then 21.3 g of 1-butyne-3-ol was added dropwise at 60 to 65° C. over 1 hour, and stirred at the same temperature for 10 hours. The resulting mixture was cooled down to room temperature, and filtered. The residue was washed with ethylacetate, and the resulting filtrate was concentrated at 60° C. under a pressure of 20 Torr. The concentrate was purified through silica gel chromatography using a 5/1 (by volume) mixture of hexane/ethylacetate as an eluting solvent, to thereby obtain 21.0 g of 1-butyne-1-(4-pentyloxyphenyl)-3-ol at 51% yield.
(Step 3-2)

In a flask equipped with a stirrer and a thermometer, 21.0 g of 1-butyne-1-(4-pentyloxyphenyl)-3-ol prepared in Step 3-1 and 1.0 g of potassium hydroxide were suspended in 84 g of toluene under a nitrogen atmosphere, stirred at 90° C. for 4 hours, and concentrated at 50° C. under a pressure of 20 Torr. The concentrate was purified through silica gel chromatography using hexane mixed with 0.1 wt % triethyl amine as an eluting solvent, to thereby obtain 14.0 g of 4-pentyloxyphenylacethylene at 88% yield.
(Step 4-1)

A flask equipped with a stirrer and a thermometer was charged with 6.90 g of a mixture of 4-(2-pentylcyclopropyl)phenyl(trifluoromethyl)sulfonate and 4-((1E)hept-1-enoyl)phenyl(trifluoromethyl)sulfonate prepared in Step 4-1, 0.28 g of dichlorobis(triphenylphosphine)palladium, 8.30 g of triethyl amine, and 34.5 g of N,N-dimethylformamide (DMF) under a nitrogen atmosphere, and heated up to 56° C. Then 8.10 g of 2-(4-ethynyl-2-methylphenoxy)perhydro-2H-pyrane prepared in Step 2-3 dissolved in 8.10 g of DMF was added dropwise at 56 to 63° C. over 1 hour, and stirred at the same temperature for 6 hours. After the reaction was terminated by adding water to the reaction mass, the organic phase was extracted with toluene, washed with water, and concentrated. The concentrate was purified through silica gel chromatography using a 20/1 (by volume) mixture of hexane/ethylacetate mixed with 0.1 wt % triethyl amine as an eluting solvent.

The resulting purified product was dissolved in 40 g of methanol at room temperature, mixed with 0.01 g of p-toluenesulfonic acid, and stirred overnight. The resulting mixture was neutralized with 2 g of triethyl amine and concentrated at 60° C. under a pressure of 20 Torr. The concentrate was purified through silica gel chromatography using a 20/1 (by volume) mixture of hexane/ethylacetate mixed with 0.1 wt % triethyl amine as an eluting solvent, to thereby obtain 5.18 g of a mixture of 4-(4-(2-pentylcyclopropyl)phenylethynyl)-2-methylphenol and 4-(4-((1E)hept-1-enoyl)phenylethynyl)-2-methylphenol.
(Step 4-2)

A flask equipped with a stirrer and a thermometer was charged with 5.17 g of the mixture of 4-(4-(2-pentylcyclopropyl)phenylethynyl)-2-methylphenol and 4-(4-((1E)hept-1-enoyl)phenylethynyl)-2-methylphenol prepared in Step 4-1, 0.10 g of 4-pyrrolidinopyridine, 10.34 g of pyridine, and 25.9 g of toluene under a nitrogen atmosphere, and cooled down to 2° C. under stirring. Then 6.87 g of trifluoromethanesulfonic acid anhydride dissolved in 10.3 g of toluene was added dropwise at 2 to 5° C. over 1.5 hours, and stirred at the same temperature overnight. After the reaction was terminated by adding water to the reaction mass, the organic phase was extracted with toluene, washed with water, and concentrated. The concentrate was purified through silica gel chromatography using a 20/1 (by volume) mixture of hexane/ethylacetate as an eluting solvent, to thereby obtain 4.80 g of a mixture of 4-(4-(2-pentylcyclopropyl)phenylethynyl)-2-methylphenyl(trifluoromethyl)sulfonate and 4-(4-((1E)hept-1-enoyl)phenylethynyl)-2-methylphenyl(trifluoromethyl)sulfonate.
(Step 4-3)

A flask equipped with a stirrer and a thermometer was charged with 1.35 g of the mixture of 4-(4-(2-pentylcyclopropyl)phenylethynyl)-2-methylphenyl(trifluoromethyl)sulfonate and 4-(4-((1E)hept-1-enoyl)phenylethynyl)-2-methylphenyl(trifluoromethyl)sulfonate prepared in Step 4-2, 0.05 g of dichlorobis(triphenylphosphine)palladium, 13.5 g of DMF, and 0.91 g of triethyl amine under a nitrogen atmosphere, and heated up to 60 to 65° C. under stirring. Then 0.85 g of 4-pentyloxyphenylacetylene prepared in Step 3-1 dissolved in 1.70 g of DMF was added dropwise at the same temperature over 30 minutes, and stirred at the same temperature for 3 hours. After the reaction was terminated by adding water to the reaction mass, the organic phase was extracted with toluene, washed with water, and concentrated. The concentrate was purified through silica gel chromatography using hexane mixed with 0.1 wt % triethyl amine as an eluting solvent. Then purification through silica gel chromatography using a 40/1 (by volume) mixture of hexane/chloroform mixed with 0.1 wt % triethyl amine as an eluting solvent was repeated, and recrystallization from hexane is repeated, to thereby obtain 0.36 g of the objective compound, 1-(2-(4-(2-(4-((1E)hept-1-enoyl)phenyl)ethynyl)-2-methylphenyl)ethynyl)-4-pentyloxybenzene at 99.5% purity and 0.22 g of the objective compound, 1-(2-(2-methyl-4-(2-(4-(2-pentylcyclopropyl)phenyl)ethynyl)phenyl)ethynyl)-4-pentyloxybenzene at 90.4% purity.

The $^1$H-NMR spectrum data and the structural formula of 1-(2-(4-(2-(4-((1E)hept-1-enoyl)phenyl)ethynyl)-2-methylphenyl)ethynyl)-4-pentyloxybenzene were as follows:

$^1$H-NMR (δ): 0.91(t,3H,J=6.6 Hz),0.94(t,3H,J=6.9 Hz), 1.25–1.55(m, 10H),1.78(qt,2H,J=6.6 Hz),2.21(dt,2H, Jd=6.9 Hz,Jt=6.9 Hz),2.49(s,3H),3.97(t,2H,J=6.6 Hz), 6.27 (dt,1H,Jd=15.8 Hz,Jt=6.9 Hz),6.37(d,1H,J=15.8 Hz), 6.87 (d,2H,J=8.9 Hz),7.26–7.33(m,2H),7.39–7.48(m,5H)

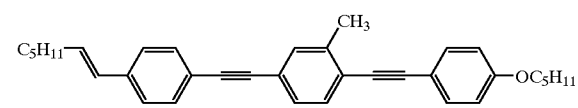

The phase sequence of 1-(2-(4-(2-(4-((1E)hept-1-enoyl)phenyl)ethynyl)-2-methylphenyl)ethynyl)-4-pentyloxybenzene was evaluated through a polarization microscopic observation. The compound exhibited a crystalline phase below 110° C., a nematic phase in the range of 110 to 233° C., and an isotropic phase over 233° C. It was thus determined that this compound was a liquid crystalline compound.

Further, 10 wt % of this compound was added to a nematic composition MJ931381 (manufactured by Merck Japan Co.) and the refractive index anisotropy Δn was determined, from which Δn of the compound was extrapolated based on the concentration. It was determined that the Δn of the compound was 0.49, which is an extremely large value. Δn was measured with an Abbe refractometer at 20° C. and at the wavelength of 589 nm.

The ¹H-NMR spectrum data and the structural formula of 1-(2-(2-methyl-4-(2-(4-(2-pentylcyclopropyl)phenyl) ethynyl)phenyl)ethynyl)-4-pentyloxybenzene were as follows:

¹H-NMR (δ): 0.76–0.84 (m,1H),0.86–0.97 (m,7H), 0.98–1.10(m,1H),1.24–1.50(m,12H),1.56–1.64(m,1H), 1.74–1.84(m,2H),2.49(s,3H),3.97(d,2H,J=6.6 Hz),6.87(d, 2H, J=8.9 Hz),7.00(d,2H,J=8.3 Hz),7.27–7.36(m,1H), 7.37–7.53(m,6H)

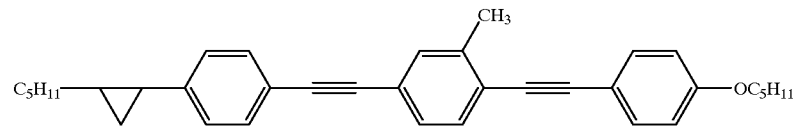

The phase sequence of 1-(2-(2-methyl-4-(2-(4-(2-pentylcyclopropyl)phenyl)ethynyl)phenyl)ethynyl)-4-pentyloxybenzene was evaluated through a polarization microscopic observation. The compound exhibited a crystalline phase below 75° C., a nematic phase in the range of 75 to 170° C., and an isotropic phase over 170° C. It was thus determined that this compound was a liquid crystalline compound.

Further, the Δn of the compound was determined to be 0.40, which is an extremely large value.

Example 2-2

A flask equipped with a stirrer and a thermometer was charged with 1.35 g of the mixture of 4-(4-(2-pentylcyclopropyl)phenylethynyl)-2-methylphenyl (trifluoromethyl)sulfonate and 4-(4-((1E)hept-1-enoyl) phenylethynyl)-2-methylphenyl(trifluoromethyl)sulfonate prepared in Step 4-2, 0.05 g of dichlorobis (triphenylphosphine)palladium, 13.5 g of DMF, and 0.91 g of triethyl amine under a nitrogen atmosphere, and heated up to 53 to 55° C. Then 1.26 g of 4-trifluoro- methoxyphenylacetylene dissolved in 2.70 g of DMF was added dropwise at the same temperature over 2 hours, and stirred for 5 hours. After the reaction was terminated by adding water to the reaction mass, the organic phase was extracted with toluene, washed with water, and concentrated. The concentrate was purified through silica gel chromatography using hexane mixed with 0.1 wt % triethyl amine as an eluting solvent. Then recrystallization from ethanol and hexane was repeated, to thereby obtain 0.19 g of the objective compound, 1-(2-(4-(2-(4-((1E)hept-1-enoyl)phenyl) ethynyl)-2-methylphenyl)ethynyl)-4-trifluoro- methoxybenzene at 99.7% purity, and 0.11 g of the objective compound, 1-(2-(2-methyl-4-(2-(4-(2-pentylcyclopropyl)phenyl) ethynyl)phenyl)ethynyl)-4-trifluoromethoxybenzene at 85.3% purity.

The ¹H-NMR spectrum data and the structural formula of 1-(2-(4-(2-(4-((1E)hept-1-enoyl)phenyl)ethynyl)-2-methylphenyl)ethynyl)-4-trifluoromethoxybenzene were as follows:

¹H-NMR (δ): 0.91(t,3H, J=6.6 Hz),1.30–1.53(m,6H),2.22 (dt,2H,Jd=6.9 Hz,Jt=6.9 Hz),2.49(s,3H),6.27(dt,1H,Jd=15.7 Hz,Jt=6.9 Hz),6.37(d,1H,J=15.7 Hz),7.18–7.58(m, 11H)

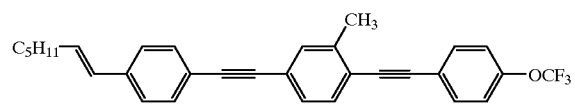

The phase sequence of 1-(2-(4-(2-(4-((1E)hept-1-enoyl) phenyl)ethynyl)-2-methylphenyl)ethynyl)-4-trifluoromethoxybenzene was evaluated through a polarization microscopic observation. The compound exhibited a crystalline phase below 108° C., a smectic phase in the range of 108 to 194° C., a nematic phase in the range of 194 to 224° C., and an isotropic phase over 224° C. It was thus determined that this compound was a liquid crystalline compound.

Further, the Δn of this compound was determined to be 0.45, which is an extremely large value.

The ¹H-NMR spectrum data and the structural formula of 1-(2-(2-methyl-4-(2-(4-(2-pentylcyclopropyl)phenyl) ethynyl)phenyl)ethynyl)-4-trifluoromethoxybenzene were as follows:

¹H-NMR (δ): 0.76–0.84 (m,1H),0.86–0.94(m,4H), 1.05–1.08(m,1H),1.25–1.41(m,8H),1.56–1.64(m,1H),2.49 (s,3H),6.98–7.58(m,11H)

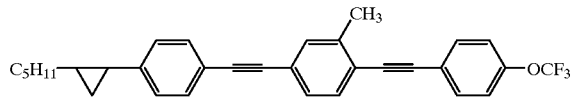

Example 2-3

A flask equipped with a stirrer and a thermometer was charged with 2.00 g of the mixture of 4-(4-(2-pentylcyclopropyl)phenylethynyl)-2-methylphenyl (trifluoromethyl)sulfonate and 4-(4-((1E)hept-1-enoyl) phenylethynyl)-2-methylphenyl(trifluoromethyl)sulfonate prepared in Step 4-2, 0.08 g of dichlorobis (triphenylphosphine)palladium, 20.0 g of DMF, and 1.35 g of triethyl amine under a nitrogen atmosphere, and heated up to 53 to 55° C. Then 2.26 g of p-ethynylbenzonitrile was added, and stirred at the same temperature for 5 hours. After the reaction was terminated by adding water to the reaction mass, the organic phase was extracted with toluene, washed with water, and concentrated. The concentrate was purified through silica gel chromatography using a 10/1 (by volume) mixture of hexane/chloroform mixed with 0.1 wt % triethyl amine as an eluting solvent. Further, recrystallization from methanol and hexane was repeated, to thereby obtain 0.07 g of the objective compound, 4-(2-(4-(2-(4-((1E)hept-1-enoyl)phenyl)ethynyl)-2-methylphenyl)ethynyl) benzonitrile at 98.9% purity, and 0.001 g of the objective compound, 4-(2-(2-methyl-4-(2-(4-(2-pentylcyclopropyl) phenyl)ethynyl)phenyl)ethynyl)benzonitrile at 88.4% purity.

The ¹H-NMR spectrum data and the structural formula of 4-(2-(4-(2-(4-((1E)hept-1-enoyl)phenyl)ethynyl)-2-methylphenyl)ethynyl)benzonitrile were as follows:

123

$^1$H-NMR (δ): 0.91(t,3H,J=6.6 Hz),1.25–1.54(m,6H), 2.22 (dt,2H,Jd=6.9 Hz,Jt=6.9 Hz),2.50(s,3H),6.27(dt,1H, Jd=15.7 Hz,Jt=6.9 Hz),6.37(d,1H,J=15.7 Hz),7.26–7.72(m, 11H)

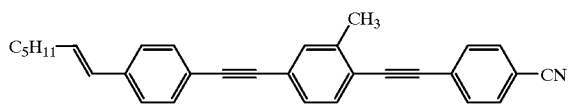

The phase sequence of 4-(2-(4-(2-(4-((1E)hept-1-enoyl) phenyl)ethynyl)-2-methylphenyl)ethynyl)benzonitrile was evaluated through a polarization microscopic observation. The compound exhibited a crystalline phase below 107° C., a nematic phase in the range of 107 to 270° C., and an isotropic phase over 270° C. It was thus determined that this compound was a liquid crystalline compound. Further, the Δn of this compound was determined to be 0.58, which is an extremely large value.

The $^1$H-NMR spectrum data and the structural formula of 4-(2-(2-methyl-4-(2-(4-(2-pentylcyclopropyl)phenyl) ethynyl)phenyl)ethynyl)benzonitrile were as follows:

124

$^1$H-NMR (δ): 0.76–0.92(m,5H),1.05–1.43(m,9H), 1.55–1.64(m,1H),2.50(s,3H),7.00–7.66(m,11H)

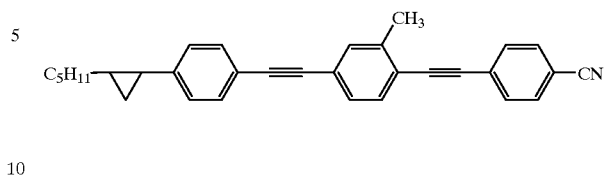

The phenylacetylene compound having a cyclopropane or alkenyl group bound to its skeleton in accordance with the present invention, as well as the liquid crystal composition containing this compound, is large in refractive index anisotropy, stable, and easy to mix with other liquid crystals, and thus is particularly useful as a material for liquid crystal elements such as STN (supertwisted nematic) liquid crystal elements or PDLC (polymer dispersed liquid crystal) elements.

The structural formulae of the compounds used in the above examples are shown below:

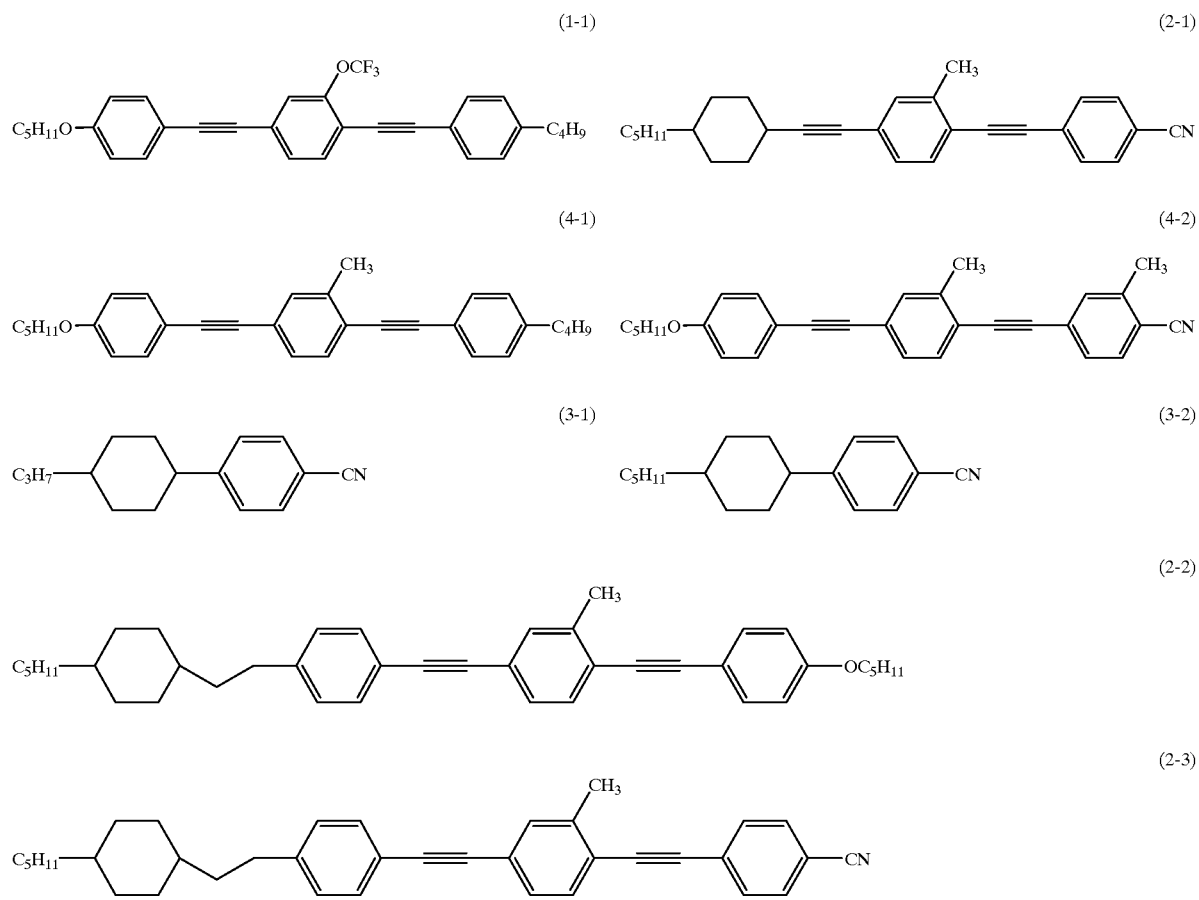

Example 3-1

33.4 wt % of the compound (1-1) represented by the formula (3A) 23.1 wt % of the compound (2-1) represented by the formula (3B), 34.6 g of the compound (4-1) and 8.9 wt % of the compound (4-2) both represented by the formula (3D) were mixed to prepare liquid crystal composition (1).

The property of the liquid crystal phase of the composition (1) was determined. The composition (1) exhibited a nematic phase over quite a wide range of 36 to 172° C. Further, using the wedge-shaped cell, the Δn of the composition (1) was determined to be 0.39 (40° C.), which is an extremely large value. It was determined that the composition (1) has a large Δn and exhibits a liquid crystal phase over quite a wide temperature range.

Example 3-2

26.7 wt % of the compound (1-1) represented by the formula (3A), 18.5 wt % of the compound (2-1) represented by the formula (3B), 10.0 wt % of the compound (3-1) and 10.0 wt % of the compound (3-2) both represented by the formula (3C), 27.7 wt % of the compound (4-1) and 7.1 wt % of the compound (4-2) both represented by the formula (3D) were mixed to prepare liquid crystal composition (2).

The property of the liquid crystal phase of the composition (2) was determined. The composition (2) exhibited a nematic phase over quite a wide range of 18 to 143° C. Further, the Δn of the composition (2) was determined to be 0.34, which is an extremely large value. It was determined that the composition (2) has a large Δn and exhibits a liquid crystal phase over quite a wide temperature range including room temperature.

Comparative Example 1

Liquid crystal composition (2R) was prepared in the same way as for the liquid crystal composition (2) in Example 3-2, except that the compound (1-1) represented by the formula (3A) was not added, and the properties of the composition (2R) were determined. The composition (2R) exhibited a nematic phase in the range of 41 to 138° C., which range was narrower than that of the composition (2). The lower critical temperature was particularly raised, so that a liquid crystal phase did not appear at room temperature. Further, the Δn of the compound was determined to be 0.29 (42° C.), which temperature is lower than that of the composition (2).

It was thus demonstrated that the combination of the components in the liquid crystal composition according to the present invention contributed to widening the temperature range in which a liquid crystal phase is exhibited, and increasing the Δn.

Example 3-3

19.2 wt % of the compound (1-1) represented by the formula (3A), 15.9 wt % of the compound (2-1), 10.5 wt % of the compound (2-2), and 7.5 wt % of the compound (2-3), all represented by the formula (3B), 24.3 wt % of the compound (4-1) and 6.2 wt % of the compound (4-2) both represented by the formula (3D) were mixed to prepare liquid crystal composition (3).

The property of the liquid crystal phase of the composition (3) was determined. The composition (3) exhibited a nematic phase over quite a wide range of 15 to 189° C., including room temperature. Further, using the wedge-shaped cell, the Δn of the composition (3) was determined to be 0.41 (20° C.), which is an extremely large value. It was determined that the composition (3) has a large Δn and exhibits a liquid crystal phase over quite a wide temperature range including room temperature.

The liquid crystal composition according to the present invention is large in refractive index anisotropy, stable, and easy to mix with other liquid crystals, and thus is particularly useful as a material for liquid crystal elements such as STN (supertwisted nematic) liquid crystal elements or PDLC (polymer dispersed liquid crystal) elements.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A phenylacetylene compound represented by the formula (2A):

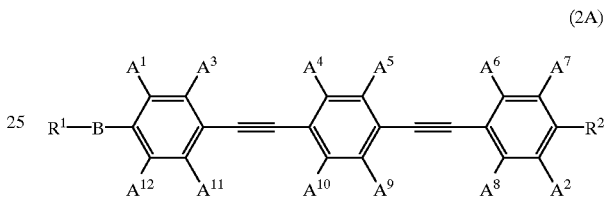

(2A)

wherein $A^1$ to $A^{12}$ each independently stands for a hydrogen atom, a fluorine atom, or an alkyl or alkoxy group having 1 to 10 carbon atoms optionally substituted with at least one fluorine atom, with at least one of $A^1$ to $A^{12}$ being an alkyl or alkoxy group having 1 to 10 carbon atoms optionally substituted with at least one fluorine atom; B stands for:

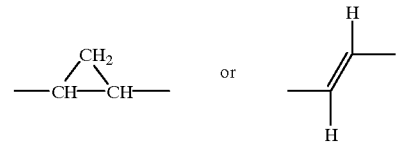

$R^1$ stands for a straight or branched alkyl group having 1 to 12 carbon atoms optionally substituted with at least one fluorine atom; $R^2$ stands for a hydrogen atom, a fluorine atom, a cyano group, —$SF_5$, —NCS, a 4-$R^3$-(cycloalkyl) group, a 4-$R^3$-(cycloalkenyl) group, or a $R^4$—(O)q group, wherein $R^3$ stands for a hydrogen atom or a straight or branched alkyl group having 1 to 12 carbon atoms optionally substituted with at least one fluorine atom, $R^4$ stands for a straight or branched alkyl group having 1 to 12 carbon atoms optionally substituted with at least one fluorine atom, and q is 0 or 1.

2. A liquid crystal composition comprising at least one phenylacetylene compound represented by formula (2A):

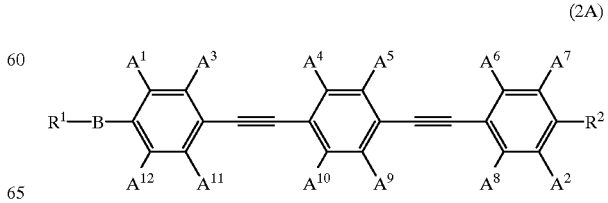

(2A)

wherein

A¹ to A¹² each independently stands for a hydrogen atom, a fluorine atom, or an alkyl or alkoxy group having 1 to 10 carbon atoms optionally substituted with at least one fluorine atom, with at least one of A¹ to A¹² being an alkyl or alkoxy group having 1 to 10 carbon atoms optionally substituted with at least one fluorine atom;

B stands for:

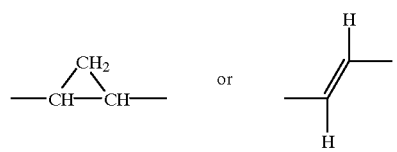

R¹ stands for a straight or branched alkyl group having 1 to 12 carbon atoms optionally substituted with at least one fluorine atom;

R² stands for a hydrogen atom, a fluorine atom, a cyano group, —SF₅, —NCS, a 4-R³-(cycloalkyl) group, a 4-R³-(cycloalkenyl) group, or a R⁴—(O)$_q$ group, wherein R³ stands for a hydrogen atom or a straight or branched alkyl group having 1 to 12 carbon atoms optionally substituted with at least one fluorine atom, R⁴ stands for a straight or branched alkyl group having 1 to 12 carbon atoms optionally substituted with at least one fluorine atom, and q is 0 or 1.

3. A liquid crystal element comprising a liquid crystal composition of claim 2 held between a pair of electrode substrates.

4. A liquid crystal composition comprising at least one benzylidynyl tolan compound represented by the formula (3A), and at least one compound selected from the group consisting of compounds represented by any one of the formulae (3B), (3C), and (3D):

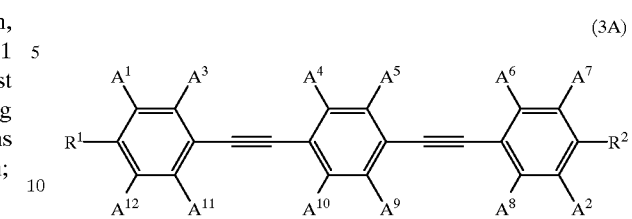
(3A)

wherein A¹ to A¹² each independently stands for a hydrogen atom, a fluorine atom, or an alkyl or alkoxy group having 1 to 10 carbon atoms optionally substituted with at least one fluorine atom, with at least one of A¹ to A¹² being an alkyl or alkoxy group having 1 to 10 carbon atoms substituted with at least one fluorine atom; R¹ and R² each independently stands for a hydrogen atom, a fluorine atom, a cyano group, —SF₅, —NCS, a 4-R³-(cycloalkyl) group, a 4-R³-(cycloalkenyl) group, or a R⁴—(O)q group, wherein R³ stands for a hydrogen atom or a straight or branched alkyl group having 1 to 12 carbon atoms optionally substituted with at least one fluorine atom, R⁴ stands for a straight or branched alkyl group having 1 to 12 carbon atoms optionally substituted with at least one fluorine atom, and q is 0 or 1;

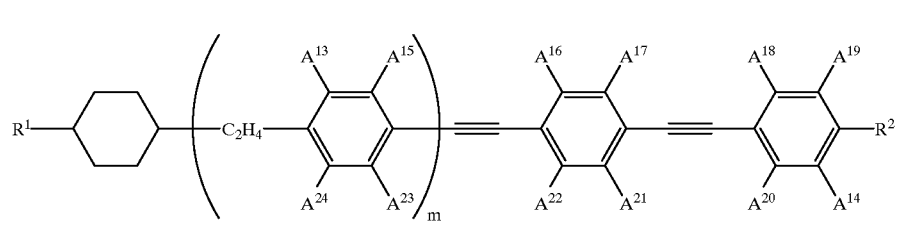
(3B)

wherein A¹³ to A²⁴ each independently stands for a hydrogen atom, a fluorine atom, or an alkyl group having 1 to 10 carbon atoms; m is 0 or 1; R¹ stands for a hydrogen atom or a straight or branched alkyl group having 1 to 12 carbon atoms optionally substituted with at least one fluorine atom; R² stands for R¹, a fluorine atom, a cyano group, a 4-R³¹-(cycloalkyl) group, a 4-R³¹-(cycloalkenyl) group, or a R⁴¹-(O)q group, wherein R³¹ stands for a hydrogen atom or a straight or branched alkyl group having 1 to 12 carbon atoms optionally substituted with at least one fluorine atom, R⁴¹ stands for a straight or branched alkyl group having 1 to 12 carbon atoms optionally substituted with at least one fluorine atom, and q is 0 or 1;

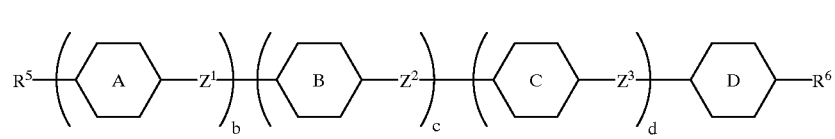
(3C)

wherein Rings A, B, C, and D each independently stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl, with at least one of hydrogen atoms on Rings A, B, C, and D being optionally substituted with a fluorine atom; $R^5$ and $R^6$ each independently stands for a hydrogen atom, a fluorine atom, a fluoromethyl group, a difluoromethyl group, a trifluoromethyl group, a fluoromethoxy group, a difluoromethoxy group, a trifluoromethoxy group, a cyano group, an alkyl group having 1 to 12 carbon atoms, an alkenyl group having 2 to 12 carbon atoms, an alkoxy group having 1 to 12 carbon atoms, an alkenyloxy group having 2 to 12 carbon atoms, an alkynyloxy group having 3 to 12 carbon atoms, an alkoxyalkyl group having 2 to 16 carbon atoms, or an alkoxyalkenyl group having 3 to 16 carbon atoms, with at least one of methylene groups in these groups being optionally substituted with an oxygen, sulfur, or silicon atom, wherein these groups may be straight or branched; $Z^1$, $Z^2$, and $Z^3$ each independently stands for —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond; b, c, and d each independently denotes 0 or 1 with b+c+d≧1;

(3D)

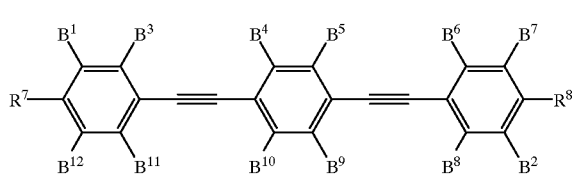

wherein $B^1$ to $B^{12}$ each independently stands for a hydrogen atom, a fluorine atom, or an alkyl or alkoxy group having 1 to 10 carbon atoms, with at least one of $B^1$ to $B^{12}$ being an alkyl or alkoxy group having 1 to 10 carbon atoms; $R^7$ and $R^8$ each independently stands for a hydrogen atom, a fluorine atom, a cyano group, a 4-$R^9$-(cycloalkyl) group, a 4-$R^9$-(cycloalkenyl) group, or a $R^{10}$—(O)q group, wherein $R^9$ stands for a hydrogen atom or a straight or branched alkyl group having 1 to 12 carbon atoms optionally substituted with at least one fluorine atom, $R^{10}$ stands for a straight or branched alkyl group having 1 to 12 carbon atoms optionally substituted with at least one fluorine atom, and q is 0 or 1.

5. The liquid crystal composition of claim 4 wherein Ring D in the formula (3C) is selected from the group consisting of 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, and 6,3-cyclohexenylene, each optionally substituted with at least one fluorine atom.

6. The liquid crystal composition of claim 4 wherein the compound represented by the formula (3C) is selected from the group consisting of compounds represented by any one of the formulae (4) to (10):

(4)

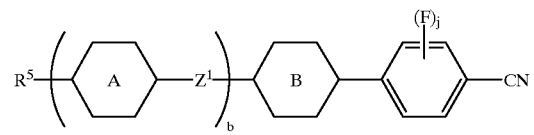

(5)

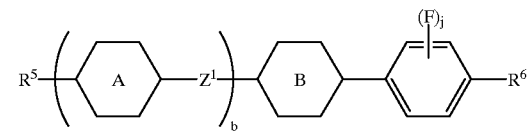

(6)

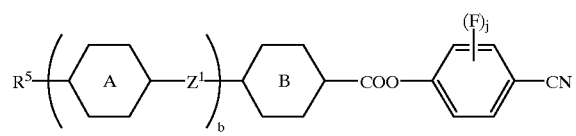

(7)

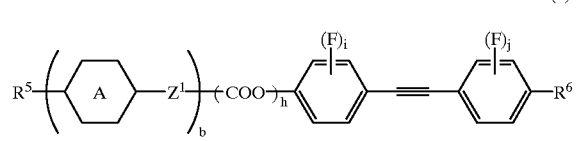

(8)

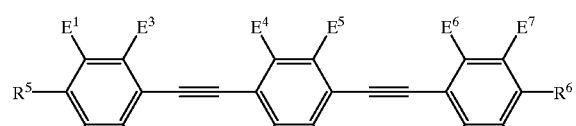

(9)

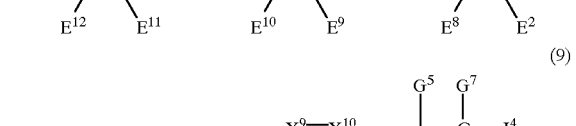

(10)

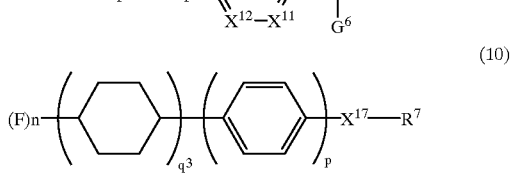

wherein in the formula (4) to (7), $R^5$, $R^6$, Ring A, Ring B, $Z^1$, and b mean the same as those in the formula (3C); j is 0, 1, or 2; h is 0 or 1; i is 0, 1, or 2; in the formula (8), $E^1$ to $E^{12}$ each independently stands for a hydrogen, fluorine, or chlorine atom; in the formula (9), $X^9$ to $X^{12}$ each independently stands for CH or CF; $J^4$ stands for a hydrogen atom, a fluorine atom, a cyano group, an alkyl group having 1 to 12 carbon atoms optionally substituted with at least one fluorine atom, an alkenyl group having 2 to 12 carbon atoms optionally substituted with at least one fluorine atom, an alkoxy group having 1 to 12 carbon atoms optionally substituted with at least one fluorine atom, an alkenyloxy group having 2 to 12 carbon atoms optionally substituted with at least one fluorine atom, an alkynyloxy group having 3 to 12 carbon atoms optionally substituted with at least one fluorine atom, or an alkoxyalkyl group having 2 to 12 carbon atoms optionally substituted with at least one fluorine atom; $J^5$ stands for a hydrogen atom, a fluorine atom, a cyano group, or $J^6$—(O)m$^2$, wherein m$^2$ is 0 or 1, and $J^6$ stands for an alkyl group having 1 to 12 carbon atoms, an alkenyl group having 2 to 16 carbon atoms, or an alkynyl group having 3 to 16 carbon atoms, each of which groups may optionally be substituted with at least one fluorine atom; $E^1$ and $E^2$ each independently stands for one of the following groups, wherein $X^{13}$ to $X^{16}$ each independently stands for CH or CF:

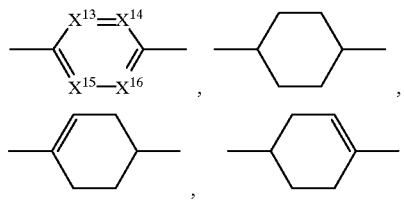

$W^1$ stands for —$C_2H_4$—, —$CH_2O$—, or —$OCH_2$—; $f^1$ and $f^2$ each independently denotes 0 or 1, while both $f^1$ and $f^2$ are not 1 at the same time; when $f^1$ is 1, at least one of $E^1$ and $E^2$ is a group represented by the formula:

$G^5$ to $G^8$ each independently stands for a hydrogen or fluorine atom; in the formula (10), $R^7$ stands for an alkyl group having 1 to 10 carbon atoms, at least one hydrogen atom on the benzene ring in the formula (10) may optionally be substituted with a fluorine atom; n, p, and $q^3$ each denotes 1 or 2; $X^{17}$ stands for trans —CH=CH— or an ethynyl group, provided that when n is 1, $X^{17}$ may be —$CH_2$—$CH_2$—.

7. The liquid crystal composition of claim 4 wherein a compositional ratio of the total amount of the compounds represented by the formula (3A) is 5 to 90 mol %, and a compositional ratio of the total amount of the compounds represented by the formulae (3B), (3C) and (3D) is 10 to 95 mol %.

8. A liquid crystal element comprising a liquid crystal composition of claim 4 held between a pair of electrode substrates.

* * * * *